US010202448B2

(12) United States Patent
Barrett et al.

(10) Patent No.: US 10,202,448 B2
(45) Date of Patent: Feb. 12, 2019

(54) ANTI-IL-23 ANTIBODIES

(71) Applicant: Boehringer Ingelheim International GmbH, Ingelheim am Rhein (DE)

(72) Inventors: Rachel Rebecca Barrett, Bethel, CT (US); Keith A. Canada, Woodbury, CT (US); Katrina Mary Catron, Middlebury, CT (US); Robert Copenhaver, Portland, OR (US); Lee Edward Frego, Hopewell Junction, NY (US); Ernest Lee Raymond, New Milford, CT (US); Sanjaya Singh, Sandy Hook, CT (US); Xiangyang Zhu, Ridgefield, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 15/228,254

(22) Filed: Aug. 4, 2016

(65) Prior Publication Data
US 2016/0333091 A1 Nov. 17, 2016

Related U.S. Application Data

(62) Division of application No. 14/302,986, filed on Jun. 12, 2014, now Pat. No. 9,441,036, which is a division of application No. 13/287,208, filed on Nov. 2, 2011, now Pat. No. 8,778,346.

(60) Provisional application No. 61/448,785, filed on Mar. 3, 2011, provisional application No. 61/412,594, filed on Nov. 11, 2010, provisional application No. 61/411,953, filed on Nov. 10, 2010, provisional application No. 61/410,158, filed on Nov. 4, 2010.

(51) Int. Cl.
*C07K 16/24* (2006.01)
*A61K 39/00* (2006.01)
*A61K 39/395* (2006.01)
*C12N 15/113* (2010.01)

(52) U.S. Cl.
CPC .......... *C07K 16/244* (2013.01); *C12N 15/113* (2013.01); *A61K 2039/505* (2013.01); *C07K 2317/24* (2013.01); *C07K 2317/34* (2013.01); *C07K 2317/565* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 6,060,284 A | 5/2000 | Bazan | |
| 6,479,634 B1 | 11/2002 | Bazan | |
| 6,495,667 B1 | 12/2002 | Bazan | |
| 6,610,285 B1 | 8/2003 | Hirata | |
| 6,756,481 B2 | 6/2004 | Chirica et al. | |
| 6,835,825 B1 | 12/2004 | Bazan | |
| 7,090,847 B1 | 8/2006 | Oppmann et al. | |
| 7,183,382 B2 | 2/2007 | Oppmann et al. | |
| 7,252,967 B2 | 8/2007 | Hirata | |
| 7,282,204 B2 | 10/2007 | Oft et al. | |
| 7,332,156 B2 | 2/2008 | Bowman et al. | |
| 7,411,041 B2 | 8/2008 | Chirica et al. | |
| 7,422,743 B2 | 9/2008 | Chirica et al. | |
| 7,427,402 B2 | 9/2008 | Kastelein et al. | |
| 7,491,391 B2 | 2/2009 | Benson et al. | |
| 7,501,247 B2 | 3/2009 | Kastelein et al. | |
| 7,510,709 B2 | 3/2009 | Gurney | |
| 7,510,853 B2 | 3/2009 | Chirica et al. | |
| 7,575,741 B2 | 8/2009 | Bowman et al. | |
| 7,608,690 B2 | 10/2009 | Bazan | |
| 7,740,848 B2 | 6/2010 | Kastelein et al. | |
| 7,749,718 B2 | 7/2010 | Chirica et al. | |
| 7,750,126 B2 | 7/2010 | Hirata | |
| 7,754,214 B2 | 7/2010 | Chirica et al. | |
| 7,790,862 B2 | 9/2010 | Lewis et al. | |
| 7,807,160 B2 | 10/2010 | Presta et al. | |
| 7,807,414 B2 | 10/2010 | Benson et al. | |
| 7,820,168 B2 | 10/2010 | Cua et al. | |
| 7,872,102 B2 | 1/2011 | Beidler et al. | |
| 7,883,695 B2 | 2/2011 | Oppmann et al. | |
| 7,887,806 B2 | 2/2011 | Chirica et al. | |
| 7,893,215 B2 | 2/2011 | Bowman et al. | |
| 7,910,703 B2 | 3/2011 | Lewis et al. | |
| 7,935,344 B2 | 5/2011 | Benson et al. | |
| 7,993,645 B2 | 8/2011 | Benson et al. | |
| 8,106,177 B2 | 1/2012 | Benson et al. | |
| 8,778,346 B2 | 7/2014 | Barrett et al. | |
| 9,441,036 B2 | 9/2016 | Barrett et al. | |

(Continued)

FOREIGN PATENT DOCUMENTS

EP 1 072 610 A1 1/2001
EP 2 786 746 A1 10/2014
(Continued)

OTHER PUBLICATIONS

Yannam et al, Journal of Neuroimmune Pharmacology 2012; vol. 7; pp. 95-112.*
Croxford et al, Cytokine & Growth Factor Reviews, 2014, vol. 25, pp. 415-421.*
Langowski et al, Nature, 2006, vol. 442, No. 27, pp. 461-465.*
Tang et al, Immunology, 2011, vol. 135, pp. 112-124.*
Aggarwal et al., "Interleukin-23 Promotes a Distinct CD4 T Cell Activation State Characterized by the Production of Interleukin-17*," Journal of Biological Chemistry, 2003, 278(3): 1910-1914.
Alegre et al., "A Non-Activativing "Humanized" Anti-CD3 Monoclonal Antibody Retains Immunosuppressive Properties in Vivo," Transplantation; Jun. 1994, 57(11):1537-1543.

(Continued)

*Primary Examiner* — Elizabeth C. Kemmerer
(74) *Attorney, Agent, or Firm* — Foley & Lardner LLP

(57) ABSTRACT

The present invention relates to anti-IL-23p19 binding compounds, in particular new humanized anti-IL-23p19 antibodies and therapeutic and diagnostic methods and compositions for using the same.

9 Claims, 3 Drawing Sheets

Specification includes a Sequence Listing.

(56) References Cited

U.S. PATENT DOCUMENTS

| | | |
|---|---|---|
| 2004/0219150 A1 | 11/2004 | Cua et al. |
| 2004/0258686 A1 | 12/2004 | Chirica et al. |
| 2005/0039222 A1 | 2/2005 | Habu et al. |
| 2005/0100917 A1 | 5/2005 | Chirica et al. |
| 2005/0100918 A1 | 5/2005 | Chirica et al. |
| 2005/0100965 A1 | 5/2005 | Ghayur et al. |
| 2005/0208052 A1 | 9/2005 | Katsikis et al. |
| 2005/0244874 A1 | 11/2005 | Kastelein et al. |
| 2005/0287593 A1 | 12/2005 | Kastelein et al. |
| 2006/0088523 A1 | 4/2006 | Andya et al. |
| 2006/0140958 A1 | 6/2006 | Hogan et al. |
| 2007/0009526 A1 | 1/2007 | Benson et al. |
| 2007/0218060 A1 | 9/2007 | Long et al. |
| 2008/0199460 A1 | 8/2008 | Cua et al. |
| 2008/0200655 A1 | 8/2008 | Sek |
| 2008/0254026 A1 | 10/2008 | Long et al. |
| 2008/0311043 A1 | 12/2008 | Hoffman et al. |
| 2009/0060906 A1 | 3/2009 | Barry et al. |
| 2009/0092604 A1 | 4/2009 | Cua et al. |
| 2009/0123479 A1 | 5/2009 | Bembridge et al. |
| 2009/0156788 A1 | 6/2009 | Presta et al. |
| 2009/0291062 A1 | 11/2009 | Fraunhofer et al. |
| 2010/0003251 A1 | 1/2010 | Oft et al. |
| 2010/0041144 A1 | 2/2010 | Bazan |
| 2010/0111950 A1 | 5/2010 | Cua et al. |
| 2010/0111954 A1 | 5/2010 | Cua et al. |
| 2010/0111966 A1 | 5/2010 | Presta et al. |
| 2010/0135998 A1 | 6/2010 | Bowman et al. |
| 2010/0143357 A1 | 6/2010 | Cua et al. |
| 2010/0254991 A1 | 10/2010 | Kastelein et al. |
| 2010/0261273 A1 | 10/2010 | Chirica et al. |
| 2010/0266582 A1 | 10/2010 | Gurney |
| 2010/0266583 A1 | 10/2010 | Gurney |
| 2010/0272731 A1 | 10/2010 | Presta et al. |
| 2010/0291084 A1 | 11/2010 | Kopf et al. |
| 2010/0322863 A1 | 12/2010 | Benson et al. |
| 2011/0002942 A1 | 1/2011 | Presta et al. |
| 2011/0059087 A1 | 3/2011 | Lewis et al. |
| 2011/0135597 A1 | 6/2011 | Bowman et al. |
| 2011/0142831 A1 | 6/2011 | Cua et al. |
| 2011/0142853 A1 | 6/2011 | Presta et al. |
| 2011/0159589 A1 | 6/2011 | Lewis et al. |
| 2011/0177022 A1 | 7/2011 | Oppmann et al. |
| 2011/0195455 A1 | 8/2011 | Benson et al. |
| 2011/0206686 A1 | 8/2011 | Bembridge et al. |
| 2011/0229490 A1 | 9/2011 | Li et al. |
| 2011/0250201 A1 | 10/2011 | Smith |
| 2011/0311527 A1 | 12/2011 | Stern et al. |
| 2012/0128689 A1 | 5/2012 | Clarkson et al. |
| 2012/0195885 A1 | 8/2012 | Correia et al. |
| 2012/0277799 A1 | 11/2012 | Winslow et al. |
| 2012/0282269 A1 | 11/2012 | Barrett et al. |
| 2013/0004501 A1 | 1/2013 | Towne et al. |
| 2013/0028907 A1 | 1/2013 | Parshad et al. |
| 2013/0115166 A1 | 5/2013 | Clarke et al. |
| 2013/0216525 A1 | 8/2013 | Chen |
| 2014/0046063 A1 | 2/2014 | Moussy et al. |
| 2014/0178401 A1 | 6/2014 | Nabozny et al. |
| 2014/0303357 A1 | 10/2014 | Lim et al. |
| 2014/0363444 A1 | 12/2014 | Barrett et al. |
| 2016/0060338 A1 | 3/2016 | Barrett et al. |
| 2016/0222102 A1 | 8/2016 | Arndt et al. |
| 2016/0333091 A1 | 11/2016 | Barrett et al. |
| 2017/0022294 A1 | 1/2017 | Singh et al. |

FOREIGN PATENT DOCUMENTS

| | | |
|---|---|---|
| WO | WO-99/05280 A1 | 2/1999 |
| WO | WO-99/40195 A1 | 8/1999 |
| WO | WO-99/54357 A1 | 10/1999 |
| WO | WO-01/18051 A2 | 3/2001 |
| WO | WO-01/85790 A2 | 11/2001 |
| WO | WO-03/039485 A2 | 5/2003 |
| WO | WO-2004/042009 A2 | 5/2004 |
| WO | WO-2004/058178 A2 | 7/2004 |
| WO | WO-2004/071517 A2 | 8/2004 |
| WO | WO-2004/081190 A2 | 9/2004 |
| WO | WO-2005/044294 A2 | 5/2005 |
| WO | WO-2005/052157 A1 | 6/2005 |
| WO | WO-2005/079837 A1 | 9/2005 |
| WO | WO-2005/108616 A1 | 11/2005 |
| WO | WO-2006/036922 A2 | 4/2006 |
| WO | WO-2006/068987 A2 | 6/2006 |
| WO | WO-2007/005647 A2 | 1/2007 |
| WO | WO-2007/005955 A2 | 1/2007 |
| WO | WO-2007/024846 A2 | 3/2007 |
| WO | WO-2007/027714 A2 | 3/2007 |
| WO | WO-2007/027761 A2 | 3/2007 |
| WO | WO-2007/076523 A2 | 7/2007 |
| WO | WO-2007/076524 A2 | 7/2007 |
| WO | WO-2007/147019 A2 | 12/2007 |
| WO | WO-2007/149814 A1 | 12/2007 |
| WO | WO-2008/103432 A1 | 8/2008 |
| WO | WO-2008/103473 A1 | 8/2008 |
| WO | WO-2008/106131 A2 | 9/2008 |
| WO | WO-2008/153610 A2 | 12/2008 |
| WO | WO-2009/032954 A1 | 3/2009 |
| WO | WO-2009/043933 A1 | 4/2009 |
| WO | WO-2009/053493 A1 | 4/2009 |
| WO | WO-2009/055936 A1 | 5/2009 |
| WO | WO-2009/073569 A2 | 6/2009 |
| WO | WO-2009/082624 A2 | 7/2009 |
| WO | WO-2010/017598 A1 | 2/2010 |
| WO | WO-2010/027766 A1 | 3/2010 |
| WO | WO-2010/115092 A2 | 10/2010 |
| WO | WO-2010/115786 A1 | 10/2010 |
| WO | WO-2011/011797 A2 | 1/2011 |
| WO | WO-2011/056600 A1 | 5/2011 |
| WO | WO-2011/066369 A2 | 6/2011 |
| WO | WO-2011/070339 A1 | 6/2011 |
| WO | WO-2011/103105 A1 | 8/2011 |
| WO | WO-2011/104381 A2 | 9/2011 |
| WO | WO-2011/109365 A2 | 9/2011 |
| WO | WO-2011/159655 A2 | 12/2011 |
| WO | WO-2011/159750 A1 | 12/2011 |
| WO | WO-2012/009760 A1 | 1/2012 |
| WO | WO-2012/032181 A2 | 3/2012 |
| WO | WO-2012/061448 A1 | 5/2012 |
| WO | WO-2012/093254 A1 | 7/2012 |
| WO | WO-2012/103345 A1 | 8/2012 |
| WO | WO-2013/165791 A1 | 11/2013 |
| WO | WO-2014/004436 A2 | 1/2014 |
| WO | WO-2014/143540 | 9/2014 |
| WO | WO-2014/149425 A1 | 9/2014 |
| WO | WO-2017/048901 A1 | 3/2017 |

OTHER PUBLICATIONS

Alunno et al., "Targeting the IL-23/IL-17 axis for the treatment of psoriasis and psoriatic arthritis," Expert Opinion on Biological Therapy, 2015, 15(12):1727-1737.

Anonymous: "A 52-Week, Phase 3, Randomized, Active Comparator and Placebo-Controlled, Parallel Design Study to Evaluate the Efficacy and Safety/Tolerability of Subcutaneous SCH 9000222/MK-3222, Followed by an Optional Long-Term Safety Extension Study, in Subjects with Moderate-to-Severe Chronic Plaque Psoriasis" Dec. 30, 2014, 4 pages, Clinical Trials Identifier: NCT01729754, Clinicaltrials.gov.

Anonymous: "A Phase 2 Multicenter, Randomized, Pacebo- and Active-Comparator-Controlled, Dose-Ranging Trial to Evaluate CNTO 1959 for the Treatment of Subjects with Moderate to Sever Plaque-type Psoriasis (X-PLORE)" Mar. 10, 2014, 4 pages, Clinical Trials Identifier NCT01483599, Clinicaltrials.gov.

Anonymous: "A Phase 2a, Multicenter, Randomized, Double-blind, Placebo-controlled Study Evaluating the Efficacy and Safety of Guselkumab in the Treatment of Subjects with Active Psoriatic Arthritis," Jan. 26, 2015, 4 pages, Clinical Trials Identifier: NCT02319759, Clinicaltrials.gov.

Baerveldt et al., "Ustekinumab improves psoriasis-related gene expression in noninvolved psoriatic skin without inhibition of the antimicrobial response," British Journal of Dermatology, 2013, 168:990-998.

(56) References Cited

OTHER PUBLICATIONS

Bandzar et al., "Crohn's disease: A review of treatment options and current research," Cellular Immunology, 2013, 286:45-52.

Beyer et al., "Crystal Structures of the Pro-Inflammatory Cytokine Interleukin-23 and its Complex with a High-Affinity Neutralizing Antibody," Journal of Molecular Biology, 2008, 382:942-955.

Bhambhani et al., "Formulation Design and High-Throughput Excipient Selection Based on Structural Integrity and Conformational Stability of Dilute and Highly Concentrated IgG1 Monoclonal Antibody Solutions," Journal of Pharmaceutical Sciences, 2012, 101(3):1120-1135.

Brodmerkel et al., "The Skin and Circulating Immune Profile of Therapeutic IL-12/23 Blockade in Psoriasis Patients Treated with Ustekinumab," Clinical Immunology, Academic Press, Jan. 1, 2009, 131:S5, Abstract.

Campa et al., "A Review of Biologic Therapies Targeting IL-23 and IL-17 for Use in Moderate-to-Severe Plaque Psoriasis," Dermatology Therapy, 2016, 6:1-12.

Cao et al., "Anti-IL-23 antibody blockade of IL-23/IL-17 pathway attenuates airway obliteration in rat orthotopic tracheal transplantation," International Immunopharmacology, 2011, 11:569-575.

Casset et al., "A peptide mimetic of an anti-CD4 monoclonal antibody by rational design," Biochemical and Biophysical Research Communications, 2003, 307:198-205.

Castro et al., "Reslizumab for Poorly Controlled, Eosinophilic Asthma, A Randomized, Placebo-controlled Study," Am. J. Respir. Crit. Care Med., 2011, 184:1125-1132.

Catalog No. AF1716. "Anti-human IL-23 p19 Antibody," Lot No. JMB01., R&D Systems, Inc., Dec. 17, 2003.

Chan et al., "Therapeutic antibodies for autoimmunity and inflammation," Nature Reviews, Immunology, May 2010, 10:301-316.

Choy et al., "Th2 and Th17 inflammatory pathways are reciprocally regulated in asthma," www.ScienceTranslationalMedicine.org, 2015, 7(301):301ra129, 11 pages.

Ciprandi et al., "Serum IL-23 Strongly and Inversely Correlates with FEV1 in Asthmatic Children," International Archives of Allergy and Immunology, 2012, 159(2):183-186.

ClinicalTrials.gov study NCT01018810, published Nov. 24, 2009, (downloaded from https://clinicaltrials.gov/ct2/history/NCT01018810, 6 pages.

ClinicalTrials.gov study NCT01483599, published Nov. 29, 2011 (downloaded from https://clinicaltrials.gov/ct2/history/NCT01483599, 6 pages.

ClinicalTrials.gov study NCT01729754, published Nov. 14, 2012 (downloaded from https://clinicaltrials.gov/ct2/history/NCT01729754, 7 pages.

ClinicalTrials.gov study NCT02031276, published Jan. 8, 2014, 7 pages.

ClinicalTrials.gov study NCT02319759, published Dec. 15, 2014 (downloaded from https://clinicaltrials.gov/ct2/history/NCT02319749), 7 pages.

Cupparic et al., "Serum IL-23 in Asthmatic Children," Journal of Biological Regulators & Homeostatic Agents, 2012, 26(1(S)):53-61.

Daugherty et al., "Formulation and delivery issues for monoclonal antibody therapeutics," Advanced Drug Delivery Reviews, 2006, 58:686-706.

eBioscience, Anti-Mouse IL-23 p19 Purified; Catalog No. 14-7232; Clone G23-8; According to all information that could be obtained from publicly available sources by Applicants, G23-8 antibody was available for purchase in 2005.

eBioscience, Anti-Mouse IL-23 p19 Purified; Catalog No. 14-7233; Clone 5B2; According to all information that could be obtained from publicly available sources by Applicants, 5B2 antibody was available for purchase in 2007.

eBioscience, Mouse IL-23 ELISA Ready-SET-Go! ELISA Kit, Catalog No. 88-7923, 6 pages. According to all information that could be obtained from publicly available sources by Applicants, Mouse IL-23 ELISA Ready-SET-Go! ELISA Kit was available for purchase in 2007.

Eijnden, Serge Vanden et al., "Preferential production of the IL-12(p40)/IL-23(19) heterodimer by dendritic cells from human newborns," Eur. J. Immunol., 2006, 36:21-26.

Fahy, John V., "Eosinophilic and Neutrophilic Inflammation in Asthma, Insights from Clinical Studies," Proceedings of the American Thoracic Society, 2009, 6:256-259.

Ferrara et al., "Recombinant renewable polyclonal antibodies," mABs, 2015, 7(1):32-41.

Fichtner-Feigl et al., "Treatment of murine Th1- and Th2-mediated inflammatory bowel disease with NF-kB decoy oligonucleotides," Journal of Clinical Investigation, Nov. 2005, 115(11):3057-3071.

Gaffen et al., "The IL-23-IL-17 immune axis: from mechanisms to therapeutic testing," Nature Reviews, 2014, 14:585-600.

Gordon et al., "A Phase 2 Trial of Guselkumab versus Adalimumab for Plaque Psoriasis," New England Journal of Medicine, 2015, 373(2):136-144.

Gudjonsson et al., "Assessment of the Psoriatic Transcriptome in a Large Sample: Additional Regulated Genes and Comparisons with In Vitro Models," Journal of Investigative Dermatology, 2010, 130:1829-1840.

Haldar et al., "Mepolizumab and Exacerbations of Refractory Eosinophilic Asthma," The New England Journal of Medicine, 2009, 360:973-984.

Happel et al., "Divergent roles of IL-23 and IL-12 in host defense against Klebsiella pneumoniae" Journal of Experimental Medicine, Sep. 2005, 202(6):761-769.

Hegazi et al., "Carbon monoxide ameliorates chronic murine colitis through a heme oxygenase 1-dependent pathway," Journal of Experimental Medicine, Dec. 2005, vol. 202, No. 12, pp. 1703-1713.

Hegyi et al., "Vitamin D Analog Calcipotriol Suppresses the Th17 Cytokine-Induced Proinflammatory S100 'Alarmins' Psoriasin (S100A7) and Koebnerisin (S100A15) in Psoriasis," Journal of Investigative Dermatology, 2012, 132:1416-1424.

Hoeve et al., "IL-12 receptor deficiency revisited: IL-23-mediated signaling is also impaired in human genetic IL-12 receptor ?1deficiency," Eur. J. Immunol., 2003, 33:3393-3397.

Hu et al., "Information contributed by meta-analysis in exposure-response modeling: application to phase 2 does selection of guselkumab in patients with moderate-to-severe psoriasis," Journal of Pharmacokinet. Pharmacodyn., 2014, 41:239-250.

International Preliminary Report on Patentability and Written Opinion for PCT/US2015/041706 dated Feb. 2, 2017.

International Preliminary Report on Patentability for PCT/US2011/058869 dated May 7, 2013.

International Search Report & Written Opinion for PCT/US2011/058869, dated Feb. 27, 2012.

International Search Report and Written Opinion dated Jul. 28, 2017, in PCT/US2017/027332.

International Search Report and Written Opinion dated Oct. 26, 2017 in PCT/US2016/027263.

International Search Report for PCT/US2013/038109 dated Apr. 25, 2013.

International Search Report for PCT/US2015/041706 dated Oct. 15, 2015.

International Search Report for PCT/US2016/016061 dated May 18, 2016.

International Search Report for PCT/US2016/027263 dated Jun. 29, 2016.

International Search Report for PCT/US2016/051844 dated Jan. 10, 2017.

Irvin et al., "Increased frequency of dual-positive TH2/TH17 cells in bronchoalveolar lavage fluid characterizes a population of patients with severe asthma," Journal of Allergy and Clinical Immunology, 2014, 134(5):1175-1186.

Jabbari et al., "Transcriptional Profiling of Psoriasis Using RNA-seq Reveals Previously Unidentified Differentially Expressed Genes," Journal of Investigative Dermatology, 2012 (online Aug. 2011), 132:246-249.

Kastelein et al., "Discovery and Biology of IL-23 and IL-27: Related but Functionally Distinct Regulators of Inflammation," Annual Reviews Immunology, 2007, 25: 221-242.

(56) References Cited

OTHER PUBLICATIONS

Kerdel et al., "An evolution in switching therapy for psoriasis patients who fail to meet treatment goals," Dermatologic Therapy, 2015, 28:390-403.
Kidoya et al., "Fas Ligand Induces Cell-Autonomous IL-23 Production in Dendritic Cells, a Mechanism for Fas Ligand-Induced IL-17 Production," Journal of Immunology, 2005, 8024-8031.
Kikly et al., "The IL-23/Th17 axis: Therapeutic targets for autoimmune inflammation," Current Opinion in Immunology, 2006, 18:670-675.
Kim et al., "Diagnosis and management of psoriasis," Canadian Family Physician, 2017, 63:278-285.
Kofoed et al "New Drugs and Treatment Targets in Psoriasis," Acta Derm. Venereol., 2015, 95:133-139.
Kopp et al., "Clinical improvement in psoriasis with specific targeting of interleukin-23," Nature, 2015, 521(7551):222-226.
Krishnan et al., "Development of Formulations for Therapeutic Monoclonal Antibodies and Fc Fusion Proteins," Formulation and Process Development Strategies for Manufacturing Biopharmaceuticals, 2010, Chapter 16, 383-427.
Krueger et al., "Anti-IL-23A mAb BI 655066 for treatment of moderate-to-severe psoriasis: Safety, efficacy, pharmacokinetics, and biomarker results of a single-rising-dose, randomized, double-blind, placebo-controlled trial," Journal of Allergy and Clinical Immunology, 136:116-124.
Kuwashima et al., "Delivery of Dendritic Cells Engineered to Secrete IFN-? into Central Nervous System Tumors Enhances the Efficacy of Peripheral Tumor Cell Vaccines: Dependence on Apoptotic Pathways," Journal of Immunology, 2005, 175: 2730-2740.
Lee et al., "Increased Expression of Interleukin 23 p19 and p40 in Lesional Skin of Patients with Psoriasis Vulgaris," Journal of Experimental Medicine, 2004, 199(1):125-130.
Leonardi et al., "Efficacy and safety of ustekinumab, a human interleukin-12/23 monoclonal antibody, in patients with psoriasis: 76-weeks results form a randomised, double-blind, placebo-controlled trail (PHOENIX 1)," The Lancet, 2008, 371:1665-1674.
Li et al., "Silencing IL-23 expression by a small hairpin RNA protects against asthma in mice," Experimental and Molecular Medicine, 2011, 43(4):197-204.
MacCallum et al., "Antibody-antigen Interactions: Contact Analysis and Binding Site Topography," J. Mol. Biol., 1996, 262:732-745.
Mallbris et al., "Neutrophil gelatinase-associated lipocalin is a marker for dysregulated keratinocyte differentiation in human skin" Experimental Dermatology, 2002, 11:584-591.
McInnes et al., "Efficacy and safety of secukinumab, a fully human anti-interleukin-17A monoclonal antibody, in patients with moderate-to-severe psoriatic arthritis: a 24-week, randomised, double-blind, placebo-controlled, phase II proof-of-concept trail," Ann. Rheum. Dis., 2014, 73:349-356.
McKinley et al., "TH17 Cells Mediate Steroid-Resistant Airway Inflammation and Airway Hyperresponsiveness in Mice," The Journal of Immunology, 2008, 181:4089-4097.
Morelli et al., "CD4+ T Cell Responses Elicted by Different Subsets of Human Skin Migratory Dendritic Cells," The Journal of Immunology, 2005, 175:7905-7915.
Naji et al., "T Helper 17 Cells and Related Cytokines after Allergen Inhalation Challenge in Allergic Asthmatics," International Archives of Allergy & Immunology, 2014, 165:27-34.
Nakajima et al., "Role of IL-23 and Th17 Cells in Airway Inflammation in Asthma," Immune Network, 2010, 10(1):1-4.
Narasimhan et al., "High-dose monoclonal antibodies via the subcutaneous route: challenges and technical solutions, an industry perspective," Therapeutic Delivery, 2012, 3(7):889-900.
Oppmann et al., Novel p19 Protein Engages IL-12p40 to Form a Cytokine, IL-23, with Biological Activities Similar as Well as Distinct from IL-12,$201D Immunity, 2000, 13:715-725.
Papp et al., "Tildrakizumab (MK-3222) an anti-interleukin-23p19 monoclonal antibody, improves psoriasis in a phase IIb randomized placebo-controlled trial," British Journal of Dermatology, 2015, 173:930-939.
Parham et al., "A Receptor for the Heterodimeric Cytokine IL-23 is Composed of IL-12Rβ1 and a Novel Cytokine Receptor Subunit, IL-23R," Journal of Immunology, 2002, 168:5699-5708.
Patel et al., "Emerging Therapies for the Treatment of Psoriasis" Dermatol Ther. (Heidelb), 2012, 2:16, 10 pages.
Paul, William E., M.D., Fundamental Immunology, 3rd Ed., Raven Press, New York, Chapter 8, 1993, 292-295.
Pirhonen et al., "Regulation of Virus-Induced IL-12 and IL-23 Expression in Human Macrophages," Journal of Immunology, 2002, 5673-5678.
Piskin et al., "Clinical Improvement in chronic plaque-type psoriasis lesions after narrow-band UVB therapy is accompanied by a decrease in the expression of IFN-y inducers—IL-12, IL-18, and IL-23," Experimental Dermatology, 2004, 13:764-772.
Piskin, Gamze "IL-23 Expression by Keratinocytes," Effects of Therapies on Cytokine Patterns of Psoriasis, 2004, Chapter 7, 114-131.
R&D Systems New Products, Jun. 2005. 12 pgs. www.RnDSystems.com.
R&D Systems, de novo newsletter, Mar. 2004, 10 pgs. www.rndsystems.com.
Rouet et al., "Stability engineering of the human antibody repertoire," FEBS Letters, 2014, 588:269-277.
Sands et al., "A randomized, double-blind placebo-controlled phase 2a induction study of MEDI2070 (anti-p19 antibody) in patients with active Crohn's disease who have failed anti-TNF antibody therapy," Journal of Crohn's and Colitis, Feb. 1, 2015, 9(Supp_1):S15-S16, OP025.
Savage et al. "Ustekinumab in the Treatment of Psoriasis and Psoriatic Arthritis," Rheumatol. Ther., 2015, 2:1-16.
Sehy et al., Abstract 560.34 "Unambiguous Detection of IL-23 (p19/p40) Protein in Native Samples Using a Novel Enzyme-Linked Immunosorbent Assay," Experimental Biology, 2005, A945-A946, International Congress of Physiological Sciences.
Shire, Steven J., Monoclonal Antibodies: Meeting the Challenges in Manufacturing, Formulation, Delivery and Stability of Final Drug Product, 2015.
Singh et al., "Selective targeting of the IL23 pathway: Generation and characterization of a novel high-affinity humanized anti-IL23A antibody," MABS, Apr. 23, 2015, 7(4):778-791.
Sofen et al., "Guselkumab (an IL-23-specific mAb) demonstrates clinical and molecular response in patients iwth moderate-to-severe psoriasis," Journal of Allergy and Clinical Immunology, 2014,133:1032-1040.
Suarez-Farinas et al., "Expanding the Psoriasis Disease Profile: Interrogation of the Skin and Serum of Patients with Moderate-to-Severe Psoriasis," Journal of Investigative Dermatology, 2012, 132:2552-2564.
Tian et al., "Meta-Analysis Derived (MAD) Transcriptome of Psoriasis Defines the "Core" Patheogenesis of Disease," PLOS One, 2012, 7(9):e44274, 15 pages.
U.S. Appl. No. 13/870,061, filed Apr. 25, 2013. First named inventor: Gerald Henry Nabozny. (The cited pending U.S. application is stored in the USPTO IFW system (MPEP 609.4(a)(II)(C)).
U.S. Appl. No. 14/302,986, filed Jun. 12, 2014. First named inventor: Rachel Rebecca Barrett. (The cited pending U.S. application is stored in the USPTO IFW system (MPEP 609.4(a)(II)(C)).
Vajdos et al., "Comprehensive Functional Maps of the Antigen-binding Site of an Anti-ErbB2 Antibody Obtained with Shotgun Scanning Mutagenesis," J. Mol. Biol., 2002, 320:415-428.
Verreck et al., "Human IL-23-producing type 1 macrophages promote but IL-10 producing type 2 macrophages subvert immunity to (myco)bacteria," PNAS, 2004, 101(13):4560-4565.
Wakashin et al., "IL-23 and Th17 Cells Enhance Th2-Cell-mediated Eosinophilic Airway Inflammation in MIce" American Journal of Respiratory and Critical Care Medicine, 2008, 178:1023-1032.
Wang et al,. "Antibody Structure, Instability, and Formulation," Journal of Pharmaceutical Sciences, Jan. 1, 2007, 96(1):1-26.
Wang et al., Aggregation of Therapeutic Proteins, 2010.
Wang, Wei, "Review: Instability, stabilization, and formulation of liquid protein pharmaceuticals," International Journal of Pharmaceutics, 1999, 185:129-188.

(56) References Cited

OTHER PUBLICATIONS

Wenzel, Sally, "Severe asthma: from characteristics to phenotypes to endotypes," Clinical & Experimental Allergy, 2012, 42:650-658.
Wikipedia entry for "Guselkumab," 5 pages, downloaded May 29, 2018.
Woodle et al., "Phase I Trial of a Humanized, Fc Receptor Non-binding OKT3 Antibody, huOKT3γ1(Ala-Ala) In the Treatment of Acute Renal Allograft Rejection," Transplantation, 1999, 68(5):608-616.
Written Opinion dated Aug. 17, 2017, in PCT/US2016/016061.
Yeilding et al., "Development of the IL-12/23 antagonist ustekinumab in psoriasis: past, present and future perspectives," Annals of the New York Academy of Sciences, 2011, 1222:30-39.
Zakharova et al., "Paradoxical Anti-Inflammatory Actions of TNF-a: Inhibition of IL-12 and IL-23 via TNF Receptor 1 in Macrophages and Dendritic Cells" Journal of Immunology, 2005, 175:5024-5033.

\* cited by examiner

Anti-IL-23p19 6B8 Engineered Vk regions

```
                                                                                          Chothia-----         Chothia
                                                                                          Kabat------         Kabat--
                                                                                          IMGT--              IMGT
>6B8-Vk      DIVMTQSHKFLSTSVGDRVTITCKASRDVAIAVAWYQQKPGQSPKLLLFWASTRHT
>Hum Vk#65   DIQMTQSPSSLSASVGDRVTITCKASRDVAIAVAWYQQKPGKVPKLLIYWASTRHT
>Hum Vk#66   DIQMTQSPSSLSASVGDRVTITCKASRDVAIAVAWYQQKPGKVPKLLIYWASTRHT
>Hum Vk#67   DIQMTQSPSSLSASVGDRVTITCKASRDVAIAVAWYQQKPGKVPKLLLYWASTRHT
>Hum Vk#78   DIQMTQSPSSLSASVGDRVTITCKASRDVAIAVAWYQQKPGKVPKLLLFWASTRHT Chothia--
                                                                   Kabat-----
                                                                   IMGT------
>6B8-Vk      GVPDRFTGSGSRTDFTLTISNVQSEDLADYFCHQYSSYPFTFGSGTKLEIK    (SEQ ID NO:86)
>Hum Vk#65   GVPDRFSGSGSGTDFTLTISSLQPEDLADYCHQYSSYPFTFGQGTKLEIK    (SEQ ID NO:158)
>Hum Vk#66   GVPSRFSGSGSRTDFTLTISSLQPEDVADYFCHQYSSYPFTFGSGTKLEIK   (SEQ ID NO:160)
>Hum Vk#67   GVPSRFSGSGSRTDFTLTISSLQPEDVATYYCHQYSSYPFTFGSGTKLEIK   (SEQ ID NO:162)
>Hum Vk#78   GVPDRFSGSGSRTDFTLTISSLQPEDLADYCHQYSSYPFTFGSGTKLEIK    (SEQ ID NO:164)
```

FIG. 1A

Anti-IL-23p19 6B8 Engineered VH regions

```
                                                              Chothia- - - -                      Chothia- - -
                                                                      Kabat                               Kabat- - - - - -
                                                                          IMGT- - - -                              IMGT- - - -
>6B8-VH     QVQLQQSDAELVKPGTSVKTSCKISGNTFTDQTIHWMKQRPEQGLEWIGYIYPRDDSPKY
>Hum VH#2   QVQLVQSGAEVVKPGTSVKVSCKASGYTFTDQTIHWMRQAPGQGLEWIGYIYPRDDSPKY
>Hum VH#5   QVQLVQSGAEVVKPGTSVKVSCKASG[F]TFTDQTIHWVRQAPGQGLEWMGYIYPRDDSPKY
>Hum VH#36  QVQLVQSGAEVVKPGTSVKTSCKASGGTFTFTDQTIHWVRQRPGQGLEWMGYIYPRDDSPKY
>Hum VH#65  QVQLVQSGAEVVKPGTSVKVSCKASGGTFTFTDQTIHWVRQAPGQGLEWMGYIYPRDDSPKY Chothia- - - -                              Chothia- - -
                    Kabat-                                              Kabat- - - - - -
                                                                                IMGT- - - - - - -
>6B8-VH     NENFKGKATLTADKSSSTAYMQLNSLTSEDSAVYFCAIPDRSGYAWFIYWGQGTLVTVSS  (SEQ ID NO:123)
>Hum VH#2   NENFKGKVTITADKSTSTAYMELSSLRSEDTAVYYCAIPDRSGYAWFIYWGQGTLVTVSS  (SEQ ID NO:166)
>Hum VH#5   NENFKGKVTLTADKSTSTAYMELSSLRSEDTAVYYCAIPDRSGYAWFIYWGQGTLVTVSS  (SEQ ID NO:168)
>Hum VH#36  NENFKGKVTITADKSTSTAYMELSSLRSEDTAVYYCAIPDRSGYAWFIYWGQGTLVTVSS  (SEQ ID NO:170)
>Hum VH#65  NENFKGKVTLTADKSTSTAYMELSSLRSEDTAVYFCARPDRSGYAWFIYWGQGTLVTVSS  (SEQ ID NO:172)
```

FIG. 1B

SEQUENCE LISTING

<160> NUMBER OF SEQ ID NOS: 181

<210> SEQ ID NO 1
<211> LENGTH: 11
<212> TYPE: PRT
<213> ORGANISM: Mouse

<400> SEQUENCE: 1

Arg Ala Ser Gln Ser Ile Ser Glu Tyr Leu His
 1               5                  10

<210> SEQ ID NO 2
<211> LENGTH: 7
<212> TYPE: PRT
<213> ORGANISM: Mouse

<400> SEQUENCE: 2

Tyr Ala Ser Gln Ser Ile Ser
 1               5

<210> SEQ ID NO 3
<211> LENGTH: 9
<212> TYPE: PRT
<213> ORGANISM: Mouse

<400> SEQUENCE: 3

Gln Asn Gly His Ser Phe Pro Phe Thr
 1               5

<210> SEQ ID NO 4
<211> LENGTH: 11
<212> TYPE: PRT
<213> ORGANISM: Mouse

<400> SEQUENCE: 4

Arg Ala Ser Gln Ser Ile Ser Asp Tyr Leu Tyr
 1               5                  10

<210> SEQ ID NO 5
<211> LENGTH: 7
<212> TYPE: PRT
<213> ORGANISM: Mouse

<400> SEQUENCE: 5

Phe Ala Ser Gln Ser Ile Ser
 1               5

<210> SEQ ID NO 6
<211> LENGTH: 11
<212> TYPE: PRT
<213> ORGANISM: Mouse

<400> SEQUENCE: 6

Arg Ala Ser Gln Ser Ile Ser Val Tyr Leu His
 1               5                  10

<210> SEQ ID NO 7
<211> LENGTH: 11
<212> TYPE: PRT
<213> ORGANISM: Mouse

<400> SEQUENCE: 7

Arg Ala Ser Gln Ser Ile Ser Asp Tyr Leu His
 1               5                  10

```
<210> SEQ ID NO 8
<211> LENGTH: 16
<212> TYPE: PRT
<213> ORGANISM: Mouse

<400> SEQUENCE: 8

Arg Ser Ser Gln Ser Leu Val His Ser Asn Gly Asn Thr Tyr Leu His
 1               5                  10                  15

<210> SEQ ID NO 9
<211> LENGTH: 7
<212> TYPE: PRT
<213> ORGANISM: Mouse

<400> SEQUENCE: 9

Lys Val Ser Asn Arg Phe Ser
 1               5

<210> SEQ ID NO 10
<211> LENGTH: 9
<212> TYPE: PRT
<213> ORGANISM: Mouse

<400> SEQUENCE: 10

Ser Gln Ser Thr His Val Pro Tyr Thr
 1               5

<210> SEQ ID NO 11
<211> LENGTH: 15
<212> TYPE: PRT
<213> ORGANISM: Mouse

<400> SEQUENCE: 11

Arg Ala Ser Lys Ser Val Ser Thr Ser Gly Tyr Ser Tyr Ile His
 1               5                  10                  15

<210> SEQ ID NO 12
<211> LENGTH: 7
<212> TYPE: PRT
<213> ORGANISM: Mouse

<400> SEQUENCE: 12

Leu Ala Ser Asn Leu Asp Ser
 1               5

<210> SEQ ID NO 13
<211> LENGTH: 9
<212> TYPE: PRT
<213> ORGANISM: Mouse

<400> SEQUENCE: 13

Gln His Ser Arg Glu Leu Pro Tyr Thr
 1               5

<210> SEQ ID NO 14
<211> LENGTH: 9
<212> TYPE: PRT
<213> ORGANISM: Mouse

<400> SEQUENCE: 14

Gln Asn Gly His Ser Phe Pro Tyr Thr
 1               5

<210> SEQ ID NO 15
```

```
<211> LENGTH: 15
<212> TYPE: PRT
<213> ORGANISM: Mouse

<400> SEQUENCE: 15

Arg Thr Ser Glu Ser Val Tyr Ser Tyr Gly Gln Asn Phe Ile His
1               5                   10                  15

<210> SEQ ID NO 16
<211> LENGTH: 7
<212> TYPE: PRT
<213> ORGANISM: Mouse

<400> SEQUENCE: 16

Arg Ala Ser Asn Leu Glu Ser
1               5

<210> SEQ ID NO 17
<211> LENGTH: 9
<212> TYPE: PRT
<213> ORGANISM: Mouse

<400> SEQUENCE: 17

Gln Gln Thr Asn Glu Asp Pro Tyr Thr
1               5

<210> SEQ ID NO 18
<211> LENGTH: 15
<212> TYPE: PRT
<213> ORGANISM: Mouse

<400> SEQUENCE: 18

Arg Ala Ser Glu Thr Ile Asn Phe Tyr Gly Thr Ser Phe Met His
1               5                   10                  15

<210> SEQ ID NO 19
<211> LENGTH: 11
<212> TYPE: PRT
<213> ORGANISM: Mouse

<400> SEQUENCE: 19

Lys Ala Ser Arg Asp Val Ala Ile Ala Val Ala
1               5                   10

<210> SEQ ID NO 20
<211> LENGTH: 7
<212> TYPE: PRT
<213> ORGANISM: Mouse

<400> SEQUENCE: 20

Trp Ala Ser Thr Arg His Thr
1               5

<210> SEQ ID NO 21
<211> LENGTH: 9
<212> TYPE: PRT
<213> ORGANISM: Mouse

<400> SEQUENCE: 21

His Gln Tyr Ser Ser Tyr Pro Phe Thr
1               5

<210> SEQ ID NO 22
<211> LENGTH: 11
<212> TYPE: PRT
```

<213> ORGANISM: Mouse

<400> SEQUENCE: 22

Arg Ala Ser Glu Asn Ile Asp Ser Tyr Leu Ala
1               5                   10

<210> SEQ ID NO 23
<211> LENGTH: 7
<212> TYPE: PRT
<213> ORGANISM: Mouse

<400> SEQUENCE: 23

Ala Ala Arg Asn Leu Ala Asp
1               5

<210> SEQ ID NO 24
<211> LENGTH: 9
<212> TYPE: PRT
<213> ORGANISM: Mouse

<400> SEQUENCE: 24

Gln His Tyr Tyr Ser Thr Pro Phe Thr
1               5

<210> SEQ ID NO 25
<211> LENGTH: 7
<212> TYPE: PRT
<213> ORGANISM: Mouse

<400> SEQUENCE: 25

Ala Ala Thr Asn Leu Ala Asp
1               5

<210> SEQ ID NO 26
<211> LENGTH: 9
<212> TYPE: PRT
<213> ORGANISM: Mouse

<400> SEQUENCE: 26

Leu His Tyr Tyr Ser Thr Pro Phe Thr
1               5

<210> SEQ ID NO 27
<211> LENGTH: 15
<212> TYPE: PRT
<213> ORGANISM: Mouse

<400> SEQUENCE: 27

Arg Ala Ser Lys Ser Val Arg Phe Ser Asp Tyr Phe Tyr Met His
1               5                   10                  15

<210> SEQ ID NO 28
<211> LENGTH: 7
<212> TYPE: PRT
<213> ORGANISM: Mouse

<400> SEQUENCE: 28

Leu Ala Ser Asn Leu Glu Ser
1               5

<210> SEQ ID NO 29
<211> LENGTH: 9
<212> TYPE: PRT
<213> ORGANISM: Mouse

```
<400> SEQUENCE: 29

Gln Asn Ser Arg Glu Leu Pro Tyr Thr
1               5

<210> SEQ ID NO 30
<211> LENGTH: 11
<212> TYPE: PRT
<213> ORGANISM: Mouse

<400> SEQUENCE: 30

Lys Ala Ser Gln Asp Val Gly Asn Ala Val Val
1               5                   10

<210> SEQ ID NO 31
<211> LENGTH: 7
<212> TYPE: PRT
<213> ORGANISM: Mouse

<400> SEQUENCE: 31

Trp Ala Ser Thr Arg His Ile
1               5

<210> SEQ ID NO 32
<211> LENGTH: 8
<212> TYPE: PRT
<213> ORGANISM: Mouse

<400> SEQUENCE: 32

Gln Gln Tyr Ser Ser Tyr Leu Thr
1               5

<210> SEQ ID NO 33
<211> LENGTH: 10
<212> TYPE: PRT
<213> ORGANISM: Mouse

<400> SEQUENCE: 33

Gly Tyr Thr Phe Thr Ser Ser Val Ile His
1               5                   10

<210> SEQ ID NO 34
<211> LENGTH: 17
<212> TYPE: PRT
<213> ORGANISM: Mouse

<400> SEQUENCE: 34

Tyr Ile Asn Pro Tyr Asn Asp Gly Thr Lys Tyr Asn Glu Lys Phe Lys
1               5                   10                  15

Gly

<210> SEQ ID NO 35
<211> LENGTH: 6
<212> TYPE: PRT
<213> ORGANISM: Mouse

<400> SEQUENCE: 35

Arg Leu Asp Glu Ala Tyr
1               5

<210> SEQ ID NO 36
<211> LENGTH: 10
<212> TYPE: PRT
<213> ORGANISM: Mouse
```

```
<400> SEQUENCE: 36

Gly Tyr Thr Phe Thr Arg Tyr Leu Ile His
1               5                   10

<210> SEQ ID NO 37
<211> LENGTH: 6
<212> TYPE: PRT
<213> ORGANISM: Mouse

<400> SEQUENCE: 37

Asn Trp Asp Leu Asp Tyr
1               5

<210> SEQ ID NO 38
<211> LENGTH: 10
<212> TYPE: PRT
<213> ORGANISM: Mouse

<400> SEQUENCE: 38

Gly Tyr Thr Phe Thr Ser Ser Val Met His
1               5                   10

<210> SEQ ID NO 39
<211> LENGTH: 17
<212> TYPE: PRT
<213> ORGANISM: Mouse

<400> SEQUENCE: 39

Tyr Ile Asn Pro Tyr Asn Asp Gly Thr Gln Tyr Asn Glu Lys Phe Lys
1               5                   10                  15

Gly

<210> SEQ ID NO 40
<211> LENGTH: 10
<212> TYPE: PRT
<213> ORGANISM: Mouse

<400> SEQUENCE: 40

Gly Tyr Thr Phe Thr Ser Ser Ile Ile His
1               5                   10

<210> SEQ ID NO 41
<211> LENGTH: 17
<212> TYPE: PRT
<213> ORGANISM: Mouse

<400> SEQUENCE: 41

Tyr Ile Asn Pro Tyr Asp Asp Val Thr Lys Tyr Asn Glu Lys Phe Lys
1               5                   10                  15

Gly

<210> SEQ ID NO 42
<211> LENGTH: 6
<212> TYPE: PRT
<213> ORGANISM: Mouse

<400> SEQUENCE: 42

Arg Trp Asp Glu Ser Tyr
1               5

<210> SEQ ID NO 43
<211> LENGTH: 10
<212> TYPE: PRT
```

```
<213> ORGANISM: Mouse

<400> SEQUENCE: 43

Gly Tyr Thr Phe Thr Thr Ser Ile Met His
1               5                   10

<210> SEQ ID NO 44
<211> LENGTH: 6
<212> TYPE: PRT
<213> ORGANISM: Mouse

<400> SEQUENCE: 44

Arg Trp Asp Glu Ala Tyr
1               5

<210> SEQ ID NO 45
<211> LENGTH: 10
<212> TYPE: PRT
<213> ORGANISM: Mouse

<400> SEQUENCE: 45

Gly Tyr Thr Phe Thr Asp Tyr Tyr Met Asn
1               5                   10

<210> SEQ ID NO 46
<211> LENGTH: 17
<212> TYPE: PRT
<213> ORGANISM: Mouse

<400> SEQUENCE: 46

Val Ile Ile Pro Tyr Asn Gly Gly Thr Ser Tyr Asn Gln Lys Phe Lys
1               5                   10                  15

Gly

<210> SEQ ID NO 47
<211> LENGTH: 9
<212> TYPE: PRT
<213> ORGANISM: Mouse

<400> SEQUENCE: 47

Asp Gly His Arg Trp Tyr Phe Asp Val
1               5

<210> SEQ ID NO 48
<211> LENGTH: 10
<212> TYPE: PRT
<213> ORGANISM: Mouse

<400> SEQUENCE: 48

Gly Tyr Ser Phe Thr Gly Tyr Tyr Met Asn
1               5                   10

<210> SEQ ID NO 49
<211> LENGTH: 17
<212> TYPE: PRT
<213> ORGANISM: Mouse

<400> SEQUENCE: 49

Glu Ile Ile Pro Thr Thr Gly Thr Ser Tyr Asn Gln Lys Phe Lys
1               5                   10                  15

Ala

<210> SEQ ID NO 50
```

```
<211> LENGTH: 11
<212> TYPE: PRT
<213> ORGANISM: Mouse

<400> SEQUENCE: 50

Glu Ser Gly Gly Phe Tyr Trp Tyr Phe Asp Val
1               5                   10

<210> SEQ ID NO 51
<211> LENGTH: 10
<212> TYPE: PRT
<213> ORGANISM: Mouse

<400> SEQUENCE: 51

Gly Tyr Thr Phe Thr Asp His Thr Ile His
1               5                   10

<210> SEQ ID NO 52
<211> LENGTH: 17
<212> TYPE: PRT
<213> ORGANISM: Mouse

<400> SEQUENCE: 52

Tyr Ile Tyr Pro Arg Asp Gly Tyr Pro Lys Phe Asn Glu Lys Phe Lys
1               5                   10                  15

Gly

<210> SEQ ID NO 53
<211> LENGTH: 9
<212> TYPE: PRT
<213> ORGANISM: Mouse

<400> SEQUENCE: 53

Arg Pro Pro Tyr Tyr Ala Met Asp Tyr
1               5

<210> SEQ ID NO 54
<211> LENGTH: 10
<212> TYPE: PRT
<213> ORGANISM: Mouse

<400> SEQUENCE: 54

Gly Tyr Thr Phe Thr Arg Tyr Leu Met His
1               5                   10

<210> SEQ ID NO 55
<211> LENGTH: 17
<212> TYPE: PRT
<213> ORGANISM: Mouse

<400> SEQUENCE: 55

Tyr Ile Asn Pro Tyr Asn Asp Gly Thr Asn Tyr Asn Glu Lys Phe Lys
1               5                   10                  15

Gly

<210> SEQ ID NO 56
<211> LENGTH: 6
<212> TYPE: PRT
<213> ORGANISM: Mouse

<400> SEQUENCE: 56

Asn Trp Asp Tyr Ala Tyr
1               5
```

<210> SEQ ID NO 57
<211> LENGTH: 10
<212> TYPE: PRT
<213> ORGANISM: Mouse

<400> SEQUENCE: 57

Gly Phe Ser Leu Thr Thr Tyr Ala Ile Ser
1               5                   10

<210> SEQ ID NO 58
<211> LENGTH: 16
<212> TYPE: PRT
<213> ORGANISM: Mouse

<400> SEQUENCE: 58

Val Ile Trp Thr Gly Gly Gly Thr Lys Tyr Asn Ser Ala Leu Lys Ser
1               5                   10                  15

<210> SEQ ID NO 59
<211> LENGTH: 11
<212> TYPE: PRT
<213> ORGANISM: Mouse

<400> SEQUENCE: 59

Lys Asp Tyr Asn Tyr Gly Gly Ala Met Asp Tyr
1               5                   10

<210> SEQ ID NO 60
<211> LENGTH: 10
<212> TYPE: PRT
<213> ORGANISM: Mouse

<400> SEQUENCE: 60

Gly Phe Ser Leu Asn Asn Phe Ala Ile Ser
1               5                   10

<210> SEQ ID NO 61
<211> LENGTH: 16
<212> TYPE: PRT
<213> ORGANISM: Mouse

<400> SEQUENCE: 61

Ala Ile Trp Thr Gly Gly Gly Thr Asn Tyr Asn Ser Ala Leu Lys Ser
1               5                   10                  15

<210> SEQ ID NO 62
<211> LENGTH: 11
<212> TYPE: PRT
<213> ORGANISM: Mouse

<400> SEQUENCE: 62

Lys Asp Tyr Ser Tyr Gly Gly Ala Met Asp Tyr
1               5                   10

<210> SEQ ID NO 63
<211> LENGTH: 10
<212> TYPE: PRT
<213> ORGANISM: Mouse

<400> SEQUENCE: 63

Gly Asn Thr Phe Thr Asp Gln Thr Ile His
1               5                   10

<210> SEQ ID NO 64

```
<211> LENGTH: 17
<212> TYPE: PRT
<213> ORGANISM: Mouse

<400> SEQUENCE: 64

Tyr Ile Tyr Pro Arg Asp Asp Ser Pro Lys Tyr Asn Glu Asn Phe Lys
1               5                   10                  15

Gly

<210> SEQ ID NO 65
<211> LENGTH: 11
<212> TYPE: PRT
<213> ORGANISM: Mouse

<400> SEQUENCE: 65

Pro Asp Arg Ser Gly Tyr Ala Trp Phe Ile Tyr
1               5                   10

<210> SEQ ID NO 66
<211> LENGTH: 10
<212> TYPE: PRT
<213> ORGANISM: Artificial Sequence
<220> FEATURE:
<223> OTHER INFORMATION: Humanized sequence.

<400> SEQUENCE: 66

Gly Tyr Thr Phe Thr Asp Gln Thr Ile His
1               5                   10

<210> SEQ ID NO 67
<211> LENGTH: 10
<212> TYPE: PRT
<213> ORGANISM: Artificial Sequence
<220> FEATURE:
<223> OTHER INFORMATION: Humanized sequence.

<400> SEQUENCE: 67

Gly Phe Thr Phe Thr Asp Gln Thr Ile His
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Humanized sequence.

<400> SEQUENCE: 68

Gly Gly Thr Phe Thr Asp Gln Thr Ile His
1               5                   10

<210> SEQ ID NO 69
<211> LENGTH: 10
<212> TYPE: PRT
<213> ORGANISM: Mouse

<400> SEQUENCE: 69

Gly Tyr Thr Phe Thr Arg Tyr Val Met His
1               5                   10

<210> SEQ ID NO 70
<211> LENGTH: 17
<212> TYPE: PRT
<213> ORGANISM: Mouse

<400> SEQUENCE: 70
```

```
Tyr Ile Asn Pro Tyr Asn Asp Val Thr Lys Tyr Asn Glu Lys Phe Lys
1               5                   10                  15

Gly

<210> SEQ ID NO 71
<211> LENGTH: 6
<212> TYPE: PRT
<213> ORGANISM: Mouse

<400> SEQUENCE: 71

Asn Trp Asp Val Pro Tyr
1               5

<210> SEQ ID NO 72
<211> LENGTH: 17
<212> TYPE: PRT
<213> ORGANISM: Mouse

<400> SEQUENCE: 72

Tyr Ile Asn Pro Tyr Asn Asp Gly Thr Lys Tyr Asn Glu Arg Phe Lys
1               5                   10                  15

Gly

<210> SEQ ID NO 73
<211> LENGTH: 17
<212> TYPE: PRT
<213> ORGANISM: Mouse

<400> SEQUENCE: 73

Val Ile Ile Pro Tyr Asn Gly Gly Ile Ser Tyr Asn Gln Lys Phe Lys
1               5                   10                  15

Gly

<210> SEQ ID NO 74
<211> LENGTH: 9
<212> TYPE: PRT
<213> ORGANISM: Mouse

<400> SEQUENCE: 74

Asn Asp Tyr Asp Trp Tyr Phe Asp Val
1               5

<210> SEQ ID NO 75
<211> LENGTH: 17
<212> TYPE: PRT
<213> ORGANISM: Mouse

<400> SEQUENCE: 75

Asp Phe Asn His Asn Asn Asp Val Ile Thr Tyr Asn Pro Lys Phe Lys
1               5                   10                  15

Gly

<210> SEQ ID NO 76
<211> LENGTH: 10
<212> TYPE: PRT
<213> ORGANISM: Mouse

<400> SEQUENCE: 76

Gly Leu Arg Gly Tyr Tyr Ala Met Asp Tyr
1               5                   10
```

```
<210> SEQ ID NO 77
<211> LENGTH: 10
<212> TYPE: PRT
<213> ORGANISM: Mouse

<400> SEQUENCE: 77

Gly Tyr Ser Phe Thr Asp Tyr Asn Met Asn
 1               5                  10

<210> SEQ ID NO 78
<211> LENGTH: 17
<212> TYPE: PRT
<213> ORGANISM: Mouse

<400> SEQUENCE: 78

Val Ile Ile Pro Asn Tyr Gly Phe Thr Ser Tyr Asn Gln Asn Phe Lys
 1               5                  10                  15
Gly

<210> SEQ ID NO 79
<211> LENGTH: 11
<212> TYPE: PRT
<213> ORGANISM: Mouse

<400> SEQUENCE: 79

Asp Gly Gly Ile Leu Leu Trp Tyr Leu Asp Val
 1               5                  10

<210> SEQ ID NO 80
<211> LENGTH: 10
<212> TYPE: PRT
<213> ORGANISM: Mouse

<400> SEQUENCE: 80

Gly Tyr Thr Phe Thr Asp Tyr Asn Met Asp
 1               5                  10

<210> SEQ ID NO 81
<211> LENGTH: 17
<212> TYPE: PRT
<213> ORGANISM: Mouse

<400> SEQUENCE: 81

Asp Ile Asn Pro His Asn Gly Gly Thr Ile Tyr Asn Gln Lys Phe Lys
 1               5                  10                  15
Gly

<210> SEQ ID NO 82
<211> LENGTH: 13
<212> TYPE: PRT
<213> ORGANISM: Mouse

<400> SEQUENCE: 82

Asn Tyr Tyr Gly Ser Ser Tyr Gly Trp Tyr Phe Asp Val
 1               5                  10

<210> SEQ ID NO 83
<211> LENGTH: 333
<212> TYPE: DNA
<213> ORGANISM: Mouse

<400> SEQUENCE: 83
gacattgtgc tgacccaatc tccaggttct ttggctgtgt ctctagggca gagggccacc    60
```

```
atatcctgca gaaccagtga aagtgtttat agttatggcc aaaattttat acactggtac    120
cagcagaaac caggacagcc acccaaactc ctcatctatc gtgcatccaa cctggaatct    180
gggatccctg ccaggttcag tggcagtggg tctaggacag acttcaccct caccatgaat    240
cctgtggagg ctgatgatgt tgcaacctat tactgtcagc aaactaatga ggatccgtac    300
acgttcggag gggggaccaa gctggaaata aga                                333
```

<210> SEQ ID NO 84
<211> LENGTH: 111
<212> TYPE: PRT
<213> ORGANISM: Mouse

<400> SEQUENCE: 84

```
Asp Ile Val Leu Thr Gln Ser Pro Gly Ser Leu Ala Val Ser Leu Gly
 1               5                  10                  15

Gln Arg Ala Thr Ile Ser Cys Arg Thr Ser Glu Ser Val Tyr Ser Tyr
             20                  25                  30

Gly Gln Asn Phe Ile His Trp Tyr Gln Gln Lys Pro Gly Gln Pro Pro
         35                  40                  45

Lys Leu Leu Ile Tyr Arg Ala Ser Asn Leu Glu Ser Gly Ile Pro Ala
     50                  55                  60

Arg Phe Ser Gly Ser Gly Ser Arg Thr Asp Phe Thr Leu Thr Met Asn
 65                  70                  75                  80

Pro Val Glu Ala Asp Asp Val Ala Thr Tyr Tyr Cys Gln Gln Thr Asn
                 85                  90                  95

Glu Asp Pro Tyr Thr Phe Gly Gly Gly Thr Lys Leu Glu Ile Arg
            100                 105                 110
```

<210> SEQ ID NO 85
<211> LENGTH: 321
<212> TYPE: DNA
<213> ORGANISM: Mouse

<400> SEQUENCE: 85

```
gacattgtga tgacccagtc tcacaaattc ttgtccacat cagtgggaga cagggtcacc     60
atcacttgca aggccagtcg ggatgtggct attgctgtag cctggtatca acagaaacca    120
gggcaatctc ctaaactact tctttttctgg gcatccaccc gacacactgg ggtccctgat    180
cgcttcacag gcagtggatc tcggacagat ttcactctca ccattagcaa tgtgcagtct    240
gaagacttgg cagattattt ctgtcaccaa tatagcagct atccattcac gttcggctcg    300
gggacaaagt tggaaataaa g                                              321
```

<210> SEQ ID NO 86
<211> LENGTH: 107
<212> TYPE: PRT
<213> ORGANISM: Mouse

<400> SEQUENCE: 86

```
Asp Ile Val Met Thr Gln Ser His Lys Phe Leu Ser Thr Ser Val Gly
 1               5                  10                  15

Asp Arg Val Thr Ile Thr Cys Lys Ala Ser Arg Asp Val Ala Ile Ala
             20                  25                  30

Val Ala Trp Tyr Gln Gln Lys Pro Gly Gln Ser Pro Lys Leu Leu Leu
         35                  40                  45

Phe Trp Ala Ser Thr Arg His Thr Gly Val Pro Asp Arg Phe Thr Gly
     50                  55                  60
```

```
Ser Gly Ser Arg Thr Asp Phe Thr Leu Thr Ile Ser Asn Val Gln Ser
 65                  70                  75                  80

Glu Asp Leu Ala Asp Tyr Phe Cys His Gln Tyr Ser Ser Tyr Pro Phe
                 85                  90                  95

Thr Phe Gly Ser Gly Thr Lys Leu Glu Ile Lys
                100                 105
```

<210> SEQ ID NO 87
<211> LENGTH: 333
<212> TYPE: DNA
<213> ORGANISM: Mouse

<400> SEQUENCE: 87

```
gacattgcgc tgacccaatc tccagcttct ttggctgtgt ctctgggggca gagggccacc    60
atatcctgca gagccagtga aactattaat ttttatggca ctagttttat gcactggtac   120
cagcagaaac aggacagtc acccaaactc ctcatctatc gtgcatccaa cctagaatct    180
gggatccctg ccaggttcag tgcagtgggg tctaggacag acttcaccct caccattaat   240
cctgtggagg ctgatgatgt tgcaacctat tactgtcagc aaactaatga ggatccgtac   300
acgttcggag gggggactaa gttggaaata aaa                                333
```

<210> SEQ ID NO 88
<211> LENGTH: 111
<212> TYPE: PRT
<213> ORGANISM: Mouse

<400> SEQUENCE: 88

```
Asp Ile Ala Leu Thr Gln Ser Pro Ala Ser Leu Ala Val Ser Leu Gly
  1               5                  10                  15

Gln Arg Ala Thr Ile Ser Cys Arg Ala Ser Glu Thr Ile Asn Phe Tyr
                 20                  25                  30

Gly Thr Ser Phe Met His Trp Tyr Gln Gln Lys Pro Gly Gln Ser Pro
             35                  40                  45

Lys Leu Leu Ile Tyr Arg Ala Ser Asn Leu Glu Ser Gly Ile Pro Ala
 50                  55                  60

Arg Phe Ser Gly Ser Gly Ser Arg Thr Asp Phe Thr Leu Thr Ile Asn
 65                  70                  75                  80

Pro Val Glu Ala Asp Asp Val Ala Thr Tyr Tyr Cys Gln Gln Thr Asn
                 85                  90                  95

Glu Asp Pro Tyr Thr Phe Gly Gly Gly Thr Lys Leu Glu Ile Lys
                100                 105                 110
```

<210> SEQ ID NO 89
<211> LENGTH: 336
<212> TYPE: DNA
<213> ORGANISM: Mouse

<400> SEQUENCE: 89

```
gatgttgtga tgacccaaac tccactctcc ctgcctgtca gtcttggaga tcaagcctcc    60
atctcttgca gatctagtca gagccttgta cacagtaatg gaaacaccta tttacattgg   120
tacctgcaga agccaggcca gtctccaaag ctcctgatct acaaagtttc caaccgattt   180
tctggggtcc cagacaggtt cagtggcagt ggatcaggga cagatttcac actcaagatc   240
aacagagtgg aggctgagga tctgggagtt tatttctgct ctcaaagtac acatgttccg   300
tacacgttcg gaggggggac cagctggaa ataaaa                              336
```

```
<210> SEQ ID NO 90
<211> LENGTH: 112
<212> TYPE: PRT
<213> ORGANISM: Mouse

<400> SEQUENCE: 90

Asp Val Val Met Thr Gln Thr Pro Leu Ser Leu Pro Val Ser Leu Gly
 1               5                  10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Asn Arg Val Glu Ala Glu Asp Leu Gly Val Tyr Phe Cys Ser Gln Ser
                85                  90                  95

Thr His Val Pro Tyr Thr Phe Gly Gly Gly Thr Gln Leu Glu Ile Lys
            100                 105                 110

<210> SEQ ID NO 91
<211> LENGTH: 107
<212> TYPE: PRT
<213> ORGANISM: Mouse

<400> SEQUENCE: 91

Asp Ile Val Met Thr Gln Ser Pro Ala Thr Leu Ser Val Thr Pro Gly
 1               5                  10                  15

Asp Arg Val Ser Leu Ser Cys Arg Ala Ser Gln Ser Ile Ser Asp Tyr
            20                  25                  30

Leu His Trp Tyr Gln Gln Arg Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Thr Ile Asn Ser Val Glu Pro
65                  70                  75                  80

Glu Asp Val Gly Val Tyr Tyr Cys Gln Asn Gly His Ser Phe Pro Phe
                85                  90                  95

Thr Phe Gly Ser Gly Thr Lys Leu Glu Ile Lys
            100                 105

<210> SEQ ID NO 92
<211> LENGTH: 321
<212> TYPE: DNA
<213> ORGANISM: Mouse

<400> SEQUENCE: 92
gacattgtga tgactcagtc tccagccacc ctgtctgtga ctccaggaga tagagtctct      60
ctttcctgca gggccagtca gagtattagc gactacttat actggtatca acaaaaatca    120
catgagtctc caaggcttct catcaaattt gcttcccaat ccatctctgg atcccctcc     180 aggttcactg gcagtggatc agggtcagat ttcactctca gtatcgacag tgtggaacct    240
gatgatgttg gagtcttttt ctgtcaaaat ggtcacagct ttccgttcac gttcggaggg    300
gggaccaagc tggaaataaa a                                              321

<210> SEQ ID NO 93
```

```
<211> LENGTH: 107
<212> TYPE: PRT
<213> ORGANISM: Mouse

<400> SEQUENCE: 93

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
                20                  25                  30

Leu Tyr Trp Tyr Gln Gln Lys Ser His Glu Ser Pro Arg Leu Leu Ile
            35                  40                  45

Lys Phe Ala Ser Gln Ser Ile Ser Gly Ile Pro Ser Arg Phe Thr Gly
        50                  55                  60

Ser Gly Ser Gly Ser Asp Phe Thr Leu Ser Ile Asp Ser Val Glu Pro
65                  70                  75                  80

Asp Asp Val Gly Val Phe Phe Cys Gln Asn Gly His Ser Phe Pro Phe
                85                  90                  95

Thr Phe Gly Gly Gly Thr Lys Leu Glu Ile Lys
            100                 105

<210> SEQ ID NO 94
<211> LENGTH: 321
<212> TYPE: DNA
<213> ORGANISM: Mouse

<400> SEQUENCE: 94
gacattgtga tgactcagtc tccagccacc ctgtctgtga ctccaggaga tagagtctct      60
ctttcctgca gggccagcca gagtattagc gagtacttac actggtatca acaaaaatca    120
catgagtctc caaggcttct catcaaatat gcttcccaat ccatctctgg atcccctcc     180 aggttcagtg gcagtggatc agggtcagat ttcactctca gtatcaacag tgtggaacct    240
gaagatgttg gagtgtatta ctgtcaaaat ggtcacagct ttccattcac gttcggctcg    300
gggacaaagt tggaaataaa a                                              321

<210> SEQ ID NO 95
<211> LENGTH: 107
<212> TYPE: PRT
<213> ORGANISM: Mouse

<400> SEQUENCE: 95

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Glu Tyr
                20                  25                  30

Leu His Trp Tyr Gln Gln Lys Ser His Glu Ser Pro Arg Leu Leu Ile
            35                  40                  45

Lys Tyr Ala Ser Gln Ser Ile Ser Gly Ile Pro Ser Arg Phe Ser Gly
        50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Phe
                85                  90                  95

Thr Phe Gly Ser Gly Thr Lys Leu Glu Ile Lys
            100                 105

<210> SEQ ID NO 96
<211> LENGTH: 321
```

```
<212> TYPE: DNA
<213> ORGANISM: Mouse

<400> SEQUENCE: 96
gacattgtga tgactcagtc tccagccacc ctgtctgtga ctccaggaga tagagtctct    60 cttcctgca gggccagcca gagtattagc gactacttat actggtatca acaaaaatca   120
catgagtctc caaggcttct catcaaattt gcttcccaat ccatctctgg atcccctcc   180 aggttcactg gcagtggatc agggtcagat ttcactctca gtatcgacag tgtgaacct   240 gatgatgttg gagtcttttt ctgtcaaaat ggtcacagct ttccgttcac gttcggaggg  300
gggaccaagc tggaaataaa a                                             321

<210> SEQ ID NO 97
<211> LENGTH: 107
<212> TYPE: PRT
<213> ORGANISM: Mouse

<400> SEQUENCE: 97

Asp Ile Val Met Thr Gln Ser Pro Ala Thr Leu Ser Val Thr Pro Gly
 1               5                  10                  15

Asp Arg Val Ser Leu Ser Cys Arg Ala Ser Gln Ser Ile Ser Asp Tyr
            20                  25                  30

Leu Tyr Trp Tyr Gln Gln Lys Ser His Glu Ser Pro Arg Leu Leu Ile
        35                  40                  45

Lys Phe Ala Ser Gln Ser Ile Ser Gly Ile Pro Ser Arg Phe Thr Gly
    50                  55                  60

Ser Gly Ser Gly Ser Asp Phe Thr Leu Ser Ile Asp Ser Val Glu Pro
65                  70                  75                  80

Asp Asp Val Gly Val Phe Phe Cys Gln Asn Gly His Ser Phe Pro Phe
                85                  90                  95

Thr Phe Gly Gly Gly Thr Lys Leu Glu Ile Lys
            100                 105

<210> SEQ ID NO 98
<211> LENGTH: 321
<212> TYPE: DNA
<213> ORGANISM: Mouse

<400> SEQUENCE: 98
gacattgtga tgactcagtc tccagccacc ctgtctgtga ctccaggaga tagagtctct    60 cttcctgca gggccagcca gagtattagc gagtatttac actggtatca acaaaaatca   120
catgagtctc caaggcttct catcaaatat gcttcccaat ccatctctgg atcccctcc   180 aggttcagtg gcagtggatc agggtcagat ttcactctca gtatcaacag tgtggaacct  240
gaagatgttg gagtttatta ctgtcaaaat ggtcacagct ttccattcac gttcggctcg  300
gggacaaagt tggaaataaa a                                             321

<210> SEQ ID NO 99
<211> LENGTH: 107
<212> TYPE: PRT
<213> ORGANISM: Mouse

<400> SEQUENCE: 99

Asp Ile Val Met Thr Gln Ser Pro Ala Thr Leu Ser Val Thr Pro Gly
 1               5                  10                  15

Asp Arg Val Ser Leu Ser Cys Arg Ala Ser Gln Ser Ile Ser Glu Tyr
            20                  25                  30
```

Leu His Trp Tyr Gln Gln Lys Ser His Glu Ser Pro Arg Leu Leu Ile
            35                  40                  45

Lys Tyr Ala Ser Gln Ser Ile Ser Gly Ile Pro Ser Arg Phe Ser Gly
        50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Phe
                85                  90                  95

Thr Phe Gly Ser Gly Thr Lys Leu Glu Ile Lys
                100                 105

<210> SEQ ID NO 100
<211> LENGTH: 321
<212> TYPE: DNA
<213> ORGANISM: Mouse

<400> SEQUENCE: 100
gacattgtga tgactcagtc tccagccacc ctgtctgtga ctccaggaga tagagtctct    60
ctctcctgca gggccagcca gagtattagc gtctacttac actggtatca acaaaaatca   120
cctgagtctc caaggcttct catcaaatat gcttcccaat ccatctctgg atcccctcc   180 aggttcagtg gcagtggatc agggtcagat ttcactctca gtatcaacag tgtggaacct   240
gaagatgttg gagtttatta ctgtcaaaat ggtcacagct ttccattcac gttcggctcg   300
gggacaaagt tggaaataaa a                                            321

<210> SEQ ID NO 101
<211> LENGTH: 107
<212> TYPE: PRT
<213> ORGANISM: Mouse

<400> SEQUENCE: 101

Asp Ile Val Met Thr Gln Ser Pro Ala Thr Leu Ser Val Thr Pro Gly
 1               5                  10                  15

Asp Arg Val Ser Leu Ser Cys Arg Ala Ser Gln Ser Ile Ser Val Tyr
            20                  25                  30

Leu His Trp Tyr Gln Gln Lys Ser Pro Glu Ser Pro Arg Leu Leu Ile
            35                  40                  45

Lys Tyr Ala Ser Gln Ser Ile Ser Gly Ile Pro Ser Arg Phe Ser Gly
        50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Phe
                85                  90                  95

Thr Phe Gly Ser Gly Thr Lys Leu Glu Ile Lys
                100                 105

<210> SEQ ID NO 102
<211> LENGTH: 321
<212> TYPE: DNA
<213> ORGANISM: Mouse

<400> SEQUENCE: 102
gacattgtga tgactcagtc tccagccacc ctgtctgtga ctccaggaaa tagagtctct    60
ctttcctgca gggccagcca gagtattagc gactacttac actggtatca acaaaaatca   120
catgagtctc caaggcttct catcaaatat gcttcccaat ccatctctgg atcccctcc   180

```
aggttcagtg gcagtggatc agggtcaaat tcactctca gtatcaacag tgtggaacct       240
gaagatgttg gagtgtatta ttgtcaaaat ggtcacagct ttccattcac gttcggctcg       300
gggacaaagt tggaaataaa a                                                  321
```

<210> SEQ ID NO 103
<211> LENGTH: 107
<212> TYPE: PRT
<213> ORGANISM: Mouse

<400> SEQUENCE: 103

```
Asp Ile Val Met Thr Gln Ser Pro Ala Thr Leu Ser Val Thr Pro Gly
 1               5                  10                  15

Asn Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asn Phe Thr Leu Ser Ile Asn Ser Val Glu Pro
65                  70                  75                  80

Glu Asp Val Gly Val Tyr Tyr Cys Gln Asn Gly His Ser Phe Pro Phe
                85                  90                  95

Thr Phe Gly Ser Gly Thr Lys Leu Glu Ile Lys
           100                 105
```

<210> SEQ ID NO 104
<211> LENGTH: 333
<212> TYPE: DNA
<213> ORGANISM: Mouse

<400> SEQUENCE: 104

```
gacattgtgc tgacacagtc tcctgcttcc ttagctgttt ctctggggca gagggccacc       60
atctcatgca gggccagcaa aagtgtcaga ttctctgact attttatat gcactggtac        120 caacagaaac caggacagcc acccaaactc ctcatctacc ttgcatccaa cctagaatct       180
ggggtccctg ccaggttcag tggcagtggg tctgggacag acttcaccct caacatccat       240
cctgtggagg aggaggatgc tgcaacctat tactgtcaga acagtaggga gcttccgtac       300
acgttcggag gggggaccaa gctggagata aaa                                     333
```

<210> SEQ ID NO 105
<211> LENGTH: 111
<212> TYPE: PRT
<213> ORGANISM: Mouse

<400> SEQUENCE: 105

```
Asp Ile Val Leu Thr Gln Ser Pro Ala Ser Leu Ala Val Ser Leu Gly
 1               5                  10                  15

Gln Arg Ala Thr Ile Ser Cys Arg Ala Ser Lys Ser Val Arg Phe Ser
            20                  25                  30

Asp Tyr Phe Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Asn Ser Arg
```

```
                85                  90                  95
Glu Leu Pro Tyr Thr Phe Gly Gly Gly Thr Lys Leu Glu Ile Lys
            100                 105                 110
```

<210> SEQ ID NO 106
<211> LENGTH: 333
<212> TYPE: DNA
<213> ORGANISM: Mouse

<400> SEQUENCE: 106

```
gacattgtgt tgacacagtc tcctgcttcc ttagctgtat ctctggggca gagggccacc    60
atctcatgca gggccagcaa aagtgtcagt acatctggct atagttatat acactggtac   120
caacagaaac cggacagcc acccaaattc tcatctatc ttgcatccaa cctagattct    180
ggggtccctg ccaggttcag tggcagtggg tctgggacag acttcaccct caacatccat   240
cctgtggagg aggaggatgc tgcaacctat tactgtcagc acagtaggga gcttccgtac   300
acgttcggag gggggaccaa gctggaaata aaa                                333
```

<210> SEQ ID NO 107
<211> LENGTH: 111
<212> TYPE: PRT
<213> ORGANISM: Mouse

<400> SEQUENCE: 107

```
Asp Ile Val Leu Thr Gln Ser Pro Ala Ser Leu Ala Val Ser Leu Gly
  1               5                  10                  15
Gln Arg Ala Thr Ile Ser Cys Arg Ala Ser Lys Ser Val Ser Thr Ser
             20                  25                  30
Gly Tyr Ser Tyr Ile His Trp Tyr Gln Gln Lys Pro Gly Gln Pro Pro
         35                  40                  45
Lys Phe Leu Ile Tyr Leu Ala Ser Asn Leu Asp Ser Gly Val Pro Ala
     50                  55                  60
Arg Phe Ser Gly Ser Gly Ser Gly Thr Asp Phe Thr Leu Asn Ile His
 65                  70                  75                  80
Pro Val Glu Glu Glu Asp Ala Ala Thr Tyr Tyr Cys Gln His Ser Arg
                 85                  90                  95
Glu Leu Pro Tyr Thr Phe Gly Gly Gly Thr Lys Leu Glu Ile Lys
            100                 105                 110
```

<210> SEQ ID NO 108
<211> LENGTH: 321
<212> TYPE: DNA
<213> ORGANISM: Mouse

<400> SEQUENCE: 108

```
gacattgtga tgactcagtc tccagccacc ctgtctgtga ctccaggaga tagagtctct    60
ctttcctgca gggccagcca gagtattagc gactacttac actggtatca acaaaaatca   120
catgagtctc caaggcttct catcaaatat gcttcccaat ccatctctgg atcccctcc    180
aggttcagtg gcagtggatc agggtcagat ttcactctca gtatcaacag tgtggaacct   240
gaagatgttg gagtgtatta ctgtcaaaat ggtcacagct ttccgtacac gttcggaggg   300
gggaccaagc tggaaataaa a                                             321
```

<210> SEQ ID NO 109
<211> LENGTH: 107
<212> TYPE: PRT
<213> ORGANISM: Mouse

<400> SEQUENCE: 109

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Tyr
                85                  90                  95

Thr Phe Gly Gly Gly Thr Lys Leu Glu Ile Lys
            100                 105

<210> SEQ ID NO 110
<211> LENGTH: 336
<212> TYPE: DNA
<213> ORGANISM: Mouse

<400> SEQUENCE: 110
gatgttgtga tgacccaaac tccactctcc ctgcctgtca gtcttggaga tcaagcctcc       60
atctcttgca gatctagtca gagccttgta cacagtaatg aaacaccta tttacattgg      120 tacctgcaga agccaggcca gtctccaaag ctcctgatct acaaagtttc caaccgattt      180 tctgggtcc ccgacaggtt cagtggcagt ggatcaggga cagatttcac actcaagatc      240
agcagagtgg aggctgagga tctgggagtt tatttctgct ctcaaagtac acatgttccg      300
tacacgttcg gaggggggac caagctggaa ataaat                               336

<210> SEQ ID NO 111
<211> LENGTH: 112
<212> TYPE: PRT
<213> ORGANISM: Mouse

<400> SEQUENCE: 111

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Tyr Thr Phe Gly Gly Gly Thr Lys Leu Glu Ile Asn
            100                 105                 110

<210> SEQ ID NO 112
<211> LENGTH: 318
<212> TYPE: DNA
<213> ORGANISM: Mouse

<400> SEQUENCE: 112

```
gacattatga tgacccagtc tcacaaattc atgtccacat cagtaggaga cagggtcagc      60
atcacctgca aggccagtca ggatgtgggt aatgctgtgg tctggtatca acaaaaacca    120
gggcaatctc ctaaactact gatttactgg gcatccaccc ggcacattgg agtccctgat    180
cgcttcacag gcagtggatc tgggacagat ttcactctca ccattaccaa tgtgcagtct    240
gaagacttgg cagattattt ctgtcagcaa tatagcagct atctcacgtt cggtgctggg    300
accaagctgg agctgaaa                                                  318
```

<210> SEQ ID NO 113
<211> LENGTH: 106
<212> TYPE: PRT
<213> ORGANISM: Mouse

<400> SEQUENCE: 113

```
Asp Ile Met Met Thr Gln Ser His Lys Phe Met Ser Thr Ser Val Gly
  1               5                  10                  15
Asp Arg Val Ser Ile Thr Cys Lys Ala Ser Gln Asp Val Gly Asn Ala
             20                  25                  30
Val Val Trp Tyr Gln Gln Lys Pro Gly Gln Ser Pro Lys Leu Leu Ile
         35                  40                  45
Tyr Trp Ala Ser Thr Arg His Ile Gly Val Pro Asp Arg Phe Thr Gly
     50                  55                  60
Ser Gly Ser Gly Thr Asp Phe Thr Leu Thr Ile Thr Asn Val Gln Ser
 65                  70                  75                  80
Glu Asp Leu Ala Asp Tyr Phe Cys Gln Gln Tyr Ser Ser Tyr Leu Thr
                 85                  90                  95
Phe Gly Ala Gly Thr Lys Leu Glu Leu Lys
            100                 105
```

<210> SEQ ID NO 114
<211> LENGTH: 336
<212> TYPE: DNA
<213> ORGANISM: Mouse

<400> SEQUENCE: 114

```
gatgttgtga tgacccaatc tccactctcc ctgcctgtca gtcttggaga tcaagcctcc      60
atctcttgca gatctagtca gagccttgta cacagtaatg gaaacaccta tctacattgg    120
tacctgctga agccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tatttctgct ctcaaagtac acatgttccg    300
tacacgttcg gaggggggac caagctggaa ataaaa                              336
```

<210> SEQ ID NO 115
<211> LENGTH: 112
<212> TYPE: PRT
<213> ORGANISM: Mouse

<400> SEQUENCE: 115

```
Asp Val Val Met Thr Gln Ser Pro Leu Ser Leu Pro Val Ser Leu Gly
  1               5                  10                  15
Asp Gln Ala Ser Ile Ser Cys Arg Ser Ser Gln Ser Leu Val His Ser
             20                  25                  30
Asn Gly Asn Thr Tyr Leu His Trp Tyr Leu Leu Lys Pro Gly Gln Ser
         35                  40                  45
```

```
Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Tyr Thr Phe Gly Gly Gly Thr Lys Leu Glu Ile Lys
            100                 105                 110

<210> SEQ ID NO 116
<211> LENGTH: 321
<212> TYPE: DNA
<213> ORGANISM: Mouse

<400> SEQUENCE: 116
gacatccaga tgactcagtc tccagttttc ctgtctgcat ctgtgggaga aactgtcacc      60
atcacatgtc gagcaagtga gaatattgac agttatttag catggtatca gcagaaacag     120
ggaaaatctc ctcagctcct ggtctttgct gcacgaaact tagcagatgg tgtgccatca     180
aggttcagtg gcagtggatc aggcacacag tattctctca agatcaacag aatgcagtct     240
gaagatgttg cgagatacta ctgtcaacat tattatagta ctccattcac gttcggctcg     300
gggacaaagt tggaaataga a                                               321

<210> SEQ ID NO 117
<211> LENGTH: 107
<212> TYPE: PRT
<213> ORGANISM: Mouse

<400> SEQUENCE: 117

Asp Ile Gln Met Thr Gln Ser Pro Val Phe Leu Ser Ala Ser Val Gly
  1               5                  10                  15

Glu Thr Val Thr Ile Thr Cys Arg Ala Ser Glu Asn Ile Asp Ser Tyr
                20                  25                  30

Leu Ala Trp Tyr Gln Gln Lys Gln Gly Lys Ser Pro Gln Leu Leu Val
            35                  40                  45

Phe Ala Ala Arg Asn Leu Ala Asp Gly Val Pro Ser Arg Phe Ser Gly
    50                  55                  60

Ser Gly Ser Gly Thr Gln Tyr Ser Leu Lys Ile Asn Arg Met Gln Ser
65                  70                  75                  80

Glu Asp Val Ala Arg Tyr Tyr Cys Gln His Tyr Tyr Ser Thr Pro Phe
                85                  90                  95

Thr Phe Gly Ser Gly Thr Lys Leu Glu Ile Glu
            100                 105

<210> SEQ ID NO 118
<211> LENGTH: 321
<212> TYPE: DNA
<213> ORGANISM: Mouse

<400> SEQUENCE: 118
gacatccaga tgactcagtc gccagcttcc ctgtctgcat ctgtgggaga aactgtcatc      60
ttcacatgtc gagcaagtga gaatattgac agttatttag catggtatca gcagaaacag     120
ggaaaatctc ctcagctcct ggtctatgct gcaacaaact tagcagatgg tgtgccatca     180
aggttcagtg gcagtggatc aggcacacag tattctctca agatcaacag cctgcagtct     240
gaagatgttg cgagatatta ctgtctacat tattatagta ctccattcac gttcggctcg     300
```
gggacagagt tggaaataaa a					321

<210> SEQ ID NO 119
<211> LENGTH: 107
<212> TYPE: PRT
<213> ORGANISM: Mouse

<400> SEQUENCE: 119

Asp Ile Gln Met Thr Gln Ser Pro Ala Ser Leu Ser Ala Ser Val Gly
1               5                   10                  15

Glu Thr Val Ile Phe Thr Cys Arg Ala Ser Glu Asn Ile Asp Ser Tyr
            20                  25                  30

Leu Ala Trp Tyr Gln Gln Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Val Ala Arg Tyr Tyr Cys Leu His Tyr Tyr Ser Thr Pro Phe
                85                  90                  95

Thr Phe Gly Ser Gly Thr Glu Leu Glu Ile Lys
            100                 105

<210> SEQ ID NO 120
<211> LENGTH: 357
<212> TYPE: DNA
<213> ORGANISM: Mouse

<400> SEQUENCE: 120
caggtgcagc tgaaggagtc aggacctggc ctggtggcgc cctcacagag cctgtccatc		60
acatgcactg tctctgggtt ctcattaacc acctatgcta taagctgggt tcgccagtca		120
ccaggaaagg gtctggagtg gcttggagtc atatggactg gtggaggcac aaaatataat		180
tcagctctca atccagact gagcatcagc aaagacaact ccaagagtca gttttctta		240
aaaatgaaca gtctgcaaac tgatgacaca gccaggtact actgtgccag aaaggactat		300
aattacgggg gtgctatgga ctactggggt caaggaacct cagtcaccgt ctcctca		357

<210> SEQ ID NO 121
<211> LENGTH: 119
<212> TYPE: PRT
<213> ORGANISM: Mouse

<400> SEQUENCE: 121

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Thr Tyr
            20                  25                  30

Ala Ile Ser Trp Val Arg Gln Ser Pro Gly Lys Gly Leu Glu Trp Leu
        35                  40                  45

Gly Val Ile Trp Thr Gly Gly Gly Thr Lys Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Arg Tyr Tyr Cys Ala
                85                  90                  95

Arg Lys Asp Tyr Asn Tyr Gly Gly Ala Met Asp Tyr Trp Gly Gln Gly

-continued

```
                 100                 105                 110
Thr Ser Val Thr Val Ser Ser
                         115

<210> SEQ ID NO 122
<211> LENGTH: 360
<212> TYPE: DNA
<213> ORGANISM: Mouse

<400> SEQUENCE: 122
caggttcagc tgcaacagtc tgacgctgag ttggtgaaac ctggcacttc agtgaagaca      60
tcctgcaaaa tttctggcaa caccttcact gaccaaacta ttcactggat gaagcagagg     120
cctgaacagg gcctggaatg gattggatat atttatccta gagatgatag tcctaagtac     180
aatgagaact tcaagggcaa ggccacattg actgcagaca atcctccag cacagcctac      240 atgcagctca acagtctgac atctgaggac tctgcagtct atttctgtgc aatcccagac     300
aggtcaggct acgcctggtt tatttactgg ggccaaggga ctctggtcac tgtctcttca     360

<210> SEQ ID NO 123
<211> LENGTH: 120
<212> TYPE: PRT
<213> ORGANISM: Mouse

<400> SEQUENCE: 123

Gln Val Gln Leu Gln Gln Ser Asp Ala Glu Leu Val Lys Pro Gly Thr
  1               5                  10                  15

Ser Val Lys Thr Ser Cys Lys Ile Ser Gly Asn Thr Phe Thr Asp Gln
                 20                  25                  30

Thr Ile His Trp Met Lys Gln Arg Pro Glu Gln Gly Leu Glu Trp Ile
             35                  40                  45

Gly Tyr Ile Tyr Pro Arg Asp Asp Ser Pro Lys Tyr Asn Glu Asn Phe
         50                  55                  60

Lys Gly Lys Ala Thr Leu Thr Ala Asp Lys Ser Ser Thr Ala Tyr
 65                  70                  75                  80

Met Gln Leu Asn Ser Leu Thr Ser Glu Asp Ser Ala Val Tyr Phe Cys
                 85                  90                  95

Ala Ile Pro Asp Arg Ser Gly Tyr Ala Trp Phe Ile Tyr Trp Gly Gln
                100                 105                 110

Gly Thr Leu Val Thr Val Ser Ser
                115                 120

<210> SEQ ID NO 124
<211> LENGTH: 357
<212> TYPE: DNA
<213> ORGANISM: Mouse

<400> SEQUENCE: 124
caggtgcagc tgaaggagtc aggacctgtc ctggtggcgc cctcacagag cctgtccatc      60
acatgcactg tctctggggtt ctcattaaac aactttgcta taagttgggt tcgtcagcca    120
ccaggaaagg gtctggagtg gcttggagca atatggactg gtggaggcac aaattataat     180
tcagctctca aatccagact gagcatcagc aaagacaact ccaagagtca gttttcttta    240
aaaatgaaca gtctgcaaac tgatgacaca gccaggtatt attgtgtcag aaaggactat    300
agttacgggg gtgctatgga ctactggggt caaggaacct cagtcaccgt ctcctca       357

<210> SEQ ID NO 125
```

<211> LENGTH: 119
<212> TYPE: PRT
<213> ORGANISM: Mouse

<400> SEQUENCE: 125

Gln Val Gln Leu Lys Glu Ser Gly Pro Val Leu Val Ala Pro Ser Gln
1               5                   10                  15
Ser Leu Ser Ile Thr Cys Thr Val Ser Gly Phe Ser Leu Asn Asn Phe
            20                  25                  30
Ala Ile Ser Trp Val Arg Gln Pro Pro Gly Lys Gly Leu Glu Trp Leu
        35                  40                  45
Gly Ala Ile Trp Thr Gly Gly Gly Thr Asn Tyr Asn Ser Ala Leu Lys
    50                  55                  60
Ser Arg Leu Ser Ile Ser Lys Asp Asn Ser Lys Ser Gln Val Phe Leu
65                  70                  75                  80
Lys Met Asn Ser Leu Gln Thr Asp Asp Thr Ala Arg Tyr Tyr Cys Val
                85                  90                  95
Arg Lys Asp Tyr Ser Tyr Gly Gly Ala Met Asp Tyr Trp Gly Gln Gly
            100                 105                 110
Thr Ser Val Thr Val Ser Ser
        115

<210> SEQ ID NO 126
<211> LENGTH: 354
<212> TYPE: DNA
<213> ORGANISM: Mouse

<400> SEQUENCE: 126
gaggtccagc tgcaacagtc tggacctgtg ctggtgaagc ctggggcttc agtgaagatg    60
tcctgtaagg cttctggata cacattcact gactactata tgaactgggt gaagcagagc   120
catggaaaga gccttgagtg gattggagtt attattcctt acaacggtgg tactagctac   180
aaccagaagt tcaagggcaa ggccacattg actgttgaca gtcctccag cacagcctac   240
atggagctca acagcctgac atctgaggac tctgcagtct attactgtgc acgagatggt   300
caccgctggt acttcgatgt ctggggcaca gggaccacgg tcaccgtctc ctca         354

<210> SEQ ID NO 127
<211> LENGTH: 118
<212> TYPE: PRT
<213> ORGANISM: Mouse

<400> SEQUENCE: 127

Glu Val Gln Leu Gln Gln Ser Gly Pro Val Leu Val Lys Pro Gly Ala
1               5                   10                  15
Ser Val Lys Met Ser Cys Lys Ala Ser Gly Tyr Thr Phe Thr Asp Tyr
            20                  25                  30
Tyr Met Asn Trp Val Lys Gln Ser His Gly Lys Ser Leu Glu Trp Ile
        35                  40                  45
Gly Val Ile Ile Pro Tyr Asn Gly Gly Thr Ser Tyr Asn Gln Lys Phe
    50                  55                  60
Lys Gly Lys Ala Thr Leu Thr Val Asp Lys Ser Ser Ser Thr Ala Tyr
65                  70                  75                  80
Met Glu Leu Asn Ser Leu Thr Ser Glu Asp Ser Ala Val Tyr Tyr Cys
                85                  90                  95
Ala Arg Asp Gly His Arg Trp Tyr Phe Asp Val Trp Gly Thr Gly Thr
            100                 105                 110

```
Thr Val Thr Val Ser Ser
            115

<210> SEQ ID NO 128
<211> LENGTH: 115
<212> TYPE: PRT
<213> ORGANISM: Mouse

<400> SEQUENCE: 128

Glu Val Gln Leu Gln Gln Ser Gly Pro Glu Leu Val Lys Pro Gly Ala
 1               5                  10                  15

Ser Val Lys Met Ser Cys Lys Ala Ser Gly Tyr Thr Phe Thr Cys Cys
            20                  25                  30

Ile Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Arg Trp Asp Glu Ala Tyr Trp Gly Gln Gly Thr Leu Val Thr
            100                 105                 110

Val Ser Ala
        115

<210> SEQ ID NO 129
<211> LENGTH: 345
<212> TYPE: DNA
<213> ORGANISM: Mouse

<400> SEQUENCE: 129
gaggtccagc tgcagcagtc tggacctgag ctggtcaagc ctggggcttc agtgaagatg    60
tcctgcaagg cttctggata cacattcact cgctatctta ttcactgggt gaaacagaag   120
cctgggcagg gccttgagtg gattggatat attaatcctt acaatgatgg tactaaatac   180
aatgagaagt tcaaaggcaa ggccacactg acttcagaca atcctccag cacagcctac    240 atggagctca gcagcctgac ctctgaggac tctgcggtct attactgtac ctctaactgg   300
gacctcgact actggggcca aggcaccact ctcacagtct cctca                   345

<210> SEQ ID NO 130
<211> LENGTH: 115
<212> TYPE: PRT
<213> ORGANISM: Mouse

<400> SEQUENCE: 130

Glu Val Gln Leu Gln Gln Ser Gly Pro Glu Leu Val Lys Pro Gly Ala
 1               5                  10                  15

Ser Val Lys Met Ser Cys Lys Ala Ser Gly Tyr Thr Phe Thr Arg Tyr
            20                  25                  30

Leu Ile His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
```

```
                        85                  90                  95
Thr Ser Asn Trp Asp Leu Asp Tyr Trp Gly Gln Gly Thr Thr Leu Thr
                   100                 105                 110

Val Ser Ser
        115

<210> SEQ ID NO 131
<211> LENGTH: 345
<212> TYPE: DNA
<213> ORGANISM: Mouse

<400> SEQUENCE: 131
gaggtccagc tgcagcagtc tggacctgaa gtggtaaagc ctggggcttc agtgaagatg      60
tcctgcaagg cctctggata cacattcact agttctgtta tacactgggt gaagcagaag     120
gctgggcagg gccttgagtg gattggatat atcaatccct ataatgatgg tactaagtac     180
aatgagaagt tcaaaggcaa ggccacactg acttcagaca gatcctccag cacagcctac     240
atggagctca gcagcctgac ctctgaggac tctgcggtct attactgtac aagacggttg     300
gacgaggctt actggggcca aggactctg gtcactgtct ctgca                      345

<210> SEQ ID NO 132
<211> LENGTH: 115
<212> TYPE: PRT
<213> ORGANISM: Mouse

<400> SEQUENCE: 132

Glu Val Gln Leu Gln Gln Ser Gly Pro Glu Val Val Lys Pro Gly Ala
 1               5                  10                  15

Ser Val Lys Met Ser Cys Lys Ala Ser Gly Tyr Thr Phe Thr Ser Ser
                20                  25                  30

Val Ile His Trp Val Lys Gln Lys Ala Gly Gln Gly Leu Glu Trp Ile
            35                  40                  45

Gly Tyr Ile Asn Pro Tyr Asn Asp Gly Thr Lys Tyr Asn Glu Lys Phe
        50                  55                  60

Lys Gly Lys Ala Thr Leu Thr Ser Asp Arg Ser Ser Ser Thr Ala Tyr
 65                 70                  75                  80

Met Glu Leu Ser Ser Leu Thr Ser Glu Asp Ser Ala Val Tyr Tyr Cys
                85                  90                  95

Thr Arg Arg Leu Asp Glu Ala Tyr Trp Gly Gln Gly Thr Leu Val Thr
                100                 105                 110

Val Ser Ala
        115

<210> SEQ ID NO 133
<211> LENGTH: 345
<212> TYPE: DNA
<213> ORGANISM: Mouse

<400> SEQUENCE: 133
gaggtccagc tgcagcagtc tggacctgag ctggtaaagc ctggggctgc agtgaagatg      60
tcctgcaagg cttctggata cacattcact cgctatctta ttcactgggt gaagcagaag     120
cctgggcagg gccttgagtg gattggatat attaatcctt acaatgatgg tactaaatat     180
aatgagaagt tcaaaggcaa ggccacactg acttcagaca atcctccag cacagcctac      240 atggagctca gcagcctgac ctctgaggac tctgcggtct attactgtac ctctaattgg     300
gacctcgact actggggcca aggcaccact ctcacagtct cctca                     345
```

<210> SEQ ID NO 134
<211> LENGTH: 115
<212> TYPE: PRT
<213> ORGANISM: Mouse

<400> SEQUENCE: 134

```
Glu Val Gln Leu Gln Gln Ser Gly Pro Glu Leu Val Lys Pro Gly Ala
 1               5                  10                  15

Ala Val Lys Met Ser Cys Lys Ala Ser Gly Tyr Thr Phe Thr Arg Tyr
                20                  25                  30

Leu Ile His Trp Val Lys Gln Lys Pro Gly Gln Gly Leu Glu Trp Ile
            35                  40                  45

Gly Tyr Ile Asn Pro Tyr Asn Asp Gly Thr Lys Tyr Asn Glu Lys Phe
        50                  55                  60

Lys Gly Lys Ala Thr Leu Thr Ser Asp Lys Ser Ser Thr Ala Tyr
 65                  70                  75                  80

Met Glu Leu Ser Ser Leu Thr Ser Glu Asp Ser Ala Val Tyr Tyr Cys
                85                  90                  95

Thr Ser Asn Trp Asp Leu Asp Tyr Trp Gly Gln Gly Thr Thr Leu Thr
                100                 105                 110

Val Ser Ser
        115
```

<210> SEQ ID NO 135
<211> LENGTH: 345
<212> TYPE: DNA
<213> ORGANISM: Mouse

<400> SEQUENCE: 135

```
gaggtccagc tgcagcagtc tggacctgaa ctggtaaagc ctggggcttc agtgaagatg    60
tcctgcaagg cctctggata cacattcact agttctgtta tgcactgggt gaagcagaag   120
gctgggcagg gccttgagtg gattggatat atcaatccct ataatgatgg tactcagtac   180
aatgagaagt tcaaaggcaa ggccacactg acttcagaca attttccag cacagcctac    240
atggagctca gcagcctgac ctctgaggac tctgcggtct attactgtac aagacggttg   300
gacgaggctt actggggcca agggactctg gtcactgtct ctgca                   345
```

<210> SEQ ID NO 136
<211> LENGTH: 115
<212> TYPE: PRT
<213> ORGANISM: Mouse

<400> SEQUENCE: 136

```
Glu Val Gln Leu Gln Gln Ser Gly Pro Glu Leu Val Lys Pro Gly Ala
 1               5                  10                  15

Ser Val Lys Met Ser Cys Lys Ala Ser Gly Tyr Thr Phe Thr Ser Ser
                20                  25                  30

Val Met His Trp Val Lys Gln Lys Ala Gly Gln Gly Leu Glu Trp Ile
            35                  40                  45

Gly Tyr Ile Asn Pro Tyr Asn Asp Gly Thr Gln Tyr Asn Glu Lys Phe
        50                  55                  60

Lys Gly Lys Ala Thr Leu Thr Ser Asp Lys Phe Ser Ser Thr Ala Tyr
 65                  70                  75                  80

Met Glu Leu Ser Ser Leu Thr Ser Glu Asp Ser Ala Val Tyr Tyr Cys
                85                  90                  95
```

Thr Arg Arg Leu Asp Glu Ala Tyr Trp Gly Gln Gly Thr Leu Val Thr
            100                 105                 110

Val Ser Ala
        115

<210> SEQ ID NO 137
<211> LENGTH: 345
<212> TYPE: DNA
<213> ORGANISM: Mouse

<400> SEQUENCE: 137
gaggtccagc tgcagcagtc tggacctgag ctggtaaagc ctggggcttc agtgaagatg      60
tcctgcaagg cttctggata cacattcact agctctatta ttcactgggt gaagcagagg     120
cctgggcagg gccttgagtg gattggatat attaatcctt acgatgatgt tactaagtac     180
aatgagaagt tcaaaggcaa ggccacactg acttcagaca atcctccag cacagcctac      240 atggagctca gcagcctgac ctctgaggac tctgcggtct attactgtgc aagacggtgg     300
gacgagtctt actggggcca aggactctg gtcactgtct ctgca                      345

<210> SEQ ID NO 138
<211> LENGTH: 115
<212> TYPE: PRT
<213> ORGANISM: Mouse

<400> SEQUENCE: 138

Glu Val Gln Leu Gln Gln Ser Gly Pro Glu Leu Val Lys Pro Gly Ala
 1               5                  10                  15

Ser Val Lys Met Ser Cys Lys Ala Ser Gly Tyr Thr Phe Thr Ser Ser
             20                  25                  30

Ile Ile His Trp Val Lys Gln Arg Pro Gly Gln Gly Leu Glu Trp Ile
         35                  40                  45

Gly Tyr Ile Asn Pro Tyr Asp Asp Val Thr Lys Tyr Asn Glu Lys Phe
     50                  55                  60

Lys Gly Lys Ala Thr Leu Thr Ser Asp Lys Ser Ser Ser Thr Ala Tyr
 65                  70                  75                  80

Met Glu Leu Ser Ser Leu Thr Ser Glu Asp Ser Ala Val Tyr Tyr Cys
                 85                  90                  95

Ala Arg Arg Trp Asp Glu Ser Tyr Trp Gly Gln Gly Thr Leu Val Thr
            100                 105                 110

Val Ser Ala
        115

<210> SEQ ID NO 139
<211> LENGTH: 345
<212> TYPE: DNA
<213> ORGANISM: Mouse

<400> SEQUENCE: 139
gaggtccagc tgcagcagtc tggacctgag ctggtaaagc ctggggcttc agtgaagatg      60
tcctgcaagg cttctggata cactttcact acctctatta tgcactgggt gaaacagaag     120
cctgggcagg gccttgagtg gattggatat attaatcctt acgatgatgt tactaagtac     180
aatgaaaagt tcaaaggcaa ggccacattg acttcagaca atcctccag cacagcctac      240 atggagctca gcagcctgac ctctgaggac tctgcagtct attactgtgt aagacggtgg     300
gacgaggctt actggggcca aggactctg gtcactgtct ctgca                      345

<210> SEQ ID NO 140
<211> LENGTH: 115
<212> TYPE: PRT
<213> ORGANISM: Mouse

<400> SEQUENCE: 140

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Thr Ser
            20                  25                  30

Ile Met His Trp Val Lys Gln Lys Pro Gly Gln Gly Leu Glu Trp Ile
        35                  40                  45

Gly Tyr Ile Asn Pro Tyr Asp Asp Val Thr Lys Tyr Asn Glu Lys Phe
    50                  55                  60

Lys Gly Lys Ala Thr Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Val Arg Arg Trp Asp Glu Ala Tyr Trp Gly Gln Gly Thr Leu Val Thr
            100                 105                 110

Val Ser Ala
        115

<210> SEQ ID NO 141
<211> LENGTH: 357
<212> TYPE: DNA
<213> ORGANISM: Mouse

<400> SEQUENCE: 141
gaggtccagc tgcaacaatc tggacctgag ctggtgaagc ctggggcttc agtgaagata      60
tcctgtaagg cttctggata cacgtttact gactactaca tgaactgggt gaggcagagc     120
catggagaga gccttgagtg gattggagat tttaatcata acaatgatgt tattacttac     180
aacccgaagt tcaagggcaa ggtcacattg actgtagaga gtcttccac cacagcctac     240 atggagctcc gcagcctgtc atctgaggac tctgcagtct attactgtgc aaggggcta      300 cgaggctact atgctatgga ctactgggt caaggaacct cagtcaccgt ctcctca        357

<210> SEQ ID NO 142
<211> LENGTH: 119
<212> TYPE: PRT
<213> ORGANISM: Mouse

<400> SEQUENCE: 142

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Met Asn Trp Val Arg Gln Ser His Gly Glu Ser Leu Glu Trp Ile
        35                  40                  45

Gly Asp Phe Asn His Asn Asn Asp Val Ile Thr Tyr Asn Pro Lys Phe
    50                  55                  60

Lys Gly Lys Val Thr Leu Thr Val Glu Lys Ser Ser Thr Thr Ala Tyr
65                  70                  75                  80

Met Glu Leu Arg Ser Leu Ser Ser Glu Asp Ser Ala Val Tyr Tyr Cys
                85                  90                  95

Ala Arg Gly Leu Arg Gly Tyr Tyr Ala Met Asp Tyr Trp Gly Gln Gly
            100                 105                 110

-continued

Thr Ser Val Thr Val Ser Ser
        115

<210> SEQ ID NO 143
<211> LENGTH: 354
<212> TYPE: DNA
<213> ORGANISM: Mouse

<400> SEQUENCE: 143
caggttcagc tgcaacagtc tgacgctgag ttggtgaaac ctggagcttc agtgaagata      60
tcctgcaagg tttctggcta caccttcact gaccatacta ttcactggat gaagcagagg     120
cctgaacagg gcctggaatg gattggatat atttatccta gagatggtta tcctaagttc     180
aatgagaagt tcaagggcaa ggccacattg actgcagaca atcctccag cacagcctac      240 atgcagctca acagcctgac atctgaggac tctgcagtct atttctgtgc aagacggccc     300
ccttactatg ctatggacta ctggggtcaa ggaacctcag tcgccgtctc ctca           354

<210> SEQ ID NO 144
<211> LENGTH: 118
<212> TYPE: PRT
<213> ORGANISM: Mouse

<400> SEQUENCE: 144

Gln Val Gln Leu Gln Gln Ser Asp Ala Glu Leu Val Lys Pro Gly Ala
 1               5                  10                  15

Ser Val Lys Ile Ser Cys Lys Val Ser Gly Tyr Thr Phe Thr Asp His
            20                  25                  30

Thr Ile His Trp Met Lys Gln Arg Pro Glu Gln Gly Leu Glu Trp Ile
        35                  40                  45

Gly Tyr Ile Tyr Pro Arg Asp Gly Tyr Pro Lys Phe Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Asn Ser Leu Thr Ser Glu Asp Ser Ala Val Tyr Phe Cys
                85                  90                  95

Ala Arg Arg Pro Pro Tyr Tyr Ala Met Asp Tyr Trp Gly Gln Gly Thr
            100                 105                 110

Ser Val Ala Val Ser Ser
        115

<210> SEQ ID NO 145
<211> LENGTH: 345
<212> TYPE: DNA
<213> ORGANISM: Mouse

<400> SEQUENCE: 145
gaggtccaac tgcagcagtc tggacctgag ctggtaaagc ctggggcttc agtgaagatg      60
tcctgcaagg cttctggata cacattcact aggtatctta tgcactgggt gaagcagaag     120
cctgggcagg gccttgagtg gattggttat attaatcctt acaatgatgg tactaattac     180
aatgagaagt tcaaaggcaa ggccacactg acttcagaca atcctccag cacagcctac      240 atggagctca gcagcctgac ctctgaggac tctgcggtct attactgttc ccttaactgg     300
gactatgctt actggggcca agggactctg gtcactgtct ctgca                     345

<210> SEQ ID NO 146
<211> LENGTH: 115

<212> TYPE: PRT
<213> ORGANISM: Mouse

<400> SEQUENCE: 146

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Arg Tyr
            20                  25                  30

Leu Met His Trp Val Lys Gln Lys Pro Gly Gln Gly Leu Glu Trp Ile
        35                  40                  45

Gly Tyr Ile Asn Pro Tyr Asn Asp Gly Thr Asn Tyr Asn Glu Lys Phe
    50                  55                  60

Lys Gly Lys Ala Thr Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Ser Leu Asn Trp Asp Tyr Ala Tyr Trp Gly Gln Gly Thr Leu Val Thr
            100                 105                 110

Val Ser Ala
        115

<210> SEQ ID NO 147
<211> LENGTH: 360
<212> TYPE: DNA
<213> ORGANISM: Mouse

<400> SEQUENCE: 147
gagttccagc tgcagcagtc tggacctgag ctggtgaagc ctggcgcttc agtgaagata     60
tcctgcaagg cttctggtta ctcattcact gactacaaca tgaactgggt gaagcagagc    120
aaaggaaaga gccttgagtg gattggagta attattccta actatggttt tactagctac    180
aatcagaact tcaagggcaa ggccactttg actgtagacc agtcttccag cacagcccac    240
atgcagctca acagtgtgac atctgaggac tctgcagtct attactgtgt aagagatggg    300
ggaatactcc tctggtatct cgatgtctgg ggcacaggga ccacggtcac cgtctcctca    360

<210> SEQ ID NO 148
<211> LENGTH: 120
<212> TYPE: PRT
<213> ORGANISM: Mouse

<400> SEQUENCE: 148

Glu Phe Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Asp Tyr
            20                  25                  30

Asn Met Asn Trp Val Lys Gln Ser Lys Gly Lys Ser Leu Glu Trp Ile
        35                  40                  45

Gly Val Ile Ile Pro Asn Tyr Gly Phe Thr Ser Tyr Asn Gln Asn Phe
    50                  55                  60

Lys Gly Lys Ala Thr Leu Thr Val Asp Gln Ser Ser Ser Thr Ala His
65                  70                  75                  80

Met Gln Leu Asn Ser Val Thr Ser Glu Asp Ser Ala Val Tyr Tyr Cys
                85                  90                  95

Val Arg Asp Gly Gly Ile Leu Leu Trp Tyr Leu Asp Val Trp Gly Thr
            100                 105                 110

Gly Thr Thr Val Thr Val Ser Ser

<210> SEQ ID NO 149
<211> LENGTH: 366
<212> TYPE: DNA
<213> ORGANISM: Mouse

<400> SEQUENCE: 149
gaggtccagc tgcaacagtc tggacctgag ctggtgaagc ctggggcttc agtgaagata    60
ccctgcaagg cttctggata cacattcact gactacaaca tggactgggt gaagaagagc   120
catggaaaga gccttgagtg gattggagat atcaatcctc acaatggtgg tactatctac   180
aaccagaagt tcaagggcaa ggccacattg actgtagaca gtcctccag cacagcccac    240 atggagctcc gcagcctgac atctgaggac actgcagtct attactgtgc aagaaattac   300
tacggtagta gttacggctg gtacttcgat gtctggggca gggaccac ggtcaccgtc     360 tcgtca                                                              366

<210> SEQ ID NO 150
<211> LENGTH: 122
<212> TYPE: PRT
<213> ORGANISM: Mouse

<400> SEQUENCE: 150

Glu Val Gln Leu Gln Gln Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
            20                  25                  30

Asn Met Asp Trp Val Lys Lys Ser His Gly Lys Ser Leu Glu Trp Ile
        35                  40                  45

Gly Asp Ile Asn Pro His Asn Gly Gly Thr Ile Tyr Asn Gln Lys Phe
    50                  55                  60

Lys Gly Lys Ala Thr Leu Thr Val Asp Lys Ser Ser Ser Thr Ala His
65                  70                  75                  80

Met Glu Leu Arg Ser Leu Thr Ser Glu Asp Thr Ala Val Tyr Tyr Cys
                85                  90                  95

Ala Arg Asn Tyr Tyr Gly Ser Ser Tyr Gly Trp Tyr Phe Asp Val Trp
            100                 105                 110

Gly Thr Gly Thr Thr Val Thr Val Ser Ser
        115                 120

<210> SEQ ID NO 151
<211> LENGTH: 360
<212> TYPE: DNA
<213> ORGANISM: Mouse

<400> SEQUENCE: 151
gaggtccagc tgcagcagtc tggacctgag ctggtgaagc ctggggcttc agtgaagatt    60
tcctgcaggg cttctggtta ctcattcact ggctactaca tgaactgggt gaagcaaagt   120
cctgaaaaga gccttgagtg gattggagag attattccta ccactggtgg tacttcctac   180
aaccagaagt tcaaggccaa ggccacattg actgtagaca atcctccag cacagcctac    240 atgcagctca gagcctgac atctgaggac tctgcagtct attactgtgc aagagagagc   300
ggtgggttct actggtactt cgatgtctgg ggcacaggga ccacggtcac cgtctcctca   360

<210> SEQ ID NO 152
<211> LENGTH: 120

```
<212> TYPE: PRT
<213> ORGANISM: Mouse

<400> SEQUENCE: 152
```

| | | | | | | | | | | | | | | | |
|---|---|---|---|---|---|---|---|---|---|---|---|---|---|---|---|
| Glu | Val | Gln | Leu | Gln | Gln | Ser | Gly | Pro | Glu | Leu | Val | Lys | Pro | Gly | Ala |
| 1 | | | | 5 | | | | | 10 | | | | | 15 | |
| Ser | Val | Lys | Ile | Ser | Cys | Arg | Ala | Ser | Gly | Tyr | Ser | Phe | Thr | Gly | Tyr |
| | | | 20 | | | | | 25 | | | | | 30 | | |
| Tyr | Met | Asn | Trp | Val | Lys | Gln | Ser | Pro | Glu | Lys | Ser | Leu | Glu | Trp | Ile |
| | | 35 | | | | | 40 | | | | | 45 | | | |
| Gly | Glu | Ile | Ile | Pro | Thr | Thr | Gly | Gly | Thr | Ser | Tyr | Asn | Gln | Lys | Phe |
| 50 | | | | | 55 | | | | | 60 | | | | | |
| Lys | Ala | Lys | Ala | Thr | Leu | Thr | Val | Asp | Lys | Ser | Ser | Ser | Thr | Ala | Tyr |
| 65 | | | | | 70 | | | | | 75 | | | | | 80 |
| Met | Gln | Leu | Lys | Ser | Leu | Thr | Ser | Glu | Asp | Ser | Ala | Val | Tyr | Tyr | Cys |
| | | | | 85 | | | | | 90 | | | | | 95 | |
| Ala | Arg | Glu | Ser | Gly | Gly | Phe | Tyr | Trp | Tyr | Phe | Asp | Val | Trp | Gly | Thr |
| | | | | 100 | | | | | 105 | | | | | 110 | |
| Gly | Thr | Thr | Val | Thr | Val | Ser | Ser | | | | | | | | |
| | | | 115 | | | | | 120 | | | | | | | |

```
<210> SEQ ID NO 153
<211> LENGTH: 345
<212> TYPE: DNA
<213> ORGANISM: Mouse

<400> SEQUENCE: 153
gaggtccagc tgcagcagtc tggacctgag ctggtaaagc ctggggcttc agtgaagatg    60
tcctgcaagg cttctggata cacattcact aggtatgtta tgcactgggt gaagcagaag   120
cctgggcagg gccttgagtg gattggatat attaatcctt acaatgatgt tactaagtac   180
aatgagaagt tcaaaggcaa ggccacactg acttcagaca gatcctccag cacagcctac   240
atgaaactca gcagcctgac ctctgaggac tctgcggtct attattgtgc aagaaactgg   300
gacgttcctt actggggcca agggactctg atcactgtct ctgca                   345

<210> SEQ ID NO 154
<211> LENGTH: 115
<212> TYPE: PRT
<213> ORGANISM: Mouse

<400> SEQUENCE: 154
```

| | | | | | | | | | | | | | | | |
|---|---|---|---|---|---|---|---|---|---|---|---|---|---|---|---|
| Glu | Val | Gln | Leu | Gln | Gln | Ser | Gly | Pro | Glu | Leu | Val | Lys | Pro | Gly | Ala |
| 1 | | | | 5 | | | | | 10 | | | | | 15 | |
| Ser | Val | Lys | Met | Ser | Cys | Lys | Ala | Ser | Gly | Tyr | Thr | Phe | Thr | Arg | Tyr |
| | | | 20 | | | | | 25 | | | | | 30 | | |
| Val | Met | His | Trp | Val | Lys | Gln | Lys | Pro | Gly | Gln | Gly | Leu | Glu | Trp | Ile |
| | | 35 | | | | | 40 | | | | | 45 | | | |
| Gly | Tyr | Ile | Asn | Pro | Tyr | Asn | Asp | Val | Thr | Lys | Tyr | Asn | Glu | Lys | Phe |
| 50 | | | | | 55 | | | | | 60 | | | | | |
| Lys | Gly | Lys | Ala | Thr | Leu | Thr | Ser | Asp | Arg | Ser | Ser | Ser | Thr | Ala | Tyr |
| 65 | | | | | 70 | | | | | 75 | | | | | 80 |
| Met | Lys | Leu | Ser | Ser | Leu | Thr | Ser | Glu | Asp | Ser | Ala | Val | Tyr | Tyr | Cys |
| | | | | 85 | | | | | 90 | | | | | 95 | |
| Ala | Arg | Asn | Trp | Asp | Val | Pro | Tyr | Trp | Gly | Gln | Gly | Thr | Leu | Ile | Thr |
| | | | | 100 | | | | | 105 | | | | | 110 | |
| Val | Ser | Ala | | | | | | | | | | | | | |

<210> SEQ ID NO 155
<211> LENGTH: 345
<212> TYPE: DNA
<213> ORGANISM: Mouse

<400> SEQUENCE: 155

| | |
|---|---|
| gaggtccagc tgcagcagtc tggacctgag ctggtaaagc ctggggcttc agtgaagatg | 60 |
| tcctgcaagg cttctggata cacattcact aggtatctta tgcactgggt gaagcagaag | 120 |
| cctggacagg gccttgagtg gattggatat attaatcctt acaatgatgg tactaagtac | 180 |
| aatgagaggt tcaaaggcaa ggccacactg acttcagaca atcctccag cacagcctac | 240 |
| atggagctca gcagcctgac ctctgaggac tctgcggtct attactgtgc aagaaactgg | 300 |
| gacgtacctt actggggcca agggactctg gtcactgtct ctgca | 345 |

<210> SEQ ID NO 156
<211> LENGTH: 115
<212> TYPE: PRT
<213> ORGANISM: Mouse

<400> SEQUENCE: 156

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Arg Tyr
            20                  25                  30

Leu Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Arg Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Asn Trp Asp Val Pro Tyr Trp Gly Gln Gly Thr Leu Val Thr
            100                 105                 110

Val Ser Ala
        115

<210> SEQ ID NO 157
<211> LENGTH: 321
<212> TYPE: DNA
<213> ORGANISM: Artificial Sequence
<220> FEATURE:
<223> OTHER INFORMATION: Humanized sequence.

<400> SEQUENCE: 157

| | |
|---|---|
| gacatccaga tgacccagag cccaagcagc ctgagcgcca gcgtgggcga ccgcgtgacc | 60 |
| atcacctgca aggccagccg cgacgtggcc atcgccgtgg cctggtacca gcagaagcca | 120 |
| ggcaaggtgc caaagctgct gctgttctgg gccagcaccc gccacaccgg cgtgccagac | 180 |
| cgcttcagcg gcagcggcag cggcaccgac ttcaccctga ccatcagcag cctgcagcca | 240 |
| gaggacctgg ccgactacta ctgccaccag tacagcagct acccattcac cttcggccag | 300 |
| ggcaccaagc tggagatcaa g | 321 |

<210> SEQ ID NO 158
<211> LENGTH: 107

<212> TYPE: PRT
<213> ORGANISM: Artificial Sequence
<220> FEATURE:
<223> OTHER INFORMATION: Humanized sequence.

<400> SEQUENCE: 158

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
                20                  25                  30

Val Ala Trp Tyr Gln Gln Lys Pro Gly Lys Val Pro Lys Leu Leu Leu
            35                  40                  45

Phe Trp Ala Ser Thr Arg His Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Leu Ala Asp Tyr Tyr Cys His Gln Tyr Ser Ser Tyr Pro Phe
                85                  90                  95

Thr Phe Gly Gln Gly Thr Lys Leu Glu Ile Lys
            100                 105

<210> SEQ ID NO 159
<211> LENGTH: 321
<212> TYPE: DNA
<213> ORGANISM: Artificial Sequence
<220> FEATURE:
<223> OTHER INFORMATION: Humanized sequence.

<400> SEQUENCE: 159
gacatccaga tgacccagag cccaagcagc ctgagcgcca gcgtgggcga ccgcgtgacc      60
atcacctgca aggccagccg cgacgtggcc atcgccgtgg cctggtacca gcagaagcca     120
ggcaaggtgc caaagctgct gatctactgg gccagcaccc gccacaccgg cgtgccaagc     180
cgcttcagcg gcagcggcag ccgcaccgac ttcaccctga ccatcagcag cctgcagcca     240
gaggacgtgg ccgactactt ctgccaccag tacagcagct acccattcac cttcggcagc     300
ggcaccaagc tggagatcaa g                                               321

<210> SEQ ID NO 160
<211> LENGTH: 107
<212> TYPE: PRT
<213> ORGANISM: Artificial Sequence
<220> FEATURE:
<223> OTHER INFORMATION: Humanized sequence.

<400> SEQUENCE: 160

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
                20                  25                  30

Val Ala Trp Tyr Gln Gln Lys Pro Gly Lys Val Pro Lys Leu Leu Ile
            35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys
            100                 105

<210> SEQ ID NO 161
<211> LENGTH: 321
<212> TYPE: DNA
<213> ORGANISM: Artificial Sequence
<220> FEATURE:
<223> OTHER INFORMATION: Humanized sequence.

<400> SEQUENCE: 161

```
gacatccaga tgacccagag cccaagcagc ctgagcgcca gcgtgggcga ccgcgtgacc      60
atcacctgca aggccagccg cgacgtggcc atcgccgtgg cctggtacca gcagaagcca     120
ggcaaggtgc caaagctgct gatctactgg gccagcaccc gccacaccgg cgtgccaagc     180
cgcttcagcg gcagcggcag ccgcaccgac ttcaccctga ccatcagcag cctgcagcca     240
gaggacgtgg ccgactactt ctgccaccag tacagcagct acccattcac cttcggcagc     300
ggcaccaagc tggagatcaa g                                               321
```

<210> SEQ ID NO 162
<211> LENGTH: 107
<212> TYPE: PRT
<213> ORGANISM: Artificial Sequence
<220> FEATURE:
<223> OTHER INFORMATION: Humanized sequence.

<400> SEQUENCE: 162

Asp Ile Gln Met Thr Gln Ser Pro Ser Ser Leu Ser Ala Ser Val Gly
 1               5                  10                  15
Asp Arg Val Thr Ile Thr Cys Lys Ala Ser Arg Asp Val Ala Ile Ala
            20                  25                  30
Val Ala Trp Tyr Gln Gln Lys Pro Gly Lys Val Pro Lys Leu Leu Leu
        35                  40                  45
Tyr Trp Ala Ser Thr Arg His Thr Gly Val Pro Ser Arg Phe Ser Gly
    50                  55                  60
Ser Gly Ser Arg Thr Asp Phe Thr Leu Thr Ile Ser Ser Leu Gln Pro
65                  70                  75                  80
Glu Asp Val Ala Thr Tyr Tyr Cys His Gln Tyr Ser Ser Tyr Pro Phe
                85                  90                  95
Thr Phe Gly Ser Gly Thr Lys Leu Glu Ile Lys
            100                 105

<210> SEQ ID NO 163
<211> LENGTH: 321
<212> TYPE: DNA
<213> ORGANISM: Artificial Sequence
<220> FEATURE:
<223> OTHER INFORMATION: Humanized sequence.

<400> SEQUENCE: 163

```
gacatccaga tgacccagag cccaagcagc ctgagcgcca gcgtgggcga ccgcgtgacc      60
atcacctgca aggccagccg cgacgtggcc atcgccgtgg cctggtacca gcagaagcca     120
ggcaaggtgc caaagctgct gctgttctgg gccagcaccc gccacaccgg cgtgccagac     180
cgcttcagcg gcagcggcag ccgcaccgac ttcaccctga ccatcagcag cctgcagcca     240
gaggacctgg ccgactacta ctgccaccag tacagcagct acccattcac cttcggcagc     300
ggcaccaagc tggagatcaa g                                               321
```

<210> SEQ ID NO 164

<211> LENGTH: 107
<212> TYPE: PRT
<213> ORGANISM: Artificial Sequence
<220> FEATURE:
<223> OTHER INFORMATION: Humanized sequence.

<400> SEQUENCE: 164

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Leu
        35                  40                  45

Phe Trp Ala Ser Thr Arg His Thr Gly Val Pro Asp Arg Phe Ser Gly
    50                  55                  60

Ser Gly Ser Arg Thr Asp Phe Thr Leu Thr Ile Ser Ser Leu Gln Pro
65                  70                  75                  80

Glu Asp Leu Ala Asp Tyr Tyr Cys His Gln Tyr Ser Ser Tyr Pro Phe
                85                  90                  95

Thr Phe Gly Ser Gly Thr Lys Leu Glu Ile Lys
            100                 105

<210> SEQ ID NO 165
<211> LENGTH: 360
<212> TYPE: DNA
<213> ORGANISM: Artificial Sequence
<220> FEATURE:
<223> OTHER INFORMATION: Humanized sequence.

<400> SEQUENCE: 165
caggtgcagc tggtgcagag cggcgccgag gtgaagaagc caggcagcag cgtgaaggtg      60
agctgcaagg ccagcggcta caccttcacc gaccagacca tccactggat gcgccaggcc     120
ccaggccagg gcctggagtg gatcggctac atctacccac gcgacgacag cccaaagtac     180
aacgagaact tcaagggcaa ggtcaccatc accgccgaca gagcaccag caccgcctac     240 atggagctga gcagcctgcg cagcgaggac accgccgtgt actactgcgc catcccagac     300
cgcagcggct acgcctggtt catctactgg ggccagggca ccctggtgac cgtgagcagc     360

<210> SEQ ID NO 166
<211> LENGTH: 120
<212> TYPE: PRT
<213> ORGANISM: Artificial Sequence
<220> FEATURE:
<223> OTHER INFORMATION: Humanized sequence.

<400> SEQUENCE: 166

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Gln
            20                  25                  30

Thr Ile His Trp Met Arg Gln Ala Pro Gly Gln Gly Leu Glu Trp Ile
        35                  40                  45

Gly Tyr Ile Tyr Pro Arg Asp Asp Ser Pro Lys Tyr Asn Glu Asn Phe
    50                  55                  60

Lys Gly Lys Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ile Pro Asp Arg Ser Gly Tyr Ala Trp Phe Ile Tyr Trp Gly Gln
            100                 105                 110

Gly Thr Leu Val Thr Val Ser Ser
        115                 120

<210> SEQ ID NO 167
<211> LENGTH: 360
<212> TYPE: DNA
<213> ORGANISM: Artificial Sequence
<220> FEATURE:
<223> OTHER INFORMATION: Humanized sequence.

<400> SEQUENCE: 167
caggtgcagc tggtgcagag cggcgccgag gtgaagaagc caggcagcag cgtgaaggtg      60
agctgcaagg ccagcggctt caccttcacc gaccagacca tccactgggt gcgccaggcc     120
ccaggccagg gcctggagtg gatgggctac atctacccac gcgacgacag cccaaagtac     180
aacgagaact tcaagggcaa ggtcaccctg accgccgaca gagcaccag caccgcctac      240 atggagctga gcagcctgcg cagcgaggac accgccgtgt actactgcgc catcccagac     300
cgcagcggct acgcctggtt catctactgg ggccagggca ccctggtgac cgtgagcagc     360

<210> SEQ ID NO 168
<211> LENGTH: 120
<212> TYPE: PRT
<213> ORGANISM: Artificial Sequence
<220> FEATURE:
<223> OTHER INFORMATION: Humanized sequence.

<400> SEQUENCE: 168

Gln Val Gln Leu Val Gln Ser Gly Ala Glu Val Lys Lys Pro Gly Ser
 1               5                  10                  15

Ser Val Lys Val Ser Cys Lys Ala Ser Gly Phe Thr Phe Thr Asp Gln
            20                  25                  30

Thr Ile His Trp Val Arg Gln Ala Pro Gly Gln Gly Leu Glu Trp Met
        35                  40                  45

Gly Tyr Ile Tyr Pro Arg Asp Asp Ser Pro Lys Tyr Asn Glu Asn Phe
    50                  55                  60

Lys Gly Lys Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ile Pro Asp Arg Ser Gly Tyr Ala Trp Phe Ile Tyr Trp Gly Gln
            100                 105                 110

Gly Thr Leu Val Thr Val Ser Ser
        115                 120

<210> SEQ ID NO 169
<211> LENGTH: 360
<212> TYPE: DNA
<213> ORGANISM: Artificial Sequence
<220> FEATURE:
<223> OTHER INFORMATION: Humanized sequence.

<400> SEQUENCE: 169
caggtgcagc tggtgcagag cggcgccgag gtgaagaagc caggcagcag cgtgaagacc      60
agctgcaagg ccagcggcgg caccttcacc gaccagacca tccactgggt gcgccagcgc     120
ccaggccagg gcctggagtg gatgggctac atctacccac gcgacgacag cccaaagtac     180
aacgagaact tcaagggccg cgtcaccatc accgccgaca gagcaccag caccgcctac      240

```
atggagctga gcagcctgcg cagcgaggac accgccgtgt actactgcgc catcccagac    300
cgcagcggct acgcctggtt catctactgg ggccagggca ccctggtgac cgtgagcagc    360
```

<210> SEQ ID NO 170
<211> LENGTH: 120
<212> TYPE: PRT
<213> ORGANISM: Artificial Sequence
<220> FEATURE:
<223> OTHER INFORMATION: Humanized sequence.

<400> SEQUENCE: 170

```
Gln Val Gln Leu Val Gln Ser Gly Ala Glu Val Lys Lys Pro Gly Ser
  1               5                  10                  15

Ser Val Lys Thr Ser Cys Lys Ala Ser Gly Gly Thr Phe Thr Asp Gln
             20                  25                  30

Thr Ile His Trp Val Arg Gln Arg Pro Gly Gln Gly Leu Glu Trp Met
         35                  40                  45

Gly Tyr Ile Tyr Pro Arg Asp Asp Ser Pro Lys Tyr Asn Glu Asn Phe
     50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Ile Pro Asp Arg Ser Gly Tyr Ala Trp Phe Ile Tyr Trp Gly Gln
            100                 105                 110

Gly Thr Leu Val Thr Val Ser Ser
        115                 120
```

<210> SEQ ID NO 171
<211> LENGTH: 360
<212> TYPE: DNA
<213> ORGANISM: Artificial Sequence
<220> FEATURE:
<223> OTHER INFORMATION: Humanized sequence.

<400> SEQUENCE: 171

```
caggtgcagc tggtgcagag cggcgccgag gtgaagaagc caggcagcag cgtgaaggtg     60
agctgcaagg ccagcggcgg caccttcacc gaccagacca tccactgggt gcgccaggcc    120
ccaggccagg gctggagtg gatgggctac atctacccac gcgacgacag cccaaagtac    180
aacgagaatt tcaagggccg cgtcaccctg accgccgaca agagcaccag caccgcctac    240
atggagctga gcagcctgcg cagcgaggac accgccgtgt acttctgcgc cgcccagac    300 cgcagcggct acgcctggtt catctactgg ggccagggca ccctggtgac cgtgagcagc    360
```

<210> SEQ ID NO 172
<211> LENGTH: 120
<212> TYPE: PRT
<213> ORGANISM: Artificial Sequence
<220> FEATURE:
<223> OTHER INFORMATION: Humanized sequence.

<400> SEQUENCE: 172

```
Gln Val Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Thr Asp Gln
             20                  25                  30

Thr Ile His Trp Val Arg Gln Ala Pro Gly Gln Gly Leu Glu Trp Met
         35                  40                  45
```

Gly Tyr Ile Tyr Pro Arg Asp Asp Ser Pro Lys Tyr Asn Glu Asn Phe
            50                  55                  60

Lys Gly Arg Val Thr Leu Thr Ala Asp Lys Ser Thr Thr Ala Tyr
 65                  70                  75                  80

Met Glu Leu Ser Ser Leu Arg Ser Glu Asp Thr Ala Val Tyr Phe Cys
                85                  90                  95

Ala Arg Pro Asp Arg Ser Gly Tyr Ala Trp Phe Ile Tyr Trp Gly Gln
                100                 105                 110

Gly Thr Leu Val Thr Val Ser Ser
            115                 120

<210> SEQ ID NO 173
<211> LENGTH: 642
<212> TYPE: DNA
<213> ORGANISM: Artificial Sequence
<220> FEATURE:
<223> OTHER INFORMATION: Humanized sequence.

<400> SEQUENCE: 173
gacatccaga tgacccagag cccaagcagc ctgagcgcca gcgtgggcga ccgcgtgacc      60
atcacctgca aggccagccg cgacgtggcc atcgccgtgg cctggtacca gcagaagcca     120
ggcaaggtgc caaagctgct gatctactgg gccagcaccc gccacaccgg cgtgccaagc     180
cgcttcagcg gcagcggcag ccgcaccgac ttcaccctga ccatcagcag cctgcagcca     240
gaggacgtgg ccgactactt ctgccaccag tacagcagct acccattcac cttcggcagc     300
ggcaccaagc tggagatcaa gcgtactgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gt                       642

<210> SEQ ID NO 174
<211> LENGTH: 214
<212> TYPE: PRT
<213> ORGANISM: Artificial Sequence
<220> FEATURE:
<223> OTHER INFORMATION: Humanized sequence.

<400> SEQUENCE: 174

Asp Ile Gln Met Thr Gln Ser Pro Ser Ser Leu Ser Ala Ser Val Gly
 1               5                  10                  15

Asp Arg Val Thr Ile Thr Cys Lys Ala Ser Arg Asp Val Ala Ile Ala
                20                  25                  30

Val Ala Trp Tyr Gln Gln Lys Pro Gly Lys Val Pro Lys Leu Leu Ile
            35                  40                  45

Tyr Trp Ala Ser Thr Arg His Thr Gly Val Pro Ser Arg Phe Ser Gly
        50                  55                  60

Ser Gly Ser Arg Thr Asp Phe Thr Leu Thr Ile Ser Ser Leu Gln Pro
 65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Arg Thr Val Ala Ala
                100                 105                 110

```
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 175
<211> LENGTH: 1347
<212> TYPE: DNA
<213> ORGANISM: Artificial Sequence
<220> FEATURE:
<223> OTHER INFORMATION: Humanized sequence.

<400> SEQUENCE: 175

```
caggtgcagc tggtgcagag cggcgccgag gtgaagaagc caggcagcag cgtgaaggtg      60
agctgcaagg ccagcggcta caccttcacc gaccagacca tccactggat gcgccaggcc     120
ccaggccagg gcctggagtg gatcggctac atctacccac gcgacgacag ccccaaagtac    180
aacgagaact tcaagggcaa ggtcaccatc accgccgaca gagcaccag caccgcctac      240
atggagctga gcagcctgcg cagcgaggac accgccgtgt actactgcgc catcccagac     300
cgcagcggct acgcctggtt catctactgg ggccagggca ccctggtgac cgtgagcagc     360
gcctccacca agggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tcgacaagag agttgagccc     660
aaatcttgtg acaaaactca cacatgccca ccgtgcccag caccagaagc tgctggggga     720
ccgtcagtct tcctcttccc cccaaaaccc aaggacaccc tcatgatctc ccggacccct     780
gaggtcacat gcgtcgtggt ggacgtgagc cacgaagacc ctgaggtcaa gttcaactgg     840
tacgtggacg gcgtggaggt gcataatgcc aagacaaagc cgcgggagga gcagtacaac     900
agcacgtacc gtgtggtcag cgtcctcacc gtcctgcacc aggactggct gaatggcaag     960
gagtacaagt gcaaggtctc caacaaagcc ctcccagccc ccatcgagaa aaccatctcc    1020
aaagccaaag gcagcccccg agaaccacag gtgtacaccc tgcccccatc ccgggaggag    1080
atgaccaaga accaggtcag cctgacctgc ctggtcaaag gcttctatcc cagcgacatc    1140
gccgtggagt gggagagcaa tgggcagccg gagaacaact acaagaccac gcctcccgtg    1200
ctggactccg acggctcctt cttcctctac agcaagctca ccgtggacaa gagcaggtgg    1260
cagcagggga acgtcttctc atgctccgtg atgcatgagg ctctgcacaa ccactacacg    1320
cagaagagcc tctccctgtc tccgggt                                        1347
```

<210> SEQ ID NO 176

<211> LENGTH: 449
<212> TYPE: PRT
<213> ORGANISM: Artificial Sequence
<220> FEATURE:
<223> OTHER INFORMATION: Humanized sequence.

<400> SEQUENCE: 176

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Gln
            20                  25                  30

Thr Ile His Trp Met Arg Gln Ala Pro Gly Gln Gly Leu Glu Trp Ile
        35                  40                  45

Gly Tyr Ile Tyr Pro Arg Asp Asp Ser Pro Lys Tyr Asn Glu Asn Phe
    50                  55                  60

Lys Gly Lys Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ile Pro Asp Arg Ser Gly Tyr Ala Trp Phe Ile Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380
```

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
        435                 440                 445

Gly

<210> SEQ ID NO 177
<211> LENGTH: 1347
<212> TYPE: DNA
<213> ORGANISM: Artificial Sequence
<220> FEATURE:
<223> OTHER INFORMATION: Humanized sequence.

<400> SEQUENCE: 177
caggtgcagc tggtgcagag cggcgccgag gtgaagaagc caggcagcag cgtgaaggtg      60
agctgcaagg ccagcggctt caccttcacc gaccagacca tccactgggt gcgccaggcc     120
ccaggccagg gcctggagtg gatgggctac atctacccac gcgacgacag cccaaagtac     180
aacgagaact tcaagggcaa ggtcaccctg accgccgaca gagccaccag caccgcctac     240
atggagctga gcagcctgcg cagcgaggac accgccgtgt actactgcgc catcccagac     300
cgcagcggct acgcctggtt catctactgg ggccagggca ccctggtgac cgtgagcagc     360
gcctccacca agggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tcgacaagag agttgagccc     660
aaatcttgtg acaaaactca cacatgccca ccgtgcccag caccagaagc tgctggggga     720
ccgtcagtct tcctcttccc cccaaaaccc aaggacaccc tcatgatctc ccggaccccc     780
gaggtcacat gcgtcgtggt ggacgtgagc cacgaagacc ctgaggtcaa gttcaactgg     840
tacgtggacg gcgtggaggt gcataatgcc aagacaaagc cgcgggagga gcagtacaac     900
agcacgtacc gtgtggtcag cgtcctcacc gtcctgcacc aggactggct gaatggcaag     960
gagtacaagt gcaaggtctc caacaaagcc ctcccagccc ccatcgagaa aaccatctcc    1020
aaagccaaag gcagccccg agaaccacag gtgtacaccc tgcccccatc ccgggaggag    1080
atgaccaaga accaggtcag cctgacctgc ctggtcaaag gcttctatcc cagcgacatc    1140
gccgtggagt gggagagcaa tgggcagccg gagaacaact acaagaccac gcctcccgtg    1200
ctggactccg acggctcctt cttcctctac agcaagctca ccgtggacaa gagcaggtgg    1260
cagcagggga acgtcttctc atgctccgtg atgcatgagg ctctgcacaa ccactacacg    1320
cagaagagcc tctccctgtc tccgggt                                        1347

<210> SEQ ID NO 178
<211> LENGTH: 449
<212> TYPE: PRT
<213> ORGANISM: Artificial Sequence
<220> FEATURE:
<223> OTHER INFORMATION: Humanized sequence.
```

-continued

```
<400> SEQUENCE: 178

Gln Val Gln Leu Val Gln Ser Gly Ala Glu Val Lys Lys Pro Gly Ser
  1               5                  10                  15

Ser Val Lys Val Ser Cys Lys Ala Ser Gly Phe Thr Phe Thr Asp Gln
             20                  25                  30

Thr Ile His Trp Val Arg Gln Ala Pro Gly Gln Gly Leu Glu Trp Met
         35                  40                  45

Gly Tyr Ile Tyr Pro Arg Asp Asp Ser Pro Lys Tyr Asn Glu Asn Phe
     50                  55                  60

Lys Gly Lys Val Thr Leu Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Ile Pro Asp Arg Ser Gly Tyr Ala Trp Phe Ile Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415
```

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly

<210> SEQ ID NO 179
<211> LENGTH: 642
<212> TYPE: DNA
<213> ORGANISM: Artificial Sequence
<220> FEATURE:
<223> OTHER INFORMATION: Humanized sequence.

<400> SEQUENCE: 179
gacatccaga tgacccagag cccaagcagc ctgagcgcca gcgtgggcga ccgcgtgacc    60
atcacctgca aggccagccg cgacgtggcc atcgccgtgg cctggtacca gcagaagcca   120
ggcaaggtgc caaagctgct gctgttctgg gccagcaccc gccacaccgg cgtgccagac   180
cgcttcagcg gcagcggcag cggcaccgac ttcaccctga ccatcagcag cctgcagcca   240
gaggacctgg ccgactacta ctgccaccag tacagcagct acccattcac cttcggccag   300
ggcaccaagc tggagatcaa gcgtactgtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga aaacacaaaa gtctacgcct gcgaagtcac ccatcagggc   600
ctgagctcgc ccgtcacaaa gagcttcaac aggggagagt gt                      642

<210> SEQ ID NO 180
<211> LENGTH: 214
<212> TYPE: PRT
<213> ORGANISM: Artificial Sequence
<220> FEATURE:
<223> OTHER INFORMATION: Humanized sequence.

<400> SEQUENCE: 180

Asp Ile Gln Met Thr Gln Ser Pro Ser Ser Leu Ser Ala Ser Val Gly
 1               5                   10                  15

Asp Arg Val Thr Ile Thr Cys Lys Ala Ser Arg Asp Val Ala Ile Ala
                20                  25                  30

Val Ala Trp Tyr Gln Gln Lys Pro Gly Lys Val Pro Lys Leu Leu Leu
            35                  40                  45

Phe Trp Ala Ser Thr Arg His Thr Gly Val Pro Asp Arg Phe Ser Gly
        50                  55                  60

Ser Gly Ser Gly Thr Asp Phe Thr Leu Thr Ile Ser Ser Leu Gln Pro
65                  70                  75                  80

Glu Asp Leu Ala Asp Tyr Tyr Cys His Gln Tyr Ser Ser Tyr Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln

```
              145                 150                 155                 160
Glu Ser Val Thr Glu Gln Asp Ser Lys Asp Ser Thr Tyr Ser Leu Ser
                    165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
            210

<210> SEQ ID NO 181
<211> LENGTH: 189
<212> TYPE: PRT
<213> ORGANISM: Homo sapiens

<400> SEQUENCE: 181

Met Leu Gly Ser Arg Ala Val Met Leu Leu Leu Leu Pro Trp Thr
 1               5                  10                  15

Ala Gln Gly Arg Ala Val Pro Gly Gly Ser Ser Pro Ala Trp Thr Gln
                20                  25                  30

Cys Gln Gln Leu Ser Gln Lys Leu Cys Thr Leu Ala Trp Ser Ala His
                35                  40                  45

Pro Leu Val Gly His Met Asp Leu Arg Glu Glu Gly Asp Glu Glu Thr
    50                  55                  60

Thr Asn Asp Val Pro His Ile Gln Cys Gly Asp Gly Cys Asp Pro Gln
65                  70                  75                  80

Gly Leu Arg Asp Asn Ser Gln Phe Cys Leu Gln Arg Ile His Gln Gly
                85                  90                  95

Leu Ile Phe Tyr Glu Lys Leu Leu Gly Ser Asp Ile Phe Thr Gly Glu
                100                 105                 110

Pro Ser Leu Leu Pro Asp Ser Pro Val Gly Gln Leu His Ala Ser Leu
            115                 120                 125

Leu Gly Leu Ser Gln Leu Leu Gln Pro Glu Gly His His Trp Glu Thr
        130                 135                 140

Gln Gln Ile Pro Ser Leu Ser Pro Ser Gln Pro Trp Gln Arg Leu Leu
145                 150                 155                 160

Leu Arg Phe Lys Ile Leu Arg Ser Leu Gln Ala Phe Val Ala Val Ala
                165                 170                 175

Ala Arg Val Phe Ala His Gly Ala Ala Thr Leu Ser Pro
            180                 185
```

ANTI-IL-23 ANTIBODIES

RELATED APPLICATIONS

This application is a divisional of U.S. application Ser. No. 14/302,986, filed Jun. 12, 2014, now U.S. Pat. No. 9,441,036 issued on Sep. 13, 2016, which is a divisional of U.S. application Ser. No. 13/287,208, filed Nov. 2, 2011, now U.S. Pat. No. 8,778,346 issued on Jul. 15, 2014, which claims the benefit of U.S. Provisional Application 61/448,785, filed Mar. 3, 2011, U.S. Provisional Application 61/412,594, filed Nov. 11, 2010, U.S. Provisional Application 61/411,953, filed Nov. 10, 2010, and U.S. Provisional Application 61/410,158, filed Nov. 4, 2010, the disclosure of each of which is herein incorporated by reference in its entirety.

TECHNICAL FIELD OF THE INVENTION

This invention generally relates to anti-IL-23p19 antibodies for diagnostic and therapeutic use. More specifically, humanized anti-IL-23p19 antibodies and methods of use for the treatment of various diseases or disorders are disclosed. Pharmaceutical compositions and kits comprising such compounds are also disclosed.

BACKGROUND OF THE INVENTION

Higher eukaryotes have evolved an intricate response to pathogens that is initiated by the innate immune response and followed by the adaptive immune response. Together these two mechanisms not only eradicate pathogens that infect the organism but also establish a long term immunological response against future exposures. Deficiencies in these responses can result in increased susceptibility to infections and/or alterations of the adaptive immune response leading to chronic inflammation and autoimmunity. IL-12, a heterodimeric cytokine consisting of a p40 and a p35 protein subunit, has long been considered the hallmark cytokine of the innate immune response with major influence on adaptive immunity. However, data from investigation of this cytokine's biological role led to confusing results. For example, while p40-deficient mice were resistant to Collagen Induced Arthritis (CIA) and Experimental Autoimmune Encephalomyelitis (EAE), p35-deficient mice were susceptible to both and even displayed exacerbated disease. Such conundrums began to be resolved with the discovery in the late 1990's of a new member of the IL-12 cytokine family with a distinct role in the immune response—IL-23.

IL-23 is composed of a common subunit (p40) with IL-12 and a unique p19 subunit. Despite this shared p40 subunit, the roles for IL-23 and IL-12 are quite different. IL-12 is important for Th1 responses via promotion of Th1 cell differentiation, proliferation and activation. In contrast, IL-23 supports the development and maintenance of a recently defined set of CD4$^+$ T helper cells termed Th17 cells due to their ability to produce IL-17 and related cytokines. There is mounting evidence that IL-23 is involved in chronic autoimmune inflammation and the modulation of IL-23 activity could provide promising therapies against autoimmune diseases.

There is therefore a need for antagonist molecules against IL-23 with beneficial pharmacological properties, which can be used as therapeutic agents to treat diseases, in particular immunological and autoimmune diseases in humans.

Accordingly, one aim of the present invention is to provide anti-IL-23 antagonist molecules, in particular anti-IL-23 antagonist molecules which have high binding affinity to IL-23.

A further aim of the present invention is to provide anti-IL-23 antagonist molecules, which have high specificity for IL-23.

A further aim of the present invention is to provide anti-IL-23 antagonists, which have high blocking activity for the association of IL-23 and its receptor.

A further aim of the present invention is to provide anti-IL-23 antagonists, which have potent cellular activity.

A further aim of the present invention is to provide anti-IL-23 antagonists, which have a favorable bioavailability.

A further aim of the present invention is to provide anti-IL-23 antagonists, which have favorable biophysical properties.

Further aims of the present invention include combinations of any of the aims set forth above.

SUMMARY OF THE INVENTION

The present invention addresses the above needs and provides antibodies that bind to the p19 subunit of the IL-23 protein. In one aspect, an antibody of the present invention binds to human IL-23 with high affinity. In another aspect, an antibody of the present invention inhibits the IL-23 stimulated production of IL-17 from mouse splenocytes. In another aspect, an antibody of the present invention does not bind to nor antagonize IL-12, which is a closely related family member to IL-23.

In one embodiment, the present invention provides anti-IL-23p19 antibodies that are derived from mouse hybridomas, for example monoclonal antibodies. In one embodiment, the present invention provides full length anti-IL-23p19 antibodies. In another embodiment, the present invention provides anti-IL-23p19 humanized antibodies, for example humanized monoclonal anti-IL-23p19 antibodies, for example full length humanized monoclonal anti-IL-23p19 antibodies. In one aspect, a humanized antibody of the present invention binds to human IL-23 with high affinity. In another aspect, a humanized antibody of the present invention also binds to cynomolgus IL-23 with high affinity. In a further aspect, a humanized antibody of the present invention inhibits IL-23-induced STAT3 phosphorylation in DB cells. In another aspect, a humanized antibody of the present invention antagonizes the action of IL-23 by binding to the p19 subunit of IL-23, for example as measured by the inhibition of cytokines such as IL-17 and IL-22, whose production is stimulated by IL-23. In a further aspect, a humanized antibody of the present invention has a favorable pharmacokinetic (PK) profile. In a further aspect, a humanized antibody of the present invention has favorable biophysical properties, such as quality, stability or solubility, for example as defined by the percentage of antibody in monomer form.

Further embodiments encompass DNA molecules encoding antibodies of the present invention, expression vectors and host cells comprising such DNA molecules, and methods of making antibodies of the present invention. The present invention further provides therapeutic uses for the antibodies of the present invention, in particular against immunological and autoimmune diseases.

In one embodiment, the present invention further provides an anti-IL-23p19 antibody or antigen-binding fragment thereof comprising a light chain CDR1 (L-CDR1) sequence of SEQ ID NO:1, 4, 6, 7, 8, 11, 15, 18, 19, 22, 27 or 30; a light chain CDR2 (L-CDR2) sequence of SEQ ID NO:2, 5, 9, 12, 16, 20, 23, 25, 28 or 31; a light chain CDR3 (L-CDR3) sequence of SEQ ID NO:3, 10, 13, 14, 17, 21, 24, 26, 29, or 32; a heavy chain CDR1 (H-CDR1) sequence of SEQ ID NO:33, 36, 38, 40, 43, 45, 48, 51, 54, 57, 60, 63, 66, 67, 68, 69, 77 or 80; a heavy chain CDR2 (H-CDR2) sequence of SEQ ID NO:34, 39, 41, 46, 49, 52, 55, 58, 61, 64, 70, 72, 73, 75, 78 or 81; and a heavy chain CDR3 (H-CDR3) sequence of SEQ ID NO:35, 37, 42, 44, 47, 50, 53, 56, 59, 62, 65, 71, 74, 76, 79 or 82. In one embodiment, the anti-IL-23p19 antibody or antigen-binding fragment thereof comprises a light chain variable region comprising a L-CDR1 listed above, a L-CDR2 listed above and a L-CDR3 listed above, and a heavy chain variable region comprising a H-CDR1 listed above, a H-CDR2 listed above and a H-CDR3 listed above.

In one embodiment, the present invention further provides an anti-IL-23p19 antibody or antigen-binding fragment thereof, wherein the antibody or antigen-binding fragment thereof comprises a L-CDR1, a L-CDR2, a L-CDR3, a H-CDR1, a H-CDR2 and a H-CDR3 sequence of SEQ ID NO:1, 2, 3, 33, 34, and 35, respectively; or a L-CDR1, a L-CDR2, a L-CDR3, a H-CDR1, a H-CDR2 and a H-CDR3 sequence of SEQ ID NO:4, 5, 3, 36, 34 and 37, respectively; or a L-CDR1, a L-CDR2, a L-CDR3, a H-CDR1, a H-CDR2 and a H-CDR3 sequence of SEQ ID NO:1, 2, 3, 38, 39 and 35, respectively; or a L-CDR1, a L-CDR2, a L-CDR3, a H-CDR1, a H-CDR2 and a H-CDR3 sequence of SEQ ID NO:6, 2, 3, 40, 41 and 42, respectively; or a L-CDR1, a L-CDR2, a L-CDR3, a H-CDR1, a H-CDR2 and a H-CDR3 sequence of SEQ ID NO:7, 2, 3, 43, 41 and 44, respectively; or a L-CDR1, a L-CDR2, a L-CDR3, a H-CDR1, a H-CDR2 and a H-CDR3 sequence of SEQ ID NO:8, 9, 10, 45, 46 and 47, respectively; or a L-CDR1, a L-CDR2, a L-CDR3, a H-CDR1, a H-CDR2 and a H-CDR3 sequence of SEQ ID NO:8, 9, 10, 48, 49 and 50, respectively; or a L-CDR1, a L-CDR2, a L-CDR3, a H-CDR1, a H-CDR2 and a H-CDR3 sequence of SEQ ID NO:11, 12, 13, 51, 52 and 53, respectively; or a L-CDR1, a L-CDR2, a L-CDR3, a H-CDR1, a H-CDR2 and a H-CDR3 sequence of SEQ ID NO:7, 2, 14, 54, 55 and 56, respectively; or a L-CDR1, a L-CDR2, a L-CDR3, a H-CDR1, a H-CDR2 and a H-CDR3 sequence of SEQ ID NO:15, 16, 17, 57, 58 and 59, respectively; or a L-CDR1, a L-CDR2, a L-CDR3, a H-CDR1, a H-CDR2 and a H-CDR3 sequence of SEQ ID NO:18, 16, 17, 60, 61 and 62, respectively; or a L-CDR1, a L-CDR2, a L-CDR3, a H-CDR1, a H-CDR2 and a H-CDR3 sequence of SEQ ID NO:19, 20, 21, 63, 66, 67 or 68, 64 and 65, respectively; or a L-CDR1, a L-CDR2, a L-CDR3, a H-CDR1, a H-CDR2 and a H-CDR3 sequence of SEQ ID NO:22, 23, 24, 69, 70 and 71, respectively; or a L-CDR1, a L-CDR2, a L-CDR3, a H-CDR1, a H-CDR2 and a H-CDR3 sequence of SEQ ID NO:22, 25, 26, 55, 72 and 71, respectively; or a L-CDR1, a L-CDR2, a L-CDR3, a H-CDR1, a H-CDR2 and a H-CDR3 sequence of SEQ ID NO:8, 9, 10, 45, 73 and 74, respectively; or a L-CDR1, a L-CDR2, a L-CDR3, a H-CDR1, a H-CDR2 and a H-CDR3 sequence of SEQ ID NO:27, 28, 29, 45, 75 and 76, respectively; or a L-CDR1, a L-CDR2, a L-CDR3, a H-CDR1, a H-CDR2 and a H-CDR3 sequence of SEQ ID NO:8, 9, 10, 77, 78 and 79, respectively; or a L-CDR1, a L-CDR2, a L-CDR3, a H-CDR1, a H-CDR2 and a H-CDR3 sequence of SEQ ID NO:30, 31, 32, 80, 81 and 82, respectively. In one embodiment, the anti-IL-23p19 antibody or antigen-binding fragment thereof comprises a light chain variable region comprising a L-CDR1, L-CDR2 and L-CDR3 combination listed above, and a heavy chain variable region comprising a H-CDR1, H-CDR2 and H-CDR3 combination listed above.

In one embodiment, the present invention further provides an anti-IL-23p19 antibody or antigen-binding fragment thereof, wherein the antibody or antigen-binding fragment thereof comprises a light chain variable region comprising the amino acid sequence of SEQ ID NO:84 and a heavy chain variable region comprising the amino acid sequence SEQ ID NO:121; or a light chain variable region comprising the amino acid sequence of SEQ ID NO:86 and a heavy chain variable region comprising the amino acid sequence SEQ ID NO:123; or a light chain variable region comprising the amino acid sequence of SEQ ID NO:88 and a heavy chain variable region comprising the amino acid sequence SEQ ID NO:125; or a light chain variable region comprising the amino acid sequence of SEQ ID NO:90 and a heavy chain variable region comprising the amino acid sequence SEQ ID NO:127; or a light chain variable region comprising the amino acid sequence of SEQ ID NO:91 and a heavy chain variable region comprising the amino acid sequence SEQ ID NO:128; or a light chain variable region comprising the amino acid sequence of SEQ ID NO:93 and a heavy chain variable region comprising the amino acid sequence SEQ ID NO:130; or a light chain variable region comprising the amino acid sequence of SEQ ID NO:95 and a heavy chain variable region comprising the amino acid sequence SEQ ID NO:132; or a light chain variable region comprising the amino acid sequence of SEQ ID NO:97 and a heavy chain variable region comprising the amino acid sequence SEQ ID NO:134; or a light chain variable region comprising the amino acid sequence of SEQ ID NO:99 and a heavy chain variable region comprising the amino acid sequence SEQ ID NO:136; or a light chain variable region comprising the amino acid sequence of SEQ ID NO:101 and a heavy chain variable region comprising the amino acid sequence SEQ ID NO:138; or a light chain variable region comprising the amino acid sequence of SEQ ID NO:103 and a heavy chain variable region comprising the amino acid sequence SEQ ID NO:140; or a light chain variable region comprising the amino acid sequence of SEQ ID NO:105 and a heavy chain variable region comprising the amino acid sequence SEQ ID NO:142; or a light chain variable region comprising the amino acid sequence of SEQ ID NO:107 and a heavy chain variable region comprising the amino acid sequence SEQ ID NO:144; or a light chain variable region comprising the amino acid sequence of SEQ ID NO:109 and a heavy chain variable region comprising the amino acid sequence SEQ ID NO:146; or a light chain variable region comprising the amino acid sequence of SEQ ID NO:111 and a heavy chain variable region comprising the amino acid sequence SEQ ID NO:148; or a light chain variable region comprising the amino acid sequence of SEQ ID NO:113 and a heavy chain variable region comprising the amino acid sequence SEQ ID NO:150; or a light chain variable region comprising the amino acid sequence of SEQ ID NO:115 and a heavy chain variable region comprising the amino acid sequence SEQ ID NO:152; or a light chain variable region comprising the amino acid sequence of SEQ ID NO:117 and a heavy chain variable region comprising the amino acid sequence SEQ ID NO:154; or a light chain variable region comprising the amino acid sequence of SEQ ID NO:119 and a heavy chain variable region comprising the amino acid sequence SEQ ID NO:156.

In one embodiment, the present invention further provides an anti-IL-23p19 antibody or antigen-binding fragment thereof, wherein the antibody or antigen-binding fragment thereof comprises a light chain variable region comprising an amino acid sequence selected from the group consisting of SEQ ID NO:158, 160, 162 and 164 and a heavy chain variable region comprising an amino acid sequence selected from the group consisting of SEQ ID NO:166, 168, 170 and 172.

In one embodiment, the present invention further provides an anti-IL-23p19 antibody or antigen-binding fragment thereof, wherein the antibody or antigen-binding fragment thereof has a $K_D$ for IL-23 of less than 40 pM, or a $K_D$ for IL-23 of less than 20 pM, or $K_D$ for IL-23 of less than 10 pM or $K_D$ for IL-23 of less than 1 pM.

In a further embodiment, the present invention provides an anti-IL-23p19 antibody or antigen-binding fragment thereof that binds to human IL-23p19 at an epitope consisting of amino acid residues 108 to 126 and amino acid residues 137 to 151 of SEQ ID NO: 181.

In a further embodiment, the present invention provides an anti-IL-23p19 antibody or antigen-binding fragment thereof that competitively binds to human IL-23p19 with an antibody of the present invention. In one embodiment, the present invention provides an anti-IL-23p19 antibody or antigen-binding fragment thereof that competitively binds to human IL-23p19 with a humanized monoclonal anti-IL-23p19 antibody comprising a light chain comprising the amino acid sequence of SEQ ID NO:174 and a heavy chain comprising the amino acid sequence of SEQ ID NO:176. In one embodiment, the present invention provides an anti-IL-23p19 antibody or antigen-binding fragment thereof that competitively binds to human IL-23p19 with a humanized monoclonal anti-IL-23p19 antibody comprising a light chain comprising the amino acid sequence of SEQ ID NO:174 and a heavy chain comprising the amino acid sequence of SEQ ID NO:178. In one embodiment, the present invention provides an anti-IL-23p19 antibody or antigen-binding fragment thereof that competitively binds to human IL-23p19 with a humanized monoclonal anti-IL-23p19 antibody comprising a light chain comprising the amino acid sequence of SEQ ID NO:180 and a heavy chain comprising the amino acid sequence of SEQ ID NO:176. In one embodiment, the present invention provides an anti-IL-23p19 antibody or antigen-binding fragment thereof that competitively binds to human IL-23p19 with a humanized monoclonal anti-IL-23p19 antibody comprising a light chain comprising the amino acid sequence of SEQ ID NO: 180 and a heavy chain comprising the amino acid sequence of SEQ ID NO: 178.

In one embodiment, the anti-IL-23p19 antibody is a humanized antibody. In one embodiment, the anti-IL-23p19 antibody is a monoclonal antibody. In one embodiment, the anti-IL-23p19 antibody is a full length antibody. In one embodiment, the anti-IL-23p19 antibody is a humanized monoclonal antibody, for example a full length humanized monoclonal antibody. In one embodiment the antigen-binding fragment is a Fab, F(ab')$_2$, or single chain Fv fragment. In one embodiment, the antigen-binding fragment comprises a light chain variable region and a heavy chain variable region.

In one embodiment, the present invention further provides an anti-IL-23p19 antibody or antigen-binding fragment thereof, wherein the antibody or antigen-binding fragment thereof comprises the amino acid sequence of SEQ ID NO:19 (CDR1-L); the amino acid sequence of SEQ ID NO:20 (CDR2-L); the amino acid sequence of SEQ ID NO:21 (CDR3-L): the amino acid sequence of SEQ ID NO:63, 66, 67 or 68 (CDR1-H); the amino acid sequence of SEQ ID NO:64 (CDR2-H); and the amino acid sequence of SEQ ID NO:65 (CDR3-H).

In one embodiment, the present invention further provides an anti-IL-23p19 antibody or antigen-binding fragment thereof, wherein the antibody or antigen-binding fragment thereof comprises the amino acid sequence of SEQ ID NO:19 (CDR1-L); the amino acid sequence of SEQ ID NO:20 (CDR2-L); the amino acid sequence of SEQ ID NO:21 (CDR3-L): the amino acid sequence of SEQ ID NO:66 (CDR1-H); the amino acid sequence of SEQ ID NO:64 (CDR2-H); and the amino acid sequence of SEQ ID NO:65 (CDR3-H).

In one embodiment, the present invention further provides an anti-IL-23p19 antibody or antigen-binding fragment thereof, wherein the antibody or antigen-binding fragment thereof comprises a light chain variable region comprising the amino acid sequence of SEQ ID NO:19 (CDR1-L); the amino acid sequence of SEQ ID NO:20 (CDR2-L); and the amino acid sequence of SEQ ID NO:21 (CDR3-L); and a heavy chain variable region comprising the amino acid sequence of SEQ ID NO: 63, 66, 67 or 68 (CDR1-H); the amino acid sequence of SEQ ID NO:64 (CDR2-H); and the amino acid sequence of SEQ ID NO:65 (CDR3-H).

In one embodiment, the present invention further provides an anti-IL-23p19 or antigen-binding fragment thereof antibody, wherein the antibody or antigen-binding fragment thereof comprises a light chain variable region comprising the amino acid sequence of SEQ ID NO:19 (CDR1-L); the amino acid sequence of SEQ ID NO:20 (CDR2-L); and the amino acid sequence of SEQ ID NO:21 (CDR3-L); and a heavy chain variable region comprising the amino acid sequence of SEQ ID NO:66 (CDR1-H); the amino acid sequence of SEQ ID NO:64 (CDR2-H); and the amino acid sequence of SEQ ID NO:65 (CDR3-H).

In one embodiment, the present invention further provides an anti-IL-23p19 antibody or antigen-binding fragment thereof, wherein the antibody or antigen-binding fragment thereof comprises a light chain variable region comprising the amino acid sequence of any one of SEQ ID NO:158, 160, 162 or 164; and a heavy chain variable region comprising the amino acid sequence any one of SEQ ID NO:166, 168, 170 or 172.

In one embodiment, the present invention further provides an anti-IL-23p19 antibody or antigen-binding fragment thereof, wherein the antibody or antigen-binding fragment thereof comprises a light chain variable region comprising the amino acid sequence of SEQ ID NO:160 and a heavy chain variable region comprising the amino acid sequence SEQ ID NO:166.

In one embodiment, the present invention further provides an anti-IL-23p19 antibody or antigen-binding fragment thereof, wherein the antibody or antigen-binding fragment thereof comprises a light chain variable region comprising the amino acid sequence of SEQ ID NO:160 and a heavy chain variable region comprising the amino acid sequence SEQ ID NO:168.

In one embodiment, the present invention further provides an anti-IL-23p19 antibody or antigen-binding fragment thereof, wherein the antibody or antigen-binding fragment thereof comprises a light chain variable region comprising the amino acid sequence of SEQ ID NO:158 and a heavy chain variable region comprising the amino acid sequence SEQ ID NO:166.

In one embodiment, the present invention further provides an anti-IL-23p19 antibody or antigen-binding fragment thereof, wherein the antibody or antigen-binding fragment thereof comprises a light chain variable region comprising the amino acid sequence of SEQ ID NO:158 and a heavy chain variable region comprising the amino acid sequence SEQ ID NO:168.

In one embodiment, the anti-IL-23p19 antibody is a humanized antibody. In one embodiment, the anti-IL-23p19 antibody is a monoclonal antibody. In one embodiment, the anti-IL-23p19 antibody is a full length antibody. In one embodiment, the anti-IL-23p19 antibody is a humanized monoclonal anti-IL-23p19 antibody, for example a full length humanized monoclonal antibody. In one embodiment, the antigen-binding fragment is a Fab, F(ab')$_2$, or single chain Fv fragment. In one embodiment, the antigen-binding fragment comprises a light chain variable region and a heavy chain variable region.

In one embodiment, the present invention further provides an antibody comprising the amino acid sequence SEQ ID NO:166 or 168 linked to a human IgG1, IgG2, IgG3, IgG4, IgM, IgA or IgE heavy chain constant region. An antibody comprising the amino acid sequence of SEQ ID NO: 166 or 168 linked to a human IgG1 heavy chain constant region. An antibody comprising the amino acid sequence of SEQ ID NO:158 or 160 linked to a human kappa or lambda light chain constant region. An antibody comprising the amino acid sequence of SEQ ID NO: 158 or 160 linked to a human kappa light chain constant region.

In one embodiment, the present invention further provides an antibody comprising the amino acid sequence of SEQ ID NO:166 or 168 linked to a human IgG1 heavy chain constant region; and the amino acid sequence of SEQ ID NO:158 or 160 linked to a human kappa light chain constant region.

In one embodiment, the present invention further provides a humanized monoclonal anti-IL-23p19 antibody comprising a light chain variable region comprising the amino acid sequence selected from the group consisting of any one of SEQ ID NO:158, 160, 162 and 164 and a heavy chain variable region comprising the amino acid sequence selected from the group consisting of any one of SEQ ID NO:166, 168, 170 and 172.

In one embodiment, the present invention further provides a humanized monoclonal anti-IL-23p19 antibody comprising a light chain variable region comprising the amino acid sequence of SEQ ID NO:160 and a heavy chain variable region comprising the amino acid sequence SEQ ID NO:166.

In one embodiment, the present invention further provides a humanized monoclonal anti-IL-23p19 antibody comprising a light chain variable region comprising the amino acid sequence of SEQ ID NO:160 and a heavy chain variable region comprising the amino acid sequence SEQ ID NO:168.

In one embodiment, the present invention further provides a humanized monoclonal anti-IL-23p19 antibody comprising a light chain variable region comprising the amino acid sequence of SEQ ID NO:158 and a heavy chain variable region comprising the amino acid sequence SEQ ID NO:166.

In one embodiment, the present invention further provides a humanized monoclonal anti-IL-23p19 antibody comprising a light chain variable region comprising the amino acid sequence of SEQ ID NO:158 and a heavy chain variable region comprising the amino acid sequence SEQ ID NO:168.

In one embodiment, the present invention further provides a humanized monoclonal anti-IL-23p19 antibody comprising a light chain comprising the amino acid sequence of SEQ ID NO:174 or 180 and a heavy chain comprising the amino acid sequence of SEQ ID NO:176 or 178.

In one embodiment, the present invention further provides a humanized monoclonal anti-IL-23p19 antibody comprising a light chain comprising the amino acid sequence of SEQ ID NO:174 and a heavy chain comprising the amino acid sequence of SEQ ID NO:176.

In one embodiment, the present invention further provides a humanized monoclonal anti-IL-23p19 antibody comprising a light chain comprising the amino acid sequence of SEQ ID NO:174 and a heavy chain comprising the amino acid sequence of SEQ ID NO:178.

In one embodiment, the present invention further provides a humanized monoclonal anti-IL-23p19 antibody comprising a light chain comprising the amino acid sequence of SEQ ID NO:180 and a heavy chain comprising the amino acid sequence of SEQ ID NO:176.

In one embodiment, the present invention further provides a humanized monoclonal anti-IL-23p19 antibody comprising a light chain comprising the amino acid sequence of SEQ ID NO: 180 and a heavy chain comprising the amino acid sequence of SEQ ID NO: 178.

In a further embodiment, the present invention relates to an anti-IL-23p19 antibody or antigen-binding fragment thereof comprising a humanized light chain variable domain comprising the CDRs of SEQ ID NO:160 and framework regions having an amino acid sequence at least 90% identical to the amino acid sequence of the framework regions of the variable domain light chain amino acid sequence of SEQ ID NO:160 and a humanized heavy chain variable domain comprising the CDRs of SEQ ID NO:166 and framework regions having an amino acid sequence at least 90% identical to the amino acid sequence of the framework regions of the variable domain heavy chain amino acid sequence of SEQ ID NO:166. In one embodiment, the anti-IL-23p19 antibody is a humanized monoclonal antibody, for example a full length humanized monoclonal antibody.

In a further embodiment, the present invention relates to an anti-IL-23p19 antibody or antigen-binding fragment thereof comprising a humanized light chain variable domain comprising the CDRs of SEQ ID NO:160 and framework regions having an amino acid sequence at least 90% identical to the amino acid sequence of the framework regions of the variable domain light chain amino acid sequence of SEQ ID NO:160 and a humanized heavy chain variable domain comprising the CDRs of SEQ ID NO:168 and framework regions having an amino acid sequence at least 90% identical to the amino acid sequence of the framework regions of the variable domain heavy chain amino acid sequence of SEQ ID NO:168. In one embodiment, the anti-IL-23p19 antibody is a humanized monoclonal antibody, for example a full length humanized monoclonal antibody.

In a further embodiment, the present invention relates to an anti-IL-23p19 antibody or antigen-binding fragment thereof comprising a humanized light chain variable domain comprising the CDRs of SEQ ID NO:158 and framework regions having an amino acid sequence at least 90% identical to the amino acid sequence of the framework regions of the variable domain light chain amino acid sequence of SEQ ID NO:158 and a humanized heavy chain variable domain comprising the CDRs of SEQ ID NO:166 and framework regions having an amino acid sequence at least 90% identical to the amino acid sequence of the framework regions of the variable domain heavy chain amino acid sequence of SEQ ID NO:166. In one embodiment, the anti-IL-23p19 antibody is a humanized monoclonal antibody, for example a full length humanized monoclonal antibody.

In a further embodiment, the present invention relates to an anti-IL-23p19 antibody or antigen-binding fragment thereof comprising a humanized light chain variable domain comprising the CDRs of SEQ ID NO:158 and framework regions having an amino acid sequence at least 90% identical to the amino acid sequence of the framework regions of the variable domain light chain amino acid sequence of SEQ ID NO:158 and a humanized heavy chain variable domain comprising the CDRs of SEQ ID NO:168 and framework regions having an amino acid sequence at least 90% identical to the amino acid sequence of the framework regions of the variable domain heavy chain amino acid sequence of SEQ ID NO:168. In one embodiment, the anti-IL-23p19 antibody is a humanized monoclonal antibody, for example a full length humanized monoclonal antibody.

In one aspect, a humanized anti-IL-23p19 antibody of the present invention may be further characterized by a $K_D$ for human IL-23 equal or less than 1 pM. In one aspect, there is no shift in binding on-rate in 50% human serum.

In one aspect, a humanized anti-IL-23p19 antibody of the present invention may be further characterized in that it blocks IL-23 binding to human IL-23R/Fc in vitro.

In one aspect, a humanized anti-IL-23p19 antibody of the present invention may be further characterized in that it does not bind to human IL-12.

In one aspect, a humanized anti-IL-23p19 antibody of the present invention may be further characterized in that it inhibits human IL-23 induced IL-17 production in mouse splenocytes with $IC_{50}$'s equal or less than 20 pM.

In one aspect, a humanized anti-IL-23p19 antibody of the present invention may be further characterized in that it inhibits human IL-23 induced STAT3 phosphorylation in human DB cells with $IC_{50}$'s equal or less than 40 pM.

In one aspect, a humanized anti-IL-23p19 antibody of the present invention may be further characterized in that it has no predicted activity in ADCC/CDC.

In one aspect, a humanized anti-IL-23p19 antibody of the present invention may be further characterized in that it has a $K_D$ equal or less than_1 pM for cynomolgus monkey IL-23.

In one aspect, a humanized anti-IL-23p19 antibody of the present invention may be further characterized in that it has no cross reactivity to mouse or rat IL-23.

In one aspect, a humanized anti-IL-23p19 antibody of the present invention may be further characterized in that it inhibits human IL-23 induced IL-17 and IL-22 production in a mouse ear at 80% or greater inhibition of both cytokines at 1 mg/kg.

In one aspect, a humanized anti-IL-23p19 antibody of the present invention may be further characterized by a melting temperature of 83° C. as determined by differential scanning calorimetry.

In one aspect, a humanized anti-IL-23p19 antibody of the present invention may be further characterized by solubility equal or greater than 100 mg/ml, as measured by UV spectroscopy and monitored by turbidity.

In a further aspect, a humanized anti-IL-23p19 antibody of the present invention may be further characterized in that it is present in at least 90% monomer form, or in at least 92% monomer form, or in at least 95% monomer form in a buffer.

In a further aspect, a humanized anti-IL-23p19 antibody of the present invention may be further characterized in that it remains in at least 90% monomer form, or in at least 92% monomer form, or in at least 95% monomer form in a buffer for one month or for four months.

In one aspect, the humanized anti-IL-23p19 antibody is a humanized monoclonal antibody, for example a full length humanized monoclonal antibody.

Further embodiments encompass a DNA molecule encoding a variable light chain region above, a DNA molecule encoding a variable heavy chain region above, a DNA molecule encoding a light chain region above, or a DNA molecule encoding a heavy chain region above.

Further embodiments encompass an expression vector containing a DNA molecule above. In one embodiment, an expression vector comprises a DNA molecule encoding the constant heavy chain and/or the constant light chain, respectively, linked to the DNA molecule encoding the variable heavy chain and/or the variable light chain, respectively. Further embodiments encompass a host cell carrying one or more expression vectors above. In one embodiment, a host is a mammalian cell.

Further embodiments encompass a method for producing an antibody or antigen-binding fragment thereof above comprising transfecting a mammalian host cell with one or more of the vectors above, cultivating the host cell and recovering and purifying the antibody or antigen-binding fragment thereof.

Further embodiments encompass a method for producing an antibody or antigen-binding fragment thereof above comprising obtaining a mammalian host cell comprising one or more of the vectors above, and cultivating the host cell. In one embodiment, the method further comprises recovering and purifying the antibody or antigen-binding fragment thereof.

In one embodiment, the present invention further provides an antibody or antigen-binding fragment thereof above for use in medicine. In one embodiment, the use is the treatment of an inflammatory disease, of an autoimmune disease, of a respiratory disease, of a metabolic disorder or of cancer. In one embodiment, the use is for the treatment of psoriasis, inflammatory bowel disease (Crohn's disease, ulcerative colitis), psoriatic arthritis, multiple sclerosis, rheumatoid arthritis, or ankylosing spondylitis. In one embodiment, the use is for the treatment of psoriasis. In one embodiment, the use is for the treatment of inflammatory bowel disease.

In one embodiment, the present invention further provides a pharmaceutical composition comprising an antibody molecule or antigen-binding fragment above and a pharmaceutically acceptable carrier.

In one embodiment, the present invention further provides a method for treating an inflammatory disease, an autoimmune disease, a respiratory disease, a metabolic disorder or cancer comprising administering to a subject in need thereof, for example a patient, an effective amount of an anti-IL-23p19 antibody or antigen-binding fragment thereof above, or a pharmaceutical composition comprising the antibody or antigen-binding fragment thereof. In one embodiment, the antibody or antigen-binding fragment is administered by a parenteral route of administration, or is administered intravenously or subcutaneously. In one embodiment, the antibody or antigen-binding fragment is administered subcutaneously. In one embodiment, the disease is psoriasis, inflammatory bowel disease (Crohn's disease, ulcerative colitis), psoriatic arthritis, multiple sclerosis, rheumatoid arthritis, or ankylosing spondylitis. In one embodiment, the disease is psoriasis. In one embodiment, the disease is inflammatory bowel disease.

In one embodiment, the present invention further provides a method for inhibiting the binding of IL-23 to the IL-23 receptor on a mammalian cell, comprising administering to the cell an antibody molecule or antigen-binding fragment above, whereby signaling mediated by the IL-23 receptor is inhibited.

In one embodiment, the present invention further provides a method for treating a subject having an IL-23-associated disorder, comprising administering to the subject an antibody or antigen-binding fragment above, which antibody or antigen-binding fragment binds to human IL-23.

In one embodiment, the present invention further provides a method for detecting and/or quantifying IL-23 levels in a biological sample by contacting the sample with an antibody or antigen binding fragment above and detecting binding of the antibody or fragment thereof with IL-23p19. This information can be used to diagnose an IL-23-associated disorder. Thus, methods are provided for diagnosing an IL-23-associated disorder or for determining if a subject has an increased risk of developing an IL-23-associated disorder, wherein the method comprises contacting a biological sample from a subject with an antibody or antigen binding fragment above and detecting binding of the antibody or antigen binding fragment to IL-23p19 to determine the expression or concentration of IL-23.

In one embodiment, the present invention further provides a method for inhibiting the binding of IL-23 to the IL-23 receptor on a cell, comprising administering to the cell or cellular environment an antibody or antigen-binding fragment above, whereby signaling mediated by the IL-23 receptor is inhibited.

BRIEF DESCRIPTION OF THE FIGURES

FIG. 1a: Alignment of mouse and humanized variable regions; Anti-IL-23p19 6B8 Engineered Vk regions. FIG. 1b: Alignment of mouse and humanized variable regions; Anti-IL-23p19 6B8 Engineered VH regions.

Figure 2:
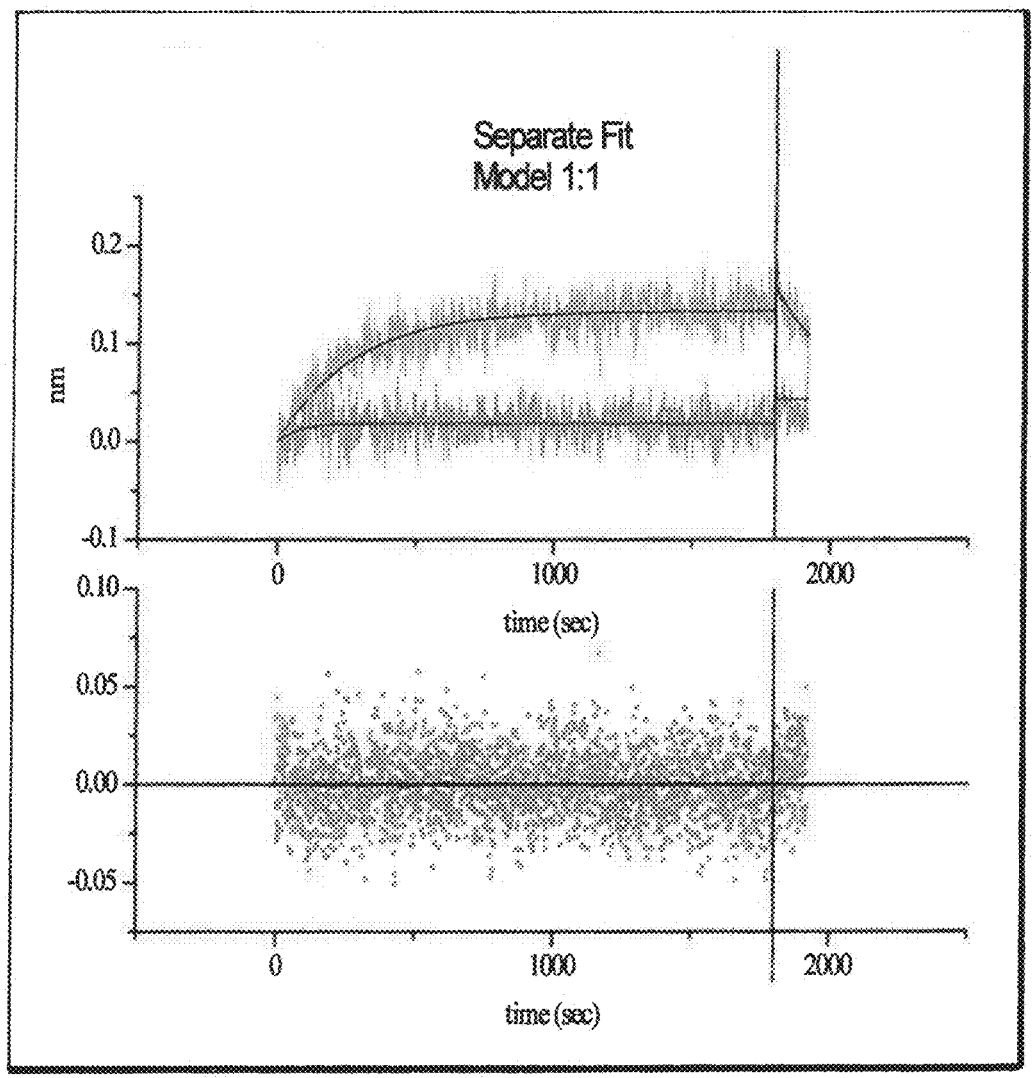

The numbering of the amino acids is by the standard Kabat numbering scheme. Regular font=Human; italic/underlined font=Murine; boxed font=Synthetic; bold/italic/underlined=CDR.

FIG. 2: Competition binding assay of human of IL-23 binding to IL-23R/Fc.

DETAILED DESCRIPTION

The p19 subunit of IL-23 (also referred to herein as "IL-23p19" and "p19 subunit") is a 189 amino acid polypeptide containing a 21 aa leader sequence (Oppmann et al. Immunity 13:715 (2000), SEQ ID NO: 181). The biological activity of the molecule is only detected when it is partnered with the IL-12p40 subunit to form IL-23. IL-23 is predominantly expressed by activated dendritic cells (DCs) and phagocytic cells. The receptor for IL-23 was found to be composed of the IL-12Rβ1 subunit of IL-12 receptor partnered with a unique subunit called IL-23R (Parham et al. J. Immunol. 168:5699 (2002)). Expression of the receptor is detected primarily on memory T cells and NK cells. Thus, expression of this cytokine:receptor pair appears to be restricted to specific populations of immune cells. While it was first thought that IL-12 and IL-23 would share many functions, the data has shown the picture to be different. Whereas IL-12 has a predominant role in the production of Th1 cells, IL-23 was found to be critically involved in the production and maintenance of a recently recognized Th cell subset termed Th17 (Kikly et al. Curr. Opin. Immunol. 18:670 (2006), Kastelein et al. Ann. Rev. Immunol. 25:221 (2007)). These cells produce IL-17A, IL-17F, IL-22 and other pro-inflammatory cytokines such as IL-6 and TNF-α. As described below, animal model studies on the role of these Th17 cells show their importance as a driving force in chronic inflammation and autoimmunity.

The present invention provides antibodies that bind to the p19 subunit of the IL-23, in particular human IL-23p19. The present invention also relates to humanized antibodies that recognize the p19 subunit of IL-23. In specific embodiments, the sequence of these humanized antibodies has been identified based on the sequences of certain lead mouse antibodies.

The lead mouse antibodies of the present invention were derived from mouse hybridomas. The immunization of the mice is carried out using different techniques. For example, antibodies that are specific for human IL-23p19 proteins or fragments thereof can be raised against an immunogenic antigen such as an isolated IL-23p19 protein, an isolated IL-23 protein, an isolated hybrid IL-23 protein, and/or a portion thereof of any of the above (including synthetic peptides). For example, a hybrid IL-23 protein comprising a mouse IL-23p40 subunit and a human IL-23p19 subunit is used to immunize mice. Preparation of immunogenic antigens and monoclonal antibody production can be performed using any suitable technique known in the art.

The lead mouse antibodies were selected based on their high affinity to human IL-23. Accordingly, in one aspect, the present invention provides an antibody that binds to human IL-23 with high affinity. Selected mouse antibodies were humanized to result in humanized antibodies. The humanized antibodies of the present invention bind to human IL-23 with high affinity. Accordingly, in another aspect, the present invention provides a humanized antibody that binds to human IL-23 with high affinity.

Accordingly, in one embodiment, the present invention provides an anti-IL-23p19 antibody having a $K_D$ of less than 40 pM. In a further embodiment, the present invention provides an anti-IL-23p19 antibody having a $K_D$ of less than 20 pM. In a further embodiment, the present invention provides an anti-IL-23p19 antibody having a $K_D$ less than 10 pM. In a further embodiment, the present invention provides an anti-IL-23p19 antibody having a $K_D$ less than 1 pM.

In another aspect, an antibody of the present invention binds to IL-23p19 with high affinity in the absence of human serum or in the presence of 50% human serum.

In a further aspect, a humanized antibody of the present invention also binds to cynomolgus monkey IL-23 with high affinity.

In another aspect, an antibody of the present invention binds to IL-23, but does not bind to IL-12. In a further aspect, an antibody of the present invention does not interfere with the biological activity of IL-12, which is a closely related family member to IL-23.

In another aspect, an antibody of the present invention inhibits the IL-23 stimulated production of IL-17 from mouse splenocytes.

In a further aspect, a humanized antibody of the present invention inhibits IL-23-induced STAT3 phosphorylation in DB cells.

In a further aspect, a humanized antibody of the present invention antagonizes the action of IL-23 by binding to the p19 subunit of IL-23, as measured by the inhibition of cytokines such as IL-17 and IL-22, whose production is stimulated by IL-23, and detected by the reduction in the levels of these cytokines.

In a further aspect, a humanized antibody of the present invention has a favorable pharmacokinetic profile (PK) profile, as exemplified by in vivo half life in cynomolgus monkeys.

In a further aspect, a humanized monoclonal anti-IL-23p19 antibody of the present invention has favorable biophysical properties, for example quality, stability, or solubility.

In one aspect, the anti-IL-23p19 antibody is a humanized antibody. In one aspect, the anti-IL-23p19 antibody is a monoclonal antibody. In one aspect, the anti-IL-23p19 antibody is a full length antibody. In one aspect, the anti-IL-23p19 antibody is a humanized monoclonal antibody, for example a full length humanized monoclonal antibody.

An antibody or antigen-binding fragment thereof of the present invention recognizes specific "IL-23p19 antigen epitope" or "IL-23p19 epitope". As used herein these terms refer to a molecule (e.g., a peptide) or a fragment of a molecule capable of immunoreactivity with an anti-IL-23p19 antibody and, for example, include an IL-23p19 antigenic determinant recognized by the any of the antibodies having a light chain/heavy chain sequence combination of SEQ ID NO:84/121, 86/123, 88/125, 90/127, 91/128, 93/130, 95/132, 97/134, 99/136, 101/138, 103/140, 105/142, 107/144, 109/146, 111/148, 113/150, 115/152, 117/154, 119/156, 160/166, 160/168, 158/166 or 158/168. IL-23p19 antigen epitopes can be included in proteins, protein fragments, peptides or the like. The epitopes are most commonly proteins, short oligopeptides, oligopeptide mimics (i.e., organic compounds that mimic antibody binding properties of the IL-23p19 antigen), or combinations thereof. The minimum size of a peptide or polypeptide epitope for an antibody is thought to be about four to five amino acids. Peptide or polypeptide epitopes contain for example at least seven amino acids or for example at least nine amino acids or for example between about 15 to about 20 amino acids. Since an antibody can recognize an antigenic peptide or polypeptide in its tertiary form, the amino acids comprising an epitope need not be contiguous, and in some cases, may not even be on the same peptide chain. Epitopes may be determined by various techniques known in the art, such as X-ray crystallography, Hydrogen/Deuterium Exchange Mass Spectrometry (HXMS), site-directed mutagenesis, alanine scanning mutagenesis, and peptide screening methods.

The generalized structure of antibodies or immunoglobulin is well known to those of skill in the art. These molecules are heterotetrameric glycoproteins, typically of about 150,000 daltons, composed of two identical light (L) chains and two identical heavy (H) chains and are typically referred to as full length antibodies. Each light chain is covalently linked to a heavy chain by one disulfide bond to form a heterodimer, and the heterotrameric molecule is formed through a covalent disulfide linkage between the two identical heavy chains of the heterodimers. Although the light and heavy chains are linked together by one disulfide bond, the number of disulfide linkages between the two heavy chains varies by immunoglobulin isotype. Each heavy and light chain also has regularly spaced intrachain disulfide bridges. Each heavy chain has at the amino-terminus a variable domain ($V_H$), followed by three or four constant domains ($C_{H1}$, $C_{H2}$, $C_{H3}$, and $C_{H4}$), as well as a hinge region between $C_{H1}$ and $C_{H2}$. Each light chain has two domains, an amino-terminal variable domain ($V_L$) and a carboxy-terminal constant domain ($C_L$). The $V_L$ domain associates non-covalently with the $V_H$ domain, whereas the $C_L$ domain is commonly covalently linked to the $C_{H1}$ domain via a disulfide bond. Particular amino acid residues are believed to form an interface between the light and heavy chain variable domains (Chothia et al., 1985, J. Mol. Biol. 186:651-663). Variable domains are also referred herein as variable regions.

Certain domains within the variable domains differ extensively between different antibodies i.e., are "hypervariable." These hypervariable domains contain residues that are directly involved in the binding and specificity of each particular antibody for its specific antigenic determinant. Hypervariability, both in the light chain and the heavy chain variable domains, is concentrated in three segments known as complementarity determining regions (CDRs) or hypervariable loops (HVLs). CDRs are defined by sequence comparison in Kabat et al., 1991, In: Sequences of Proteins of Immunological Interest, 5$^{th}$ Ed. Public Health Service, National Institutes of Health, Bethesda, Md., whereas HVLs (also referred herein as CDRs) are structurally defined according to the three-dimensional structure of the variable domain, as described by Chothia and Lesk, 1987, J. Mol. Biol. 196: 901-917. These two methods result in slightly different identifications of a CDR. As defined by Kabat, CDR-L1 is positioned at about residues 24-34, CDR-L2, at about residues 50-56, and CDR-L3, at about residues 89-97 in the light chain variable domain; CDR-H1 is positioned at about residues 31-35, CDR-H2 at about residues 50-65, and CDR-H3 at about residues 95-102 in the heavy chain variable domain. The exact residue numbers that encompass a particular CDR will vary depending on the sequence and size of the CDR. Those skilled in the art can routinely determine which residues comprise a particular CDR given the variable region amino acid sequence of the antibody. The CDR1, CDR2, CDR3 of the heavy and light chains therefore define the unique and functional properties specific for a given antibody.

The three CDRs within each of the heavy and light chains are separated by framework regions (FR), which contain sequences that tend to be less variable. From the amino terminus to the carboxy terminus of the heavy and light chain variable domains, the FRs and CDRs are arranged in the order: FR1, CDR1, FR2, CDR2, FR3, CDR3, and FR4. The largely β-sheet configuration of the FRs brings the CDRs within each of the chains into close proximity to each other as well as to the CDRs from the other chain. The resulting conformation contributes to the antigen binding site (see Kabat et al., 1991, NIH Publ. No. 91-3242, Vol. I, pages 647-669), although not all CDR residues are necessarily directly involved in antigen binding.

FR residues and Ig constant domains are not directly involved in antigen binding, but contribute to antigen binding and/or mediate antibody effector function. Some FR residues are thought to have a significant effect on antigen binding in at least three ways: by noncovalently binding directly to an epitope, by interacting with one or more CDR residues, and by affecting the interface between the heavy and light chains. The constant domains are not directly involved in antigen binding but mediate various Ig effector functions, such as participation of the antibody in antibody dependent cellular cytotoxicity (ADCC), complement dependent cytotoxicity (CDC) and antibody dependent cellular phagocytosis (ADCP).

The light chains of vertebrate immunoglobulins are assigned to one of two clearly distinct classes, kappa (κ) and lambda (λ), based on the amino acid sequence of the constant domain. By comparison, the heavy chains of mammalian immunoglobulins are assigned to one of five major classes, according to the sequence of the constant domains: IgA, IgD, IgE, IgG, and IgM. IgG and IgA are further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively. The subunit structures and three-dimensional configurations of the classes of native immunoglobulins are well known.

The terms, "antibody", "anti-IL-23p19 antibody", "humanized anti-IL-23p19 antibody", "humanized anti-IL-23p19 epitope antibody", and "variant humanized anti-IL-23p19 epitope antibody" specifically encompass monoclonal antibodies (including full length monoclonal antibodies), polyclonal antibodies, multispecific antibodies (e.g., bispecific antibodies), and antibody fragments such as variable domains and other portions of antibodies that exhibit a desired biological activity, e.g., IL-23p19 binding. The term "monoclonal antibody" (mAb) refers to an antibody that is highly specific, being directed against a single antigenic determinant, an "epitope". Therefore, the modifier "monoclonal" is indicative of antibodies directed to the identical epitope and is not to be construed as requiring production of the antibody by any particular method. It should be understood that monoclonal antibodies can be made by any technique or methodology known in the art; including e.g., the hybridoma method (Kohler et al., 1975, Nature 256: 495), or recombinant DNA methods known in the art (see, e.g., U.S. Pat. No. 4,816,567), or methods of isolation of monoclonal recombinantly produced using phage antibody libraries, using techniques described in Clackson et al., 1991, Nature 352: 624-628, and Marks et al., 1991, J. Mol. Biol. 222: 581-597.

The term "monomer" refers to a homogenous form of an antibody. For example, for a full-length antibody, monomer means a monomeric antibody having two identical heavy chains and two identical light chains.

Chimeric antibodies consist of the heavy and light chain variable regions of an antibody from one species (e.g., a non-human mammal such as a mouse) and the heavy and light chain constant regions of another species (e.g., human) antibody and can be obtained by linking the DNA sequences encoding the variable regions of the antibody from the first species (e.g., mouse) to the DNA sequences for the constant regions of the antibody from the second (e.g. human) species and transforming a host with an expression vector containing the linked sequences to allow it to produce a chimeric antibody. Alternatively, the chimeric antibody also could be one in which one or more regions or domains of the heavy and/or light chain is identical with, homologous to, or a variant of the corresponding sequence in a monoclonal antibody from another immunoglobulin class or isotype, or from a consensus or germline sequence. Chimeric antibodies can include fragments of such antibodies, provided that the antibody fragment exhibits the desired biological activity of its parent antibody, for example binding to the same epitope (see, e.g., U.S. Pat. No. 4,816,567; and Morrison et al., 1984, Proc. Natl. Acad. Sci. USA 81: 6851-6855).

The terms, "antibody fragment", "anti-IL-23p19 antibody fragment", "anti-IL-23p19 epitope antibody fragment", "humanized anti-IL-23p19 antibody fragment", "humanized anti-IL-23p19 epitope antibody fragment", "variant humanized anti-IL-23p19 epitope antibody fragment" refer to a portion of a full length anti-IL-23p19 antibody, in which a variable region or a functional capability is retained, for example, specific IL-23p19 epitope binding. Examples of antibody fragments include, but are not limited to, a Fab, Fab', F(ab')$_2$, Fd, Fv, scFv and scFv-Fc fragment, a diabody, a linear antibody, a single-chain antibody, a minibody, a diabody formed from antibody fragments, and multispecific antibodies formed from antibody fragments.

Full length antibodies can be treated with enzymes such as papain or pepsin to generate useful antibody fragments. Papain digestion is used to produces two identical antigen-binding antibody fragments called "Fab" fragments, each with a single antigen-binding site, and a residual "Fc" fragment. The Fab fragment also contains the constant domain of the light chain and the $C_{H1}$ domain of the heavy chain. Pepsin treatment yields a F(ab')$_2$ fragment that has two antigen-binding sites and is still capable of cross-linking antigen.

Fab' fragments differ from Fab fragments by the presence of additional residues including one or more cysteines from the antibody hinge region at the C-terminus of the $C_{H1}$ domain. F(ab')$_2$ antibody fragments are pairs of Fab' fragments linked by cysteine residues in the hinge region. Other chemical couplings of antibody fragments are also known.

"Fv" fragment contains a complete antigen-recognition and binding site consisting of a dimer of one heavy and one light chain variable domain in tight, non-covalent association. In this configuration, the three CDRs of each variable domain interact to define an antigen-biding site on the surface of the $V_H$-$V_L$ dimer. Collectively, the six CDRs confer antigen-binding specificity to the antibody.

A "single-chain Fv" or "scFv" antibody fragment is a single chain Fv variant comprising the $V_H$ and $V_L$ domains of an antibody where the domains are present in a single polypeptide chain. The single chain Fv is capable of recognizing and binding antigen. The scFv polypeptide may optionally also contain a polypeptide linker positioned between the $V_H$ and $V_L$ domains in order to facilitate formation of a desired three-dimensional structure for antigen binding by the scFv (see, e.g., Pluckthun, 1994, In The Pharmacology of monoclonal Antibodies, Vol. 113, Rosenburg and Moore eds., Springer-Verlag, New York, pp. 269-315).

A "diabody" refers to small antibody fragments with two antigen-binding sites, which fragments comprise a heavy chain variable domain (V.sub.H) connected to a light chain variable domain (V.sub.L) in the same polypeptide chain (V.sub.H-V.sub.L or V.sub.L-V.sub.H). Diabodies are described more fully in, e.g., Holliger et al. (1993) Proc. Natl. Acad. Sci. USA 90: 6444-6448.

Other recognized antibody fragments include those that comprise a pair of tandem Fd segments ($V_H$—$C_{H1}$-$V_H$-$C_{H1}$) to form a pair of antigen binding regions. These "linear antibodies" can be bispecific or monospecific as described in, for example, Zapata et al. 1995, Protein Eng. 8(10):1057-1062.

A "humanized antibody" or a "humanized antibody fragment" is a specific type of chimeric antibody which includes an immunoglobulin amino acid sequence variant, or fragment thereof, which is capable of binding to a predetermined antigen and which, comprises one or more FRs having substantially the amino acid sequence of a human immunoglobulin and one or more CDRs having substantially the amino acid sequence of a non-human immunoglobulin. This non-human amino acid sequence often referred to as an "import" sequence is typically taken from an "import" antibody domain, particularly a variable domain. In general, a humanized antibody includes at least the CDRs or HVLs of a non-human antibody, inserted between the FRs of a human heavy or light chain variable domain. The present invention describes specific humanized anti-IL-23p19 antibodies which contain CDRs derived from the mouse monoclonal antibodies or humanized CDRs shown in Tables 3 and 4 inserted between the FRs of human germline sequence heavy and light chain variable domains. It will be understood that certain mouse FR residues may be important to the function of the humanized antibodies and therefore certain of the human germline sequence heavy and light chain variable domains residues are modified to be the same as those of the corresponding mouse sequence.

In another aspect, a humanized anti-IL-23p19 antibody comprises substantially all of at least one, and typically two, variable domains (such as contained, for example, in Fab, Fab', F(ab')2, Fabc, and Fv fragments) in which all, or substantially all, of the CDRs correspond to those of a non-human immunoglobulin, and specifically herein, all of the CDRs are mouse or humanized sequences as detailed in Tables 1 through 4 herein below and all, or substantially all, of the FRs are those of a human immunoglobulin consensus or germline sequence. In another aspect, a humanized anti-IL-23p19 antibody also includes at least a portion of an immunoglobulin Fc region, typically that of a human immunoglobulin. Ordinarily, the antibody will contain both the light chain as well as at least the variable domain of a heavy chain. The antibody also may include one or more of the $C_{H1}$, hinge, $C_{H2}$, $C_{H3}$, and/or $C_{H4}$ regions of the heavy chain, as appropriate.

A humanized anti-IL-23p19 antibody can be selected from any class of immunoglobulins, including IgM, IgG, IgD, IgA and IgE, and any isotype, including $IgG_1$, $IgG_2$, $IgG_3$, $IgG_4$, $IgA_1$ and $IgA_2$. For example, the constant domain can be a complement fixing constant domain where it is desired that the humanized antibody exhibit cytotoxic activity, and the isotype is typically $IgG_1$. Where such cytotoxic activity is not desirable, the constant domain may be of another isotype, e.g., $IgG_2$. An alternative humanized anti-IL-23p19 antibody can comprise sequences from more than one immunoglobulin class or isotype, and selecting particular constant domains to optimize desired effector functions is within the ordinary skill in the art. In specific embodiments, the present invention provides antibodies that are IgG1 antibodies and more particularly, are IgG1 antibodies in which there is a knock-out of effector functions.

The FRs and CDRs, or HVLs, of a humanized anti-IL-23p19 antibody need not correspond precisely to the parental sequences. For example, one or more residues in the import CDR, or HVL, or the consensus or germline FR sequence may be altered (e.g., mutagenized) by substitution, insertion or deletion such that the resulting amino acid residue is no longer identical to the original residue in the corresponding position in either parental sequence but the antibody nevertheless retains the function of binding to IL-23p19. Such alteration typically will not be extensive and will be conservative alterations. Usually, at least 75% of the humanized antibody residues will correspond to those of the parental consensus or germline FR and import CDR sequences, more often at least 90%, and most frequently greater than 95%, or greater than 98% or greater than 99%.

Immunoglobulin residues that affect the interface between heavy and light chain variable regions ("the $V_L$-$V_H$ interface") are those that affect the proximity or orientation of the two chains with respect to one another. Certain residues that may be involved in interchain interactions include $V_L$ residues 34, 36, 38, 44, 46, 87, 89, 91, 96, and 98 and $V_H$ residues 35, 37, 39, 45, 47, 91, 93, 95, 100, and 103 (utilizing the numbering system set forth in Kabat et al., Sequences of Proteins of Immunological Interest (National Institutes of Health, Bethesda, Md., 1987)). U.S. Pat. No. 6,407,213 also discusses that residues such as $V_L$ residues 43 and 85, and $V_H$ residues 43 and 60 also may be involved in this interaction. While these residues are indicated for human IgG only, they are applicable across species. Important antibody residues that are reasonably expected to be involved in interchain interactions are selected for substitution into the consensus sequence.

The terms "consensus sequence" and "consensus antibody" refer to an amino acid sequence which comprises the most frequently occurring amino acid residue at each location in all immunoglobulins of any particular class, isotype, or subunit structure, e.g., a human immunoglobulin variable domain. The consensus sequence may be based on immunoglobulins of a particular species or of many species. A "consensus" sequence, structure, or antibody is understood to encompass a consensus human sequence as described in certain embodiments, and to refer to an amino acid sequence which comprises the most frequently occurring amino acid residues at each location in all human immunoglobulins of any particular class, isotype, or subunit structure. Thus, the consensus sequence contains an amino acid sequence having at each position an amino acid that is present in one or more known immunoglobulins, but which may not exactly duplicate the entire amino acid sequence of any single immunoglobulin. The variable region consensus sequence is not obtained from any naturally produced antibody or immunoglobulin. Kabat et al., 1991, Sequences of Proteins of Immunological Interest, 5th Ed. Public Health Service, National Institutes of Health, Bethesda, Md., and variants thereof. The FRs of heavy and light chain consensus sequences, and variants thereof, provide useful sequences for the preparation of humanized anti-IL-23p19 antibodies. See, for example, U.S. Pat. Nos. 6,037,454 and 6,054,297.

Human germline sequences are found naturally in the human population. A combination of those germline genes generates antibody diversity. Germline antibody sequences for the light chain of the antibody come from conserved human germline kappa or lambda v-genes and j-genes. Similarly the heavy chain sequences come from germline v-, d- and j-genes (LeFranc, M-P, and LeFranc, G, "The Immunoglobulin Facts Book" Academic Press, 2001).

As used herein, "variant", "anti-IL-23p19 variant", "humanized anti-IL-23p19 variant", or "variant humanized anti-IL-23p19" each refers to a humanized anti-IL-23p19 antibody having at least a light chain variable murine CDR from any of the sequences as shown in Table 1 or a heavy chain murine CDR sequence derived from the murine monoclonal antibody as shown in Table 2. Variants include those having one or more amino acid changes in one or both light chain or heavy chain variable domains, provided that the amino acid change does not substantially impair binding of the antibody to IL-23p19. Exemplary humanized antibodies produced herein include those designated as Antibody A, Antibody B, Antibody C and Antibody D, and the various light chains and heavy chains of the same are shown in SEQ ID Nos:174 and 180, and SEQ ID Nos:176 and 178, respectively.

An "isolated" antibody is one that has been identified and separated and/or recovered from a component of its natural environment. Contaminant components of the antibody's natural environment are those materials that may interfere with diagnostic or therapeutic uses of the antibody, and can be enzymes, hormones, or other proteinaceous or nonproteinaceous solutes. In one aspect, the antibody will be purified to at least greater than 95% isolation by weight of antibody.

An isolated antibody includes an antibody in situ within recombinant cells in which it is produced, since at least one component of the antibody's natural environment will not be present. Ordinarily however, an isolated antibody will be prepared by at least one purification step in which the recombinant cellular material is removed.

The term "antibody performance" refers to factors that contribute to antibody recognition of antigen or the effectiveness of an antibody in vivo. Changes in the amino acid sequence of an antibody can affect antibody properties such as folding, and can influence physical factors such as initial rate of antibody binding to antigen ($k_a$), dissociation constant of the antibody from antigen ($k_d$), affinity constant of the antibody for the antigen (Kd), conformation of the antibody, protein stability, and half life of the antibody.

The term "epitope tagged" when used herein, refers to an anti-IL-23p19 antibody fused to an "epitope tag". An "epitope tag" is a polypeptide having a sufficient number of amino acids to provide an epitope for antibody production, yet is designed such that it does not interfere with the desired activity of the humanized anti-IL-23p19 antibody. The epitope tag is usually sufficiently unique such that an antibody raised against the epitope tag does not substantially cross-react with other epitopes. Suitable tag polypeptides generally contain at least 6 amino acid residues and usually contain about 8 to 50 amino acid residues, or about 9 to 30 residues. Examples of epitope tags and the antibody that binds the epitope include the flu HA tag polypeptide and its antibody 12CA5 (Field et al., 1988 Mol. Cell. Biol. 8: 2159-2165; c-myc tag and 8F9, 3C7, 6E10, G4, B7 and 9E10 antibodies thereto (Evan et al., 1985, Mol. Cell. Biol. 5(12):3610-3616; and Herpes simplex virus glycoprotein D (gD) tag and its antibody (Paborsky et al. 1990, Protein Engineering 3(6): 547-553). In certain embodiments, the epitope tag is a "salvage receptor binding epitope". As used herein, the term "salvage receptor binding epitope" refers to an epitope of the Fc region of an IgG molecule (such as $IgG_1$, $IgG_2$, $IgG_3$, or $IgG_4$) that is responsible for increasing the in vivo serum half-life of the IgG molecule.

In some embodiments, the antibodies of the present invention may be conjugated to a cytotoxic agent. This is any substance that inhibits or prevents the function of cells and/or causes destruction of cells. The term is intended to include radioactive isotopes (such as $I^{131}$, $I^{125}$, $Y^{90}$, and $Re^{186}$), chemotherapeutic agents, and toxins such as enzymatically active toxins of bacterial, fungal, plant, or animal origin, and fragments thereof. Such cytotoxic agents can be coupled to the humanized antibodies of the present invention using standard procedures, and used, for example, to treat a patient indicated for therapy with the antibody.

A "chemotherapeutic agent" is a chemical compound useful in the treatment of cancer. There are numerous examples of chemotherapeutic agents that could be conjugated with the therapeutic antibodies of the present invention. Examples of such chemotherapeutic agents include alkylating agents such a thiotepa and cyclosphosphamide; alkyl sulfonates such as busulfan, improsulfan, and piposulfan; aziridines such as benzodopa, carboquone, meturedopa, and uredopa; ethylenimines and methylamelamines including altretamine, triethylenemelamine, trietylenephosphoramide, triethylenethiophosphoramide, and trimethylolomelamine; acetogenins (especially bullatacin and bullatacinone); camptothecin (including the synthetic analogue topotecan); bryostatin; callystatin; CC-1065 (including its adozelesin, carzelesin, and bizelesin synthetic analogues); cryptophycines (particularly cryptophycin 1 and cryptophycin 8); dolastatin, auristatins, (including analogues monomethyl-auristatin E and monomethyl-auristatin F); duocarmycin (including the synthetic analogues, KW-2189 and CBI-TMI); eleutherobin; pancratistatin; sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine; trofosfamide, uracil mustard; nitrosureas such as carmustine, chlorozotocin, fotemustine, lomustine, nimustine, ranimustine; antibiotics such as the enediyne antibiotics (e.g., calicheamicin, especially calichemicin gamma1I and calicheamicin phill, see for example, Agnew, Chem. Intl. Ed. Engl., 33:183-186; dynemicin, including dynemicin A; bisphosphonates, such as clodronate; esperamicin; as well as neocarzinostatin chromophore and related chromoprotein enediyne antibiotic chromomophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (Adriamycin™) (including morpholino-doxorubicin, cyanomorpholino-doxorubicin, 2-pyrrolino-doxorubicin, and deoxydoxorubicin), epirubicin, esorubicin, idarubicin, marcellomycin, mitomycins such as mitomycin C, mycophenolic acid, nogalamycin, olivomycins, peplomycin, potfiromycin, puromycine, quelamycin, rodorubicin, streptonigrin, streptozocin, tubercidin, ubenimex, zinostatin, zorubicin; anti-metabolites such a methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adranals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; democolcine; diaziquone; elfomithine; elliptinium acetate; an epothilone; etoglucid; gallium nitrate; hydroxyurea; lentinan; lonidamine; maytansinoids such as maytansine and ansamitocins; mitoguazone, mitoxantrone; mopidamol; nitracrine; pentostatin; phenamet; pirarubicin; losoxantrone; podophyllinic acid; 2-ethylhydrazide; procarbazine; PSK®; razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitabronitol; mitolactol; pipobroman; gacytosine; arabinoside ("Ara-C"); cyclophosphamide; thiotepa; taxoids, e.g., paclitaxel (TAXOL®, Bristol-Myers Squibb Oncology, Princeton, N.J.) and doxetaxel (TAXOTERE®, Rhone-Poulenc Rorer, Antony, France); chlorambucil; gemcitabine (Gemzar™); 6-thioguanine; mercaptopurine; methotrexate; platinum analogs such as cisplatin and carboplatin; vinblastine; platinum; etoposide (VP-16); ifosfamide; mitoxantrone; vincristine; vinorelbine Navelbine™); novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids, or derivatives of any of the above. Also included in this definition are anti-hormonal agents that act to regulate or inhibit hormone action on tumors such as anti-estrogens and selective estrogen receptor modulators (SERMs), including, for example, tamoxifen (including Nolvadex™), raloxifene, droloxifene, 4-hydroxytamoxifen, trioxifene, keoxifene, LY117018, onapristone, and toremifene (Fareston™); aromatase inhibitors that inhibit the enzyme aromatase, which regulates estrogen production in the adrenal glands, such as, for example, 4(5)-imidazoles, aminoglutethimide, megestrol acetate (Megace™), exemestane, formestane, fadrozole, vorozole (Rivisor™), letrozole (Femara™), and anastrozole (Arimidex™); and anti-androgens such as flutamide, nilutamide, bicalutamide, leuprolide, and goserelin; and pharmaceutically acceptable salts, acids, or derivatives of any of the above. Any one or more of these agents may be conjugated to the humanized antibodies of the present invention to provide a useful therapeutic agent for the treatment of various disorders.

The antibodies also may be conjugated to prodrugs. A "prodrug" is a precursor or derivative form of a pharmaceutically active substance that is less cytotoxic to tumor cells compared to the parent drug and is capable of being enzymatically activated or converted into the more active form. See, for example, Wilman, 1986, "Prodrugs in Cancer Chemotherapy", In Biochemical Society Transactions, 14, pp. 375-382, 615th Meeting Belfast and Stella et al., 1985, "Prodrugs: A Chemical Approach to Targeted Drug Delivery, In: "Directed Drug Delivery, Borchardt et al., (ed.), pp. 247-267, Humana Press. Useful prodrugs include, but are not limited to, phosphate-containing prodrugs, thiophosphate-containing prodrugs, sulfate-containing prodrugs peptide-containing prodrugs, D-amino acid-modified prodrugs, glycosylated prodrugs, β-lactam-containing prodrugs, optionally substituted phenoxyacetamide-containing prodrugs, and optionally substituted phenylacetamide-containing prodrugs, 5-fluorocytosine and other 5-fluorouridine prodrugs that can be converted into the more active cytotoxic free drug. Examples of cytotoxic drugs that can be derivatized into a prodrug form include, but are not limited to, those chemotherapeutic agents described above.

For diagnostic as well as therapeutic monitoring purposes, the antibodies of the invention also may be conjugated to a label, either a label alone or a label and an additional second agent (prodrug, chemotherapeutic agent and the like). A label, as distinguished from the other second agents refers to an agent that is a detectable compound or composition and it may be conjugated directly or indirectly to a humanized antibody of the present invention. The label may itself be detectable (e.g., radioisotope labels or fluorescent labels) or, in the case of an enzymatic label, may catalyze chemical alteration of a substrate compound or composition that is detectable. Labeled humanized anti-IL-23p19 antibody can be prepared and used in various applications including in vitro and in vivo diagnostics.

The antibodies of the present invention may be formulated as part of a liposomal preparation in order to affect delivery thereof in vivo. A "liposome" is a small vesicle composed of various types of lipids, phospholipids, and/or surfactant. Liposomes are useful for delivery to a mammal of a compound or formulation, such as a humanized anti-IL-23p19 antibody disclosed herein, optionally, coupled to or in combination with one or more pharmaceutically active agents and/or labels. The components of the liposome are commonly arranged in a bilayer formation, similar to the lipid arrangement of biological membranes.

Certain aspects of the present invention related to isolated nucleic acids that encode one or more domains of the humanized antibodies of the present invention. An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is distinguished from the nucleic acid molecule as it exists in natural cells.

In various aspects of the present invention one or more domains of the humanized antibodies will be recombinantly expressed. Such recombinant expression may employ one or more control sequences, i.e., polynucleotide sequences necessary for expression of an operably linked coding sequence in a particular host organism. The control sequences suitable for use in prokaryotic cells include, for example, promoter, operator, and ribosome binding site sequences. Eukaryotic control sequences include, but are not limited to, promoters, polyadenylation signals, and enhancers. These control sequences can be utilized for expression and production of humanized anti-IL-23p19 antibody in prokaryotic and eukaryotic host cells.

A nucleic acid sequence is "operably linked" when it is placed into a functional relationship with another nucleic acid sequence. For example, a nucleic acid presequence or secretory leader is operably linked to a nucleic acid encoding a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers are optionally contiguous. Linking can be accomplished by ligation at convenient restriction sites. If such sites do not exist, synthetic oligonucleotide adaptors or linkers can be used.

As used herein, the expressions "cell", "cell line", and "cell culture" are used interchangeably and all such designations include the progeny thereof. Thus, "transformants" and "transformed cells" include the primary subject cell and cultures derived therefrom without regard for the number of transfers.

The term "mammal" for purposes of treatment refers to any animal classified as a mammal, including humans, domesticated and farm animals, and zoo, sports, or pet animals, such as dogs, horses, cats, cows, and the like. Preferably, the mammal is human.

A "disorder", as used herein, is any condition that would benefit from treatment with a humanized anti-IL-23p19 antibody described herein. This includes chronic and acute disorders or diseases including those pathological conditions that predispose the mammal to the disorder in question. Non-limiting examples or disorders to be treated herein include inflammatory, angiogenic, autoimmune and immunologic disorders, respiratory disorders, cancer, hematological malignancies, benign and malignant tumors, leukemias and lymphoid malignancies.

The terms "cancer" and "cancerous" refer to or describe the physiological condition in mammals that is typically characterized by unregulated cell growth. Examples of cancer include, but are not limited to, carcinoma, lymphoma, blastoma, sarcoma, and leukemia.

As used herein, the term "IL-23-associated disorder" or "IL-23-associated disease" refers to a condition in which IL-23 activity contributes to the disease and typically where IL-23 is abnormally expressed. An IL-23-associated disorder includes diseases and disorders of the immune system, such as autoimmune disorders and inflammatory disorders. Such conditions include, but are not limited to, rheumatoid arthritis (RA), systemic lupus erythematosus (SLE), scleroderma, Sjogren's syndrome, multiple sclerosis, psoriasis, psoriatic arthritis, inflammatory bowel disease (e.g., ulcerative colitis and Crohn's disease), pulmonary inflammation, asthma, idiopathic thrombocytopenic purara (ITP) and ankylosing spondylitis.

The term "intravenous infusion" refers to introduction of an agent into the vein of an animal or human patient over a period of time greater than approximately 15 minutes, generally between approximately 30 to 90 minutes.

The term "intravenous bolus" or "intravenous push" refers to drug administration into a vein of an animal or human such that the body receives the drug in approximately 15 minutes or less, generally 5 minutes or less.

The term "subcutaneous administration" refers to introduction of an agent under the skin of an animal or human patient, preferable within a pocket between the skin and underlying tissue, by relatively slow, sustained delivery from a drug receptacle. Pinching or drawing the skin up and away from underlying tissue may create the pocket.

The term "subcutaneous infusion" refers to introduction of a drug under the skin of an animal or human patient, preferably within a pocket between the skin and underlying tissue, by relatively slow, sustained delivery from a drug receptacle for a period of time including, but not limited to, 30 minutes or less, or 90 minutes or less. Optionally, the infusion may be made by subcutaneous implantation of a drug delivery pump implanted under the skin of the animal or human patient, wherein the pump delivers a predetermined amount of drug for a predetermined period of time, such as 30 minutes, 90 minutes, or a time period spanning the length of the treatment regimen.

The term "subcutaneous bolus" refers to drug administration beneath the skin of an animal or human patient, where bolus drug delivery is less than approximately 15 minutes; in another aspect, less than 5 minutes, and in still another aspect, less than 60 seconds. In yet even another aspect, administration is within a pocket between the skin and underlying tissue, where the pocket may be created by pinching or drawing the skin up and away from underlying tissue.

The term "therapeutically effective amount" is used to refer to an amount of an active agent that relieves or ameliorates one or more of the symptoms of the disorder being treated. In another aspect, the therapeutically effective amount refers to a target serum concentration that has been shown to be effective in, for example, slowing disease progression. Efficacy can be measured in conventional ways, depending on the condition to be treated.

The terms "treatment" and "therapy" and the like, as used herein, are meant to include therapeutic as well as prophylactic, or suppressive measures for a disease or disorder leading to any clinically desirable or beneficial effect, including but not limited to alleviation or relief of one or more symptoms, regression, slowing or cessation of progression of the disease or disorder. Thus, for example, the term treatment includes the administration of an agent prior to or following the onset of a symptom of a disease or disorder thereby preventing or removing one or more signs of the disease or disorder. As another example, the term includes the administration of an agent after clinical manifestation of the disease to combat the symptoms of the disease. Further, administration of an agent after onset and after clinical symptoms have developed where administration affects clinical parameters of the disease or disorder, such as the degree of tissue injury or the amount or extent of metastasis, whether or not the treatment leads to amelioration of the disease, comprises "treatment" or "therapy" as used herein. Moreover, as long as the compositions of the invention either alone or in combination with another therapeutic agent alleviate or ameliorate at least one symptom of a disorder being treated as compared to that symptom in the absence of use of the humanized anti-IL-23p19 antibody composition, the result should be considered an effective treatment of the underlying disorder regardless of whether all the symptoms of the disorder are alleviated or not.

The term "package insert" is used to refer to instructions customarily included in commercial packages of therapeutic products, that contain information about the indications, usage, administration, contraindications and/or warnings concerning the use of such therapeutic products.

Antibodies

In one aspect, described and disclosed herein are anti-IL-23 antibodies, in particular humanized anti-IL-23p19 antibodies, and compositions and articles of manufacture comprising one or more anti-IL-23 antibody, in particular one or more humanized anti-IL-23p19 antibody of the present invention. Also described are binding agents that include an antigen-binding fragment of an anti-IL-23 antibody, in particular a humanized anti-IL-23p19 antibody. The humanized anti-IL-23p19 antibodies and binding agents can inhibit the production of Th17 associated cytokines, which contribute to chronic autoimmune and inflammatory diseases. The humanized anti-IL-23p19 antibodies and binding agents can thus be used in the treatment of a variety of diseases or disorders. A humanized anti-IL-23p19 antibody and an IL-23p19 binding agent each includes at least a portion that specifically recognizes an IL-23p19 epitope (i.e., an antigen-binding fragment).

In the initial characterization mouse antibodies were selected based on IL-23p19 binding characterization.

Accordingly in one aspect, an antibody of the present invention has a $K_D$ for IL-23, in particular human IL-23, of less than 100 pM. In another aspect, an antibody of the present invention has a $K_D$ of less than 40 pM. In another aspect, an antibody of the present invention has a $K_D$ of less than 20 pM. In another aspect, an antibody of the present invention has a $K_D$ of less than 10 pM. In another aspect, a monoclonal antibody of the present invention has a $K_D$ of less than 1 pM.

The selected mouse antibodies have the following light chain variable regions and heavy chain variable regions as shown in Table 1 and 2:

TABLE 1

| Anti-IL-23p19 Mouse Leads - VK Sequences | |
|---|---|
| 2D1vk | GACATTGTGCTGACCCAATCTCCAGGTTCTTTGGCTGTGTCTCTAGGGCAG AGGGCCACCATATCCTGCAGAACCAGTGAAAGTGTTTATAGTTATGGCCAA AATTTTATACACTGGTACCAGCAGAAACCAGGACAGCCACCCAAACTCCTC ATCTATCGTGCATCCAACCTGGAATCTGGGATCCCTGCCAGGTTCAGTGGC AGTGGGTCTAGGACAGACTTCACCCTCACCATGAATCCTGTGGAGGCTGAT GATGTTGCAACCTATTACTGTCAGCAAACTAATGAGGATCCGTACACGTTC GGAGGGGGGACCAAGCTGGAAATAAGA (SEQ ID NO: 83) DIVLTQSPGSLAVSLGQRATISCRTSESVYSYGQNFIHWYQQKPGQPPKLL IYRASNLESGIPARFSGSGSRTDFTLTMNPVEADDVATYYCQQTNEDPYTF GGGTKLEIR (SEQ ID NO: 84) |
| 6B8Vk | GACATTGTGATGACCCAGTCTCACAAATTCTTGTCCACATCAGTGGGAGAC AGGGTCACCATCACTTGCAAGGCCAGTCGGGATGTGGCTATTGCTGTAGCC TGGTATCAACAGAAACCAGGGCAATCTCCTAAACTACTTCTTTTCTGGGCA TCCACCCGACACACTGGGGTCCCTGATCGCTTCACAGGCAGTGGATCTCGG |

TABLE 1-continued

Anti-IL-23p19 Mouse Leads - VK Sequences

ACAGATTTCACTCTCACCATTAGCAATGTGCAGTCTGAAGACTTGGCAGAT
TATTTCTGTCACCAATATAGCAGCTATCCATTCACGTTCGGCTCGGGGACA
AAGTTGGAAATAAAG (SEQ ID NO: 85)
DIVMTQSHKFLSTSVGDRVTITCKASRDVAIAVAWYQQKPGQSPKLLLFWA
STRHTGVPDRFTGSGSRTDFTLTISNVQSEDLADYFCHQYSSYPFTFGSGT
KLEIK (SEQ ID NO: 86)

9D12-Vk   GACATTGCGCTGACCCAATCTCCAGCTTCTTTGGCTGTGTCTCTGGGGCAG
          AGGGCCACCATATCCTGCAGAGCCAGTGAAACTATTAATTTTTATGGCACT
          AGTTTTATGCACTGGTACCAGCAGAAACCAGGACAGTCACCCAAACTCCTC
          ATCTATCGTGCATCCAACCTAGAATCTGGGATCCCTGCCAGGTTCAGTGGC
          AGTGGGTCTAGGACAGACTTCACCCTCACCATTAATCCTGTGGAGGCTGAT
          GATGTTGCAACCTATTACTGTCAGCAAACTAATGAGGATCCGTACACGTTC
          GGAGGGGGGACTAAGTTGGAAATAAAA (SEQ ID NO: 87)
          DIALTQSPASLAVSLGQRATISCRASETINFYGTSFMHWYQQKPGQSPKLL
          IYRASNLESGIPARFSGSGSRTDFTLTINPVEADDVATYYCQQTNEDPYTF
          GGGTKLEIK (SEQ ID NO: 88)

15C11vk   GATGTTGTGATGACCCAAACTCCACTCTCCCTGCCTGTCAGTCTTGGAGAT
          CAAGCCTCCATCTCTTGCAGATCTAGTCAGAGCCTTGTACACAGTAATGGA
          AACACCTATTTACATTGGTACCTGCAGAAGCCAGGCCAGTCTCCAAAGCTC
          CTGATCTACAAAGTTTCCAACCGATTTTCTGGGGTCCCAGACAGGTTCAGT
          GGCAGTGGATCAGGGACAGATTTCACACTCAAGATCAACAGAGTGGAGGCT
          GAGGATCTGGGAGTTTATTTCTGCTCTCAAAGTACACATGTTCCGTACACG
          TTCGGAGGGGGGACCCAGCTGGAAATAAAA (SEQ ID NO: 89)
          DVVMTQTPLSLPVSLGDQASISCRSSQSLVHSNGNTYLHWYLQKPGQSPKL
          LIYKVSNRFSGVPDRFSGSGSGTDFTLKINRVEAEDLGVYFCSQSTHVPYT
          FGGGTQLEIK (SEQ ID NO: 90)

15F1vk    DIVMTQSPATLSVTPGDRVSLSCRASQSISDYLHWYQQRSHESPRLLIKYA
          SQSISGIPSRFSGSGSGSDFTLTINSVEPEDVGVYYCQNGHSFPFTFGSGT
          KLEIK (SEQ ID NO: 91)

18D3vk    GACATTGTGATGACTCAGTCTCCAGCCACCCTGTCTGTGACTCCAGGAGAT
          AGAGTCTCTCTTTCCTGCAGGGCCAGTCAGAGTATTAGCGACTACTTATAC
          TGGTATCAACAAAAATCACATGAGTCTCCAAGGCTTCTCATCAAATTTGCT
          TCCCAATCCATCTCTGGGATCCCCTCCAGGTTCACTGGCAGTGGATCAGGG
          TCAGATTTCACTCTCAGTATCGACAGTGTGGAACCTGATGATGTTGGAGTC
          TTTTTCTGTCAAAATGGTCACAGCTTTCCGTTCACGTTCGGAGGGGGGACC
          AAGCTGGAAATAAAA (SEQ ID NO: 92)
          DIVMTQSPATLSVTPGDRVSLSCRASQSISDYLYWYQQKSHESPRLLIKFA
          SQSISGIPSRFTGSGSGSDFTLSIDSVEPDDVGVFFCQNGHSFPFTFGGGT
          KLEIK (SEQ ID NO: 93)

18C4vk    GACATTGTGATGACTCAGTCTCCAGCCACCCTGTCTGTGACTCCAGGAGAT
          AGAGTCTCTCTTTCCTGCAGGGCCAGCCAGAGTATTAGCGAGTACTTACAC
          TGGTATCAACAAAAATCACATGAGTCTCCAAGGCTTCTCATCAAATATGCT
          TCCCAATCCATCTCTGGGATCCCCTCCAGGTTCAGTGGCAGTGGATCAGGG
          TCAGATTTCACTCTCAGTATCAACAGTGTGGAACCTGAAGATGTTGGAGTG
          TATTACTGTCAAAATGGTCACAGCTTTTCCATTCACGTTCGGCTCGGGGACA
          AAGTTGGAAATAAAA (SEQ ID NO: 94)
          DIVMTQSPATLSVTPGDRVSLSCRASQSISEYLHWYQQKSHESPRLLIKYA
          SQSISGIPSRFSGSGSGSDFTLSINSVEPEDVGVYYCQNGHSFPFTFGSGT
          KLEIK (SEQ ID NO: 95)

18E5vk    GACATTGTGATGACTCAGTCTCCAGCCACCCTGTCTGTGACTCCAGGAGAT
          AGAGTCTCTCTTTCCTGCAGGGCCAGCCAGAGTATTAGCGACTACTTATAC
          TGGTATCAACAAAAATCACATGAGTCTCCAAGGCTTCTCATCAAATTTGCT
          TCCCAATCCATCTCTGGGATCCCCTCCAGGTTCACTGGCAGTGGATCAGGG
          TCAGATTTCACTCTCAGTATCGACAGTGTGGAACCTGATGATGTTGGAGTC
          TTTTTCTGTCAAAATGGTCACAGCTTTCCGTTCACGTTCGGAGGGGGGACC
          AAGCTGGAAATAAAA (SEQ ID NO: 96)
          DIVMTQSPATLSVTPGDRVSLSCRASQSISDYLYWYQQKSHESPRLLIKFA
          SQSISGIPSRFTGSGSGSDFTLSIDSVEPDDVGVFFCQNGHSFPFTFGGGT
          KLEIK (SEQ ID NO: 97)

20E8vk    GACATTGTGATGACTCAGTCTCCAGCCACCCTGTCTGTGACTCCAGGAGAT
          AGAGTCTCTCTTTCCTGCAGGGCCAGCCAGAGTATTAGCGAGTATTACAC
          TGGTATCAACAAAAATCACATGAGTCTCCAAGGCTTCTCATCAAATATGCT
          TCCCAATCCATCTCTGGGATCCCCTCCAGGTTCAGTGGCAGTGGATCAGGG
          TCAGATTTCACTCTCAGTATCAACAGTGTGGAACCTGAAGATGTTGGAGTT
          TATTACTGTCAAAATGGTCACAGCTTTTCCATTCACGTTCGGCTCGGGGACA
          AAGTTGGAAATAAAA (SEQ ID NO: 98)
          DIVMTQSPATLSVTPGDRVSLSCRASQSISEYLHWYQQKSHESPRLLIKYA
          SQSISGIPSRFSGSGSGSDFTLSINSVEPEDVGVYYCQNGHSFPFTFGSGT
          KLEIK (SEQ ID NO: 99)

TABLE 1-continued

Anti-IL-23p19 Mouse Leads - VK Sequences

22E2vk  GACATTGTGATGACTCAGTCTCCAGCCACCCTGTCTGTGACTCCAGGAGAT
AGAGTCTCTCTCCTGCAGGGCCAGCCAGAGTATTAGCGTCTACTTACAC
TGGTATCAACAAAAATCACCTGAGTCTCCAAGGCTTCTCATCAAATATGCT
TCCCAATCCATCTCTGGGATCCCCTCCAGGTTCAGTGGCAGTGGATCAGGG
TCAGATTTCACTCTCAGTATCAACAGTGTGGAACCTGAAGATGTTGGAGTT
TATTACTGTCAAAATGGTCACAGCTTTCCATTCACGTTCGGCTCGGGGACA
AAGTTGGAAATAAAA (SEQ ID NO: 100)
DIVMTQSPATLSVTPGDRVSLSCRASQSISVYLHWYQQKSPESPRLLIKYA
SQSISGIPSRFSGSGSGSDFTLSINSVEPEDVGVYYCQNGHSFPFTFGSGT
KLEIK (SEQ ID NO: 101)

24A54vk GACATTGTGATGACTCAGTCTCCAGCCACCCTGTCTGTGACTCCAGGAAAT
AGAGTCTCTCTTTCCTGCAGGGCCAGCCAGAGTATTAGCGACTACTTACAC
TGGTATCAACAAAAATCACATGAGTCTCCAAGGCTTCTCATCAAATATGCT
TCCCAATCCATCTCTGGGATCCCCTCCAGGTTCAGTGGCAGTGGATCAGGG
TCAAATTTCACTCTCAGTATCAACAGTGTGGAACCTGAAGATGTTGGAGTG
TATTATTGTCAAAATGGTCACAGCTTTCCATTCACGTTCGGCTCGGGGACA
AAGTTGGAAATAAAA (SEQ ID NO: 102)
DIVMTQSPATLSVTPGNRVSLSCRASQSISDYLHWYQQKSHESPRLLIKYA
SQSISGIPSRFSGSGSGSNFTLSINSVEPEDVGVYYCQNGHSFPFTFGSGT
KLEIK (SEQ ID NO: 103)

26F7Vk  GACATTGTGCTGACACAGTCTCCTGCTTCCTTAGCTGTTTCTCTGGGGCAG
AGGGCCACCATCTCATGCAGGGCCAGCAAAAGTGTCAGATTCTCTGACTAT
TTTTATATGCACTGGTACCAACAGAAACCAGGACAGCCACCCAAACTCCTC
ATCTACCTTGCATCCAACCTAGAATCTGGGGTCCCTGCCAGGTTCAGTGGC
AGTGGGTCTGGGACAGACTTCACCCTCAACATCCATCCTGTGGAGGAGGAG
GATGCTGCAACCTATTACTGTCAGAACAGTAGGGAGCTTCCGTACACGTTC
GGAGGGGGGACCAAGCTGGAGATAAAA (SEQ ID NO: 104)
DIVLTQSPASLAVSLGQRATISCRASKSVRFSDYFMHWYQQKPGQPPKLL
IYLASNLESGVPARFSGSGSGTDFTLNIHPVEEEDAATYYCQNSRELPYTF
GGGTKLEIK (SEQ ID NO: 105)

27G8vk  GACATTGTGTTGACACAGTCTCCTGCTTCCTTAGCTGTATCTCTGGGGCAG
AGGGCCACCATCTCATGCAGGGCCAGCAAAAGTGTCAGTACATCTGGCTAT
AGTTATATACACTGGTACCAACAGAAACCGGGACAGCCACCCAAATTCCTC
ATCTATCTTGCATCCAACCTAGATTCTGGGGTCCCTGCCAGGTTCAGTGGC
AGTGGGTCTGGGACAGACTTCACCCTCAACATCCATCCTGTGGAGGAGGAG
GATGCTGCAACCTATTACTGTCAGCACAGTAGGGAGCTTCCGTACACGTTC
GGAGGGGGGACCAAGCTGGAAATAAAA (SEQ ID NO: 106)
DIVLTQSPASLAVSLGQRATISCRASKSVSTSGYSYIHWYQQKPGQPPKFL
IYLASNLDSGVPARFSGSGSGTDFTLNIHPVEEEDAATYYCQHSRELPYTF
GGGTKLEIK (SEQ ID NO: 107)

31H9vk  GACATTGTGATGACTCAGTCTCCAGCCACCCTGTCTGTGACTCCAGGAGAT
AGAGTCTCTCTTTCCTGCAGGGCCAGCCAGAGTATTAGCGACTACTTACAC
TGGTATCAACAAAAATCACATGAGTCTCCAAGGCTTCTCATCAAATATGCT
TCCCAATCCATCTCTGGGATCCCCTCCAGGTTCAGTGGCAGTGGATCAGGG
TCAGATTTCACTCTCAGTATCAACAGTGTGGAACCTGAAGATGTTGGAGTG
TATTACTGTCAAAATGGTCACAGCTTTCCGTACACGTTCGGAGGGGGGACC
AAGCTGGAAATAAAA (SEQ ID NO: 108)
DIVMTQSPATLSVTPGDRVSLSCRASQSISDYLHWYQQKSHESPRLLIKYA
SQSISGIPSRFSGSGSGSDFTLSINSVEPEDVGVYYCQNGHSFPYTFGGGT
KLEIK (SEQ ID NO: 109)

34G3Vk  GATGTTGTGATGACCCAAACTCCACTCTCCCTGCCTGTCAGTCTTGGAGAT
CAAGCCTCCATCTCTTGCAGATCTAGTCAGAGCCTTGTACACAGTAATGGA
AACACCTATTTACATTGGTACCTGCAGAAGCCAGGCCAGTCTCCAAAGCTC
CTGATCTACAAAGTTTCCAACCGATTTTCTGGGGTCCCCGACAGGTTCAGT
GGCAGTGGATCAGGGACAGATTTCACACTCAAGATCAGCAGAGTGGAGGCT
GAGGATCTGGGAGTTTATTTCTGCTCTCAAAGTACACATGTTCCGTACACG
TTCGGAGGGGGGACCAAGCTGGAAATAAAT (SEQ ID NO: 110)
DVVMTQTPLSLPVSLGDQASISCRSSQSLVHSNGNTYLHWYLQKPGQSPKL
LIYKVSNRFSGVPDRFSGSGSGTDFTLKISRVEAEDLGVYFCSQSTHVPYT
FGGGTKLEIN (SEQ ID NO: 111)

34D9Vk  GACATTATGATGACCCAGTCTCACAAATTCATGTCCACATCAGTAGGAGAC
AGGGTCAGCATCACCTGCAAGGCCAGTCAGGATGTGGGTAATGCTGTGGTC
TGGTATCAACAAAAACCAGGGCAATCTCCTAAACTACTGATTTACTGGGCA
TCCACCCGGCACATTGGAGTCCCTGATCGCTTCACAGGCAGTGGATCTGGG
ACAGATTTCACTCTCACCATTACCAATGTGCAGTCTGAAGACTTGGCAGAT
TATTTCTGTCAGCAATATAGCAGCTATCTCACGTTCGGTGCTGGGACCAAG
CTGGAGCTGAAA (SEQ ID NO: 112)
DIMMTQSHKFMSTSVGDRVSITCKASQDVGNAVVWYQQKPGQSPKLLIYWA
STRHIGVPDRFTGSGSGTDFTLTITNVQSEDLADYFCQQYSSYLTFGAGTK
LELK (SEQ ID NO: 113)

TABLE 1-continued

Anti-IL-23p19 Mouse Leads - VK Sequences

43F5vk   GATGTTGTGATGACCCAATCTCCACTCTCCCTGCCTGTCAGTCTTGGAGAT
         CAAGCCTCCATCTCTTGCAGATCTAGTCAGAGCCTTGTACACAGTAATGGA
         AACACCTATCTACATTGGTACCTGCTGAAGCCAGGCCAGTCTCCAAAGCTC
         CTGATCTACAAAGTTTCCAACCGATTTTCTGGGGTCCCAGACAGGTTCAGT
         GGCAGTGGATCAGGGACAGATTTCACACTCAAGATCAGCAGAGTGGAGGCT
         GAGGATCTGGGAGTTTATTTCTGCTCTCAAAGTACACATGTTCCGTACACG
         TTCGGAGGGGGGACCAAGCTGGAAATAAAA (SEQ ID NO: 114)
         DVVMTQSPLSLPVSLGDQASISCRSSQSLVHSNGNTYLHWYLLKPGQSPKL
         LIYKVSNRFSGVPDRFSGSGSGTDFTLKISRVEAEDLGVYFCSQSTHVPYT
         FGGGTKLEIK (SEQ ID NO: 115)

73H10Vk  GACATCCAGATGACTCAGTCTCCAGTTTTCCTGTCTGCATCTGTGGGAGAA
         ACTGTCACCATCACATGTCGAGCAAGTGAGAATATTGACAGTTATTTAGCA
         TGGTATCAGCAGAAACAGGGAAAATCTCCTCAGCTCCTGGTCTTTGCTGCA
         CGAAACTTAGCAGATGGTGTGCCATCAAGGTTCAGTGGCAGTGGATCAGGC
         ACACAGTATTCTCTCAAGATCAACAGAATGCAGTCTGAAGATGTTGCGAGA
         TACTACTGTCAACATTATTATAGTACTCCATTCACGTTCGGCTCGGGGACA
         AAGTTGGAAATAGAA (SEQ ID NO: 116)
         DIQMTQSPVFLSASVGETVTITCRASENIDSYLAWYQQKQGKSPQLLVFAA
         RNLADGVPSRFSGSGSGTQYSLKINRMQSEDVARYYCQHYYSTPFTFGSGT
         KLEIE (SEQ ID NO: 117)

74H3Vk   GACATCCAGATGACTCAGTCGCCAGCTTCCCTGTCTGCATCTGTGGGAGAA
         ACTGTCATCTTCACATGTCGAGCAAGTGAGAATATTGACAGTTATTTAGCA
         TGGTATCAGCAGAAACAGGGAAAATCTCCTCAGCTCCTGGTCTATGCTGCA
         ACAAACTTAGCAGATGGTGTGCCATCAAGGTTCAGTGGCAGTGGATCAGGC
         ACACAGTATTCTCTCAAGATCAACAGCCTGCAGTCTGAAGATGTTGCGAGA
         TATTACTGTCTACATTATTATAGTACTCCATTCACGTTCGGCTCGGGGACA
         GAGTTGGAAATAAAA (SEQ ID NO: 118)
         DIQMTQSPASLSASVGETVIFTCRASENIDSYLAWYQQKQGKSPQLLVYAA
         TNLADGVPSRFSGSGSGTQYSLKINSLQSEDVARYYCLHYYSTPFTFGSGT
         ELEIK (SEQ ID NO: 119)

TABLE 2

Anti-IL-23p19 Mouse Leads - VH Sequences

2D1vh    CAGGTGCAGCTGAAGGAGTCAGGACCTGGCCTGGTGGCGCCCTCACAGAGC
         CTGTCCATCACATGCACTGTCTCTGGGTTCTCATTAACCACCTATGCTATA
         AGCTGGGTTCGCCAGTCACCAGGAAAGGGTCTGGAGTGGCTTGGAGTCATA
         TGGACTGGTGGAGGCACAAAATATAATTCAGCTCTCAAATCCAGACTGAGC
         ATCAGCAAAGACAACTCCAAGAGTCAAGTTTTCTTAAAAATGAACAGTCTG
         CAAACTGATGACACAGCCAGGTACTACTGTGCCAGAAAGGACTATAATTAC
         GGGGGTGCTATGGACTACTGGGGTCAAGGAACCTCAGTCACCGTCTCCTCA
         (SEQ ID NO: 120)
         QVQLKESGPGLVAPSQSLSITCTVSGFSLTTYAISWVRQSPGKGLEWLGVI
         WTGGGTKYNSALKSRLSISKDNSKSQVFLKMNSLQTDDTARYYCARKDYNY
         GGAMDYWGQGTSVTVSS (SEQ ID NO: 121)

6B8VH    CAGGTTCAGCTGCAACAGTCTGACGCTGAGTTGGTGAAACCTGGCACTTCA
         GTGAAGACATCCTGCAAAATTTCTGGCAACACCTTCACTGACCAAACTATT
         CACTGGATGAAGCAGAGGCCTGAACAGGGCCTGGAATGGATTGGATATATT
         TATCCTAGAGATGATAGTCCTAAGTACAATGAGAACTTCAAGGGCAAGGCC
         ACATTGACTGCAGACAAATCCTCCAGCACAGCCTACATGCAGCTCAACAGT
         CTGACATCTGAGGACTCTGCAGTCTATTTCTGTGCAATCCCAGACAGGTCA
         GGCTACGCCTGGTTTATTTACTGGGCCAAGGGACTCTGGTCACTGTCTCT
         TCA (SEQ ID NO: 122)
         QVQLQQSDAELVKPGTSVKTSCKISGNTFTDQTIHWMKQRPEQGLEWIGYI
         YPRDDSPKYNENFKGKATLTADKSSSTAYMQLNSLTSEDSAVYFCAIPDRS
         GYAWFIYWGQGTLVTVSS (SEQ ID NO: 123)

9D12VH   CAGGTGCAGCTGAAGGAGTCAGGACCTGTCCTGGTGGCGCCCTCACAGAGC
         CTGTCCATCACATGCACTGTCTCTGGGTTCTCATTAAACAACTTTGCTATA
         AGTTGGGTTCGTCAGCCACCAGGAAAGGGTCTGGAGTGGCTTGGAGCAATA
         TGGACTGGTGGAGGCACAAATTATAATTCAGCTCTCAAATCCAGACTGAGC
         ATCAGCAAAGACAACTCCAAGAGTCAAGTTTTCTTAAAAATGAACAGTCTG
         CAAACTGATGACACAGCCAGGTATTATTGTGTCAGAAAGGACTATAGTTAC
         GGGGGTGCTATGGACTACTGGGGTCAAGGAACCTCAGTCACCGTCTCCTCA
         (SEQ ID NO: 124)
         QVQLKESGPVLVAPSQSLSITCTVSGFSLNNFAIAWVRQPPGKGLEWLGAI
         WTGGGTNYNSALKSRLSISKDNSKSQVFLKMNSLQTDDTARYYCVRKDYSY
         GGAMDYWGQGTSVTVSS (SEQ ID NO: 125)

15C11vh  GAGGTCCAGCTGCAACAGTCTGGACCTGTGCTGGTGAAGCCTGGGGCTTCA
         GTGAAGATGTCCTGTAAGGCTTCTGGATACACATTCACTGACTACTATATG

TABLE 2-continued

Anti-IL-23p19 Mouse Leads - VH Sequences

AACTGGGTGAAGCAGAGCCATGGAAAGAGCCTTGAGTGGATTGGAGTTATT
ATTCCTTACAACGGTGGTACTAGCTACAACCAGAAGTTCAAGGGCAAGGCC
ACATTGACTGTTGACAAGTCCTCCAGCACAGCCTACATGGAGCTCAACAGC
CTGACATCTGAGGACTCTGCAGTCTATTACTGTGCACGAGATGGTCACCGC
TGGTACTTCGATGTCTGGGGCACAGGGACCACGGTCACCGTCTCCTCA
(SEQ ID NO: 126)
EVQLQQSGPVLVKPGASVKMSCKASGYTFTDYYMNWVKQSHGKSLEWIGVI
IPYNGGTSYNQKFKGKATLTVDKSSSTAYMELNSLTSEDSAVYYCARDGHR
WYFDVWGTGTTVTVSS (SEQ ID NO: 127)

15F1vh    EVQLQQSGPELVKPGASVKMSCKASGYTFTCCIMHWVKQPGQGLEWIGYI
NPYNDGTKYNEKFKGKATLTSDKSSSTAYMELSSLTSEDSAVYYCARRWDE
AYWGQGTLVTVSA (SEQ ID NO: 128)

18D3vh    GAGGTCCAGCTGCAGCAGTCTGGACCTGAGCTGGTCAAGCCTGGGGCTTCA
GTGAAGATGTCCTGCAAGGCTTCTGGATACACATTCACTCGCTATCTTATT
CACTGGGTGAAACAGAAGCCTGGGCAGGGCCTTGAGTGGATTGGATATATT
AATCCTTACAATGATGGTACTAAATACAATGAGAAGTTCAAGGCAAGGCC
ACACTGACTTCAGACAAATCCTCCAGCACAGCCTACATGGAGCTCAGCAGC
CTGACCTCTGAGGACTCTGCGGTCTATTACTGTACCTCTAACTGGGACCTC
GACTACTGGGGCCAAGGCACCACTCTCACAGTCTCCTCA (SEQ ID
NO: 129)
EVQLQQSGPELVKPGASVKMSCKASGYTFTRYLIHWVKQPGQGLEWIGYI
NPYNDGTKYNEKFKGKATLTSDKSSSTAYMELSSLTSEDSAVYYCTSNWDL
DYWGQGTTLTVSS (SEQ ID NO: 130)

18C4vh    GAGGTCCAGCTGCAGCAGTCTGGACCTGAAGTGGTAAAGCCTGGGGCTTCA
GTGAAGATGTCCTGCAAGGCTCTGGATACACATTCACTAGTTCTGTTATA
CACTGGGTGAAGCAGAAGGCTGGGCAGGGCCTTGAGTGGATTGGATATATC
AATCCCTATAATGATGGTACTAAGTACAATGAGAAGTTCAAAGGCAAGGCC
ACACTGACTTCAGACAGATCCTCCAGCACAGCCTACATGGAGCTCAGCAGC
CTGACCTCTGAGGACTCTGCGGTCTATTACTGTACAAGACGGTTGGACGAG
GCTTACTGGGGCCAAGGGACTCTGGTCACTGTCTCTGCA (SEQ ID
NO: 131)
EVQLQQSGPEVVKPGASVKMSCKASGYTFTSSVIHWVKQKAGQGLEWIGYI
NPYNDGTKYNEKFKGKATLTSDRSSSTAYMELSSLTSEDSAVYYCTRRLDE
AYWGQGTLVTVSA (SEQ ID NO: 132)

18E5vh    GAGGTCCAGCTGCAGCAGTCTGGACCTGAGCTGGTAAAGCCTGGGGCTGCA
GTGAAGATGTCCTGCAAGGCTTCTGGATACACATTCACTCGCTATCTTATT
CACTGGGTGAAGCAGAAGCCTGGGCAGGGCCTTGAGTGGATTGGATATATT
AATCCTTACAATGATGGTACTAAATATAATGAGAAGTTCAAGGCAAGGCC
ACACTGACTTCAGACAAATCCTCCAGCACAGCCTACATGGAGCTCAGCAGC
CTGACCTCTGAGGACTCTGCGGTCTATTACTGTACCTCTAATTGGGACCTC
GACTACTGGGGCCAAGGCACCACTCTCACAGTCTCCTCA (SEQ ID
NO: 133)
EVQLQQSGPELVKPGAAVKMSCKASGYTFTRYLIHWVKQPGQGLEWIGYI
NPYNDGTKYNEKFKGKATLTSDKSSSTAYMELSSLTSEDSAVYYCTSNWDL
DYWGQGTTLTVSS (SEQ ID NO: 134)

20E8vh    GAGGTCCAGCTGCAGCAGTCTGGACCTGAACTGGTAAAGCCTGGGGCTTCA
GTGAAGATGTCCTGCAAGGCCTCTGGATACACATTCACTAGTTCTGTTATG
CACTGGGTGAAGCAGAAGGCTGGGCAGGGCCTTGAGTGGATTGGATATATC
AATCCCTATAATGATGGTACTCAGTACAATGAGAAGTTCAAAGGCAAGGCC
ACACTGACTTCAGACAAATTTTCCAGCACAGCCTACATGGAGCTCAGCAGC
CTGACCTCTGAGGACTCTGCGGTCTATTACTGTACAAGACGGTTGGACGAG
GCTTACTGGGGCCAAGGGACTCTGGTCACTGTCTCTGCA (SEQ ID
NO: 135)
EVQLQQSGPELVKPGASVKMSCKASGYTFTSSVMHWVKQKAGQGLEWIGYI
NPYNDGTQYNEKFKGKATLTSDKFSSTAYMELSSLTSEDSAVYYCTRRLDE
AYWGQGTLVTVSA (SEQ ID NO: 136)

22E2vh    GAGGTCCAGCTGCAGCAGTCTGGACCTGAGCTGGTAAAGCCTGGGGCTTCA
GTGAAGATGTCCTGCAAGGCTTCTGGATACACATTCACTAGCTCTATTATT
CACTGGGTGAAGCAGAGGCCTGGGCAGGGCCTTGAGTGGATTGGATATATT
AATCCTTACGATGATGTTACTAAGTACAATGAGAAGTTCAAAGGCAAGGCC
ACACTGACTTCAGACAAATCCTCCAGCACAGCCTACATGGAGCTCAGCAGC
CTGACCTCTGAGGACTCTGCGGTCTATTACTGTGCAAGACGGTGGGACGAG
TCTTACTGGGGCCAAGGGACTCTGGTCACTGTCTCTGCA (SEQ ID
NO: 137)
EVQLQQSGPELVKPGASVKMSCKASGYTFTSSIIHWVKQRPGQGLEWIGYI
NPYDDVTKYNEKFKGKATLTSDKSSSTAYMELSSLTSEDSAVYYCARRWDE
SYWGQGTLVTVSA (SEQ ID NO: 138)

24A5vh    GAGGTCCAGCTGCAGCAGTCTGGACCTGAGCTGGTAAAGCCTGGGGCTTCA
GTGAAGATGTCCTGCAAGGCTTCTGGATACACTTTCACTACCTCTATTATG
CACTGGGTGAAACAGAAGCCTGGGCAGGGCCTTGAGTGGATTGGATATATT
AATCCTTACGATGATGTTACTAAGTACAATGAAAAGTTCAAAGGCAAGGCC

TABLE 2-continued

Anti-IL-23p19 Mouse Leads - VH Sequences

ACATTGACTTCAGACAAATCCTCCAGCACAGCCTACATGGAGCTCAGCAGC
CTGACCTCTGAGGACTCTGCAGTCTATTACTGTGTAAGACGGTGGGACGAG
GCTTACTGGGGCCAAGGGACTCTGGTCACTGTCTCTGCA (SEQ ID
NO: 139)
EVQLQQSGPELVKPGASVKMSCKASGYTFTTSIMHWVKQKPGQGLEWIGYI
NPYDDVTKYNEKFKGKATLTSDKSSSTAYMELSSLTSEDSAVYYCVRRWDE
AYWGQGTLVTVSA (SEQ ID NO: 140)

26F7VH
GAGGTCCAGCTGCAACAATCTGGACCTGAGCTGGTGAAGCCTGGGGCTTCA
GTGAAGATATCCTGTAAGGCTTCTGGATACACGTTTACTGACTACTACATG
AACTGGGTGAGGCAGAGCCATGGAGAGAGCCTTGAGTGGATTGGAGATTTT
AATCATAACAATGATGTTATTACTTACAACCCGAAGTTCAAGGGCAAGGTC
ACATTGACTGTAGAGAAGTCTTCCACCACAGCCTACATGGAGCTCCGCAGC
CTGTCATCTGAGGACTCTGCAGTCTATTACTGTGCAAGGGGGCTACGAGGC
TACTATGCTATGGACTACTGGGGTCAAGGAACCTCAGTCACCGTCTCCTCA
(SEQ ID NO: 141)
EVQLQQSGPELVKPGASVKISCKASGYTFTDYYMNWVRQSHGESLEWIGDF
NHNNDVITYNPKFKGKVTLTVEKSSTTAYMELRSLSSEDSAVYYCARGLRG
YYAMDYWGQGTSVTVSS (SEQ ID NO: 142)

27G8vh
CAGGTTCAGCTGCAACAGTCTGACGCTGAGTTGGTGAAACCTGGAGCTTCA
GTGAAGATATCCTGCAAGGTTTCTGGCTACACCTTCACTGACCATACTATT
CACTGGATGAAGCAGAGGCCTGAACAGGGCCTGGAATGGATTGGATATATT
TATCCTAGAGATGGTTATCCTAAGTTCAATGAGAAGTTCAAGGGCAAGGCC
ACATTGACTGCAGACAAATCCTCCAGCACAGCCTACATGCAGCTCAACAGC
CTGACATCTGAGGACTCTGCAGTCTATTTCTGTGCAAGACGGCCCCCTTAC
TATGCTATGGACTACTGGGGTCAAGGAACCTCAGTCGCCGTCTCCTCA
(SEQ ID NO: 143)
QVQLQQSDAELVKPGASVKISCKVSGYTFTDHTIHWMKQRPEQGLEWIGYI
YPRDGYPKFNEKFKGKATLTADKSSSTAYMQLNSLTSEDSAVYFCARRPPY
YAMDYWGQGTSVAVSS (SEQ ID NO: 144)

31H9vh
GAGGTCCAACTGCAGCAGTCTGGACCTGAGCTGGTAAAGCCTGGGGCTTCA
GTGAAGATGTCCTGCAAGGCTTCTGGATACACATTCACTAGGTATCTTATG
CACTGGGTGAAGCAGAAGCCTGGGCAGGGCCTTGAGTGGATTGGTTATATT
AATCCTTACAATGATGGTACTAATTACAATGAGAAGTTCAAAGGCAAGGCC
ACACTGACTTCAGACAAATCCTCCAGCACAGCCTACATGGAGCTCAGCAGC
CTGACCTCTGAGGACTCTGCGGTCTATTACTGTTCCCTTAACTGGGACTAT
GCTTACTGGGGCCAAGGGACTCTGGTCACTGTCTCTGCA (SEQ ID
NO: 145)
EVQLQQSGPELVKPGASVKMSCKASGYTFTRYLMHWVKQKPGQGLEWIGYI
NPYNDGTNYNEKFKGKATLTSDKSSSTAYMELSSLTSEDSAVYYCSLNWDY
AYWGQGTLVTVSA (SEQ ID NO: 146)

34G3VH
GAGTTCCAGCTGCAGCAGTCTGGACCTGAGCTGGTGAAGCCTGGCGCTTCA
GTGAAGATATCCTGCAAGGCTTCTGGTTACTCATTCACTGACTACAACATG
AACTGGGTGAAGCAGAGCAAAGGAAAGAGCCTTGAGTGGATTGGAGTAATT
ATTCCTAACTATGGTTTTACTAGCTACAATCAGAACTTCAAGGGCAAGGCC
ACTTTGACTGTAGACCAGTCTTCCAGCACAGCCCACATGCAGCTCAACAGT
GTGACATCTGAGGACTCTGCAGTCTATTACTGTGTAAGAGATGGGGAATA
CTCCTCTGGTATCTCGATGTCTGGGGCACAGGGACCACGGTCACCGTCTCC
TCA (SEQ ID NO: 147)
EFQLQQSGPELVKPGASVKISCKASGYSFTDYNMNWVKQSKGKSLEWIGVI
IPNYGFTSYNQNFKGKATLTVDQSSSTAHMQLNSVTSEDSAVYYCVRDGGI
LLWYLDVWGTGTTVTVSS (SEQ ID NO: 148)

34D9VH7
GAGGTCCAGCTGCAACAGTCTGGACCTGAGCTGGTGAAGCCTGGGGCTTCA
GTGAAGATACCCTGCAAGGCTTCTGGATACACATTCACTGACTACAACATG
GACTGGGTGAAGAAGAGCCATGGAAAGAGCCTTGAGTGGATTGGAGATATC
AATCCTCACAATGGTGGTACTATCTACAACCAGAAGTTCAAGGGCAAGGCC
ACATTGACTGTAGACAAGTCCTCCAGCACAGCCCACATGGAGCTCCGCAGC
CTGACATCTGAGGACACTGCAGTCTATTACTGTGCAAGAAATTACTACGGT
AGTAGTTACGGCTGGTACTTCGATGTCTGGGGCACAGGGACCACGGTCACC
GTCTCGTCA (SEQ ID NO: 149)
EVQLQQSGPELVKPGASVKIPCKASGYTFTDYNMDWVKKSHGKSLEWIGDI
NPHNGGTIYNQKFKGKATLTVDKSSSTAHMELRSLTSEDTAVYYCARNYYG
SSYGWYFDVWGTGTTVTVSS (SEQ ID NO: 150)

43F5vh
GAGGTCCAGCTGCAGCAGTCTGGACCTGAGCTGGTGAAGCCTGGGGCTTCA
GTGAAGATTTCCTGCAGGGCTTCTGGTTACTCATTCACTGGCTACTACATG
AACTGGGTGAAGCAAAGTCCTGAAAAGAGCCTTGAGTGGATTGGAGAGATT
ATTCCTACCACTGGTGGTACTTCCTACAACCAGAAGTTCAAGGCCAAGGCC
ACATTGACTGTAGACAAATCCTCCAGCACAGCCTACATGCAGCTCAAGAGC
CTGACATCTGAGGACTCTGCAGTCTATTACTGTGCAAGAGAGAGCGGTGGG
TTCTACTGGTACTTCGATGTCTGGGGCACAGGGACCACGGTCACCGTCTCC
TCA (SEQ ID NO: 151)

TABLE 2-continued

Anti-IL-23p19 Mouse Leads - VH Sequences

```
        EVQLQQSGPELVKPGASVKISCRASGYSFTGYYMNWVKQSPEKSLEWIGEI
        IPTTGGTSYNQKFKAKATLTVDKSSSTAYMQLKSLTSEDSAVYYCARESGG
        FYWYFDVWGTGTTVTSS (SEQ ID NO: 152)

73H10VH GAGGTCCAGCTGCAGCAGTCTGGACCTGAGCTGGTAAAGCCTGGGGCTTCA
        GTGAAGATGTCCTGCAAGGCTTCTGGATACACATTCACTAGGTATGTTATG
        CACTGGGTGAAGCAGAAGCCTGGGCAGGGCCTTGAGTGGATTGGATATATT
        AATCCTTACAATGATGTTACTAAGTACAATGAGAAGTTCAAAGGCAAGGCC
        ACACTGACTTCAGACAGATCCTCCAGCACAGCCTACATGAAACTCAGCAGC
        CTGACCTCTGAGGACTCTGCGGTCTATTATTGTGCAAGAAACTGGGACGTT
        CCTTACTGGGGCCAAGGGACTCTGATCACTGTCTCTGCA (SEQ ID
        NO: 153)
        EVQLQQSGPELVKPGASVKMSCKASGYTFTRYVMHWVKQKPGQGLEWIGYI
        NPYNDVTKYNEKFKGKATLTSDRSSSTAYMKLSSLTSEDSAVYYCARNWDV
        PYWGQGTLITVSA (SEQ ID NO: 154)

74H3VH  GAGGTCCAGCTGCAGCAGTCTGGACCTGAGCTGGTAAAGCCTGGGGCTTCA
        GTGAAGATGTCCTGCAAGGCTTCTGGATACACATTCACTAGGTATCTTATG
        CACTGGGTGAAGCAGAAGCCTGGACAGGGCCTTGAGTGGATTGGATATATT
        AATCCTTACAATGATGGTACTAAGTACAATGAGAGGTTCAAAGGCAAGGCC
        ACACTGACTTCAGACAAATCCTCCAGCACAGCCTACATGGAGCTCAGCAGC
        CTGACCTCTGAGGACTCTGCGGTCTATTACTGTGCAAGAAACTGGGACGTA
        CCTTACTGGGGCCAAGGGACTCTGGTCACTGTCTCTGCA (SEQ ID
        NO: 155)
        EVQLQQSGPELVKPGASVKMSCKASGYTFTRYLMHWVKQKPGQGLEWIGYI
        NPYNDGTKYNERFKGKATLTSDKSSSTAYMELSSLTSEDSAVYYCARNWDV
        PYWGQGTLVTVSA (SEQ ID NO: 156)
```

Human framework sequences were selected for each of the mouse leads based on the framework homology, CDR structure, conserved canonical residues, conserved interface packing residues and other parameters.

The mouse light chain and heavy chain CDRs of the various mouse antibodies are shown in Table 3 and Table 4, respectively. Table 4 also shows three heavy chains CDRs derived from the mouse antibody 6B8 through the humanization process.

TABLE 3

LIGHT CHAIN CDR sequences

| | L-CDR1 | L-CDR2 | L-CDR3 |
|---|---|---|---|
| 18C4 | RASQSISEYLH (SEQ ID NO: 1) | YASQSIS (SEQ ID NO: 2) | QNGHSFPFT (SEQ ID NO: 3) |
| 18E5 | RASQSISDYLY (SEQ ID NO: 4) | FASQSIS (SEQ ID NO: 5) | QNGHSFPFT (SEQ ID NO: 3) |
| 18D3 | RASQSISDYLY (SEQ ID NO: 4) | FASQSIS (SEQ ID NO: 5) | QNGHSFPFT (SEQ ID NO: 3) |
| 20E8 | RASQSISEYLH (SEQ ID NO: 1) | YASQSIS (SEQ ID NO: 2) | QNGHSFPFT (SEQ ID NO: 3) |
| 22E2 | RASQSISVYLH (SEQ ID NO: 6) | YASQSIS (SEQ ID NO: 2) | QNGHSFPFT (SEQ ID NO: 3) |
| 24A5 | RASQSISDYLH (SEQ ID NO: 7) | YASQSIS (SEQ ID NO: 2) | QNGHSFPFT (SEQ ID NO: 3) |
| 15C11 | RSSQSLVHSNGNTYLH (SEQ ID NO: 8) | KVSNRFS (SEQ ID NO: 9) | SQSTHVPYT (SEQ ID NO: 10) |

TABLE 3-continued

LIGHT CHAIN CDR sequences

| | L-CDR1 | L-CDR2 | L-CDR3 |
|---|---|---|---|
| 43F5 | RSSQSLVHSNGNTYLH (SEQ ID NO: 8) | KVSNRFS (SEQ ID NO: 9) | SQSTHVPYT (SEQ ID NO: 10) |
| 27G8 | RASKSVSTSGYSYIH (SEQ ID NO: 11) | LASNLDS (SEQ ID NO: 12) | QHSRELPYT (SEQ ID NO: 13) |
| 31H9 | RASQSISDYLH (SEQ ID NO: 7) | YASQSIS (SEQ ID NO: 2) | QNGHSFPYT (SEQ ID NO: 14) |
| 2D1 | RTSESVYSYGQNFIH (SEQ ID NO: 15) | RASNLES (SEQ ID NO: 16) | QQTNEDPYT (SEQ ID NO: 17) |
| 9D12 | RASETINFYGTSFMH (SEQ ID NO: 18) | RASNLES (SEQ ID NO: 16) | QQTNEDPYT (SEQ ID NO: 17) |
| 6B8 | KASRDVAIAVA (SEQ ID NO: 19) | WASTRHT (SEQ ID NO: 20) | HQYSSYPFT (SEQ ID NO: 21) |
| 73H10 | RASENIDSYLA (SEQ ID NO: 22) | AARNLAD (SEQ ID NO: 23) | QHYYSTPFT (SEQ ID NO: 24) |
| 74H3 | RASENIDSYLA (SEQ ID NO: 22) | AATNLAD (SEQ ID NO: 25) | LHYYSTPFT (SEQ ID NO: 26) |
| 35H8 | RSSQSLVHSNGNTYLH (SEQ ID NO: 8) | KVSNRFS (SEQ ID NO: 9) | SQSTHVPYT (SEQ ID NO: 10) |
| 26F7 | RASKSVRFSDYFYMH (SEQ ID NO: 27) | LASNLES (SEQ ID NO: 28) | QNSRELPYT (SEQ ID NO: 29) |

TABLE 3-continued

LIGHT CHAIN CDR sequences

| | L-CDR1 | L-CDR2 | L-CDR3 |
|---|---|---|---|
| 34G3 | RSSQSLVHSNGNTYLH (SEQ ID NO: 8) | KVSNRFS (SEQ ID NO: 9) | SQSTHVPYT (SEQ ID NO: 10) |

TABLE 3-continued

LIGHT CHAIN CDR sequences

| | L-CDR1 | L-CDR2 | L-CDR3 |
|---|---|---|---|
| 34D9 | KASQDVGNAVV (SEQ ID NO: 30) | WASTRHI (SEQ ID NO: 31) | QQYSSYLT (SEQ ID NO: 32) |

TABLE 4

HEAVY CHAIN CDR sequences

| | H-CDR1 | H-CDR2 | H-CDR3 |
|---|---|---|---|
| 18C4 | GYTFTSSVIH (SEQ ID NO: 33) | YINPYNDGTKYNEKFKG (SEQ ID NO: 34) | RLDEAY (SEQ ID NO: 35) |
| 18E5 | GYTFTRYLIH (SEQ ID NO: 36) | YINPYNDGTKYNEKFKG (SEQ ID NO: 34) | NWDLDY (SEQ ID NO: 37) |
| 18D3 | GYTFTRYLIH (SEQ ID NO: 36) | YINPYNDGTKYNEKFKG (SEQ ID NO: 34) | NWDLDY (SEQ ID NO: 37) |
| 20E8 | GYTFTSSVMH (SEQ ID NO: 38) | YINPYNDGTQYNEKFKG (SEQ ID NO: 39) | RLDEAY (SEQ ID NO: 35) |
| 22E2 | GYTFTSSIIH (SEQ ID NO: 40) | YINPYDDVTKYNEKFKG (SEQ ID NO: 41) | RWDESY (SEQ ID NO: 42) |
| 24A5 | GYTFTTSIMH (SEQ ID NO: 43) | YINPYDDVTKYNEKFKG (SEQ ID NO: 41) | RWDEAY (SEQ ID NO: 44) |
| 15C11 | GYTFTDYYMN (SEQ ID NO: 45) | VIIPYNGGTSYNQKFKG (SEQ ID NO: 46) | DGHRWYFDV (SEQ ID NO: 47) |
| 43F5 | GYSFTGYYMN (SEQ ID NO: 48) | EIIPTTGGTSYNQKFKA (SEQ ID NO: 49) | ESGGFYWYFDV (SEQ ID NO: 50) |
| 27G8 | GYTFTDHTIH (SEQ ID NO: 51) | YIYPRDGYPKFNEKFKG (SEQ ID NO: 52) | RPPYYAMDY (SEQ ID NO: 53) |
| 31H9 | GYTFTRYLMH (SEQ ID NO: 54) | YINPYNDGTNYNEKFKG (SEQ ID NO: 55) | NWDYAY (SEQ ID NO: 56) |
| 2D1 | GFSLTTYAIS (SEQ ID NO: 57) | VIWTGGGTKYNSALKS (SEQ ID NO: 58) | KDYNYGGAMDY (SEQ ID NO: 59) |
| 9D12 | GFSLNNFAIS (SEQ ID NO: 60) | AIWTGGGTNYNSALKS (SEQ ID NO: 61) | KDYSYGGAMDY (SEQ ID NO: 62) |
| 6B8 | GNTFTDQTIH (SEQ ID NO: 63) | YIYPRDDSPKYNENFKG (SEQ ID NO: 64) | PDRSGYAWFIY (SEQ ID NO: 65) |
| Hu_6B8-2 | GYTFTDQTIH (SEQ ID NO: 66) | YIYPRDDSPKYNENFKG (SEQ ID NO: 64) | PDRSGYAWFIY (SEQ ID NO: 65) |
| Hu_6B8-5 | GFTFTDQTIH (SEQ ID NO: 67) | YIYPRDDSPKYNENFKG (SEQ ID NO: 64) | PDRSGYAWFIY (SEQ ID NO: 65) |
| Hu_6B8-36/65 | GGTFTDQTIH (SEQ ID NO: 68) | YIYPRDDSPKYNENFKG (SEQ ID NO: 64) | PDRSGYAWFIY (SEQ ID NO: 65) |
| 73H10 | GYTFTRYVMH (SEQ ID NO: 69) | YINPYNDVTKYNEKFKG (SEQ ID NO: 70) | NWDVPY (SEQ ID NO: 71) |
| 74H3 | GYTFTRYLMH (SEQ ID NO: 54) | YINPYNDGTKYNERFKG (SEQ ID NO: 72) | NWDVPY (SEQ ID NO: 71) |
| 35H8 | GYTFTDYYMN (SEQ ID NO: 45) | VIIPYNGGISYNQKFKG (SEQ ID NO: 73) | NDYDWYFDV (SEQ ID NO: 74) |
| 26F7 | GYTFTDYYMN (SEQ ID NO: 45) | DFNHNNDVITYNPKFKG (SEQ ID NO: 75) | GLRGYYAMDY (SEQ ID NO: 76) |
| 34G3 | GYSFTDYNMN (SEQ ID NO: 77) | VIIPNYGFTSYNQNFKG (SEQ ID NO: 78) | DGGILLWYLDV (SEQ ID NO: 79) |

TABLE 4-continued

HEAVY CHAIN CDR sequences

| | H-CDR1 | H-CDR2 | H-CDR3 |
|---|---|---|---|
| 34D9 | GYTFTDYNMD (SEQ ID NO: 80) | DINPHNGGTIYNQKFKG (SEQ ID NO: 81) | NYYGSSYGWYFDV (SEQ ID NO: 82) |

The CDRs listed above in Tables 3 and 4 are defined using the Chothia numbering system (Al-Lazikani et al., (1997) JMB 273, 927-948).

Fabs that showed better or equal binding as compared to the chimeric parent Fab were selected for conversion to IgG. 6B8 was converted to an IgG1 KO format. IgG1 KO (knock-out of effector functions) has two mutations in the Fc region, Leu234Ala and Leu235Ala, which reduce effector function such as FcγR and complement binding. The IgG format is described in the literature (see for example Hezareh et al. (2001) Journal of Virology 75: 12161-12168). Example 1 describes the humanization process in further detail. The results of such humanization resulted in humanized antibody sequences. A representative number of humanized light chain and heavy chain variable regions derived from mouse antibody 6B8 are provided and shown in Tables 5 and 6. An alignment between the humanized light chain and heavy chain variable regions derived from mouse antibody 6B8 and the chain and heavy chain variable regions from mouse antibody 6B8 is shown in FIG. 1.

Selected combination of humanized light chain and heavy chain variable regions derived from mouse antibody 6B8 resulted in Antibodies A, B, C and D:

Antibody A: 6B8-IgG1 KO-2 with IgK-66 (heavy chain variable region 6B8CVH-02 and light chain variable region 6B8CVK-66);

Antibody B: 6B8-IgG1 KO-5 with IgK-66 (heavy chain variable region 6B8CVH-05 and light chain variable region 6B8CVK-66);

Antibody C: 6B8-IgG1 KO-2 with IgK-65 (heavy chain variable region 6B8CVH-02 and light chain variable region 6B8CVK-65);

Antibody D: 6B8-IgG1 KO-5 with IgK-65 (heavy chain variable region 6B8CVH-05 and light chain variable region 6B8CVK-65).

Antibodies A, B, C and D have the heavy and light chain sequences shown in Table 7.

TABLE 5

Humanized 6B8-VK Sequences

6B8CVK-65  Gacatccagatgacccagagcccaagcagcctgagcgccagcgtggg
cgaccgcgtgaccatcacctgcaaggccagccgcgacgtggccatcg
ccgtggcctggtaccagcagaagccaggcaaggtgccaaagctgctg
ctgttctgggccagcacccgccacaccggcgtgccagaccgcttcag
cggcagcggcagcggcaccgacttcaccctgaccatcagcagcctgc
agccagaggacctggccgactactactgccaccagtacagcagctac
ccattcaccttcggccagggcaccaagctggagatcaag (SEQ ID NO: 157)
DIQMTQSPSSLSASVGDRVTITCKASRDVAIAVAWYQQKPGKVPKLL
LFWASTRHTGVPDRFSGSGSGTDFTLTISSLQPEDLADYYCHQYSSY
PFTFGQGTKLEIK (SEQ ID NO: 158)

6B8CVK-66  Gacatccagatgacccagagcccaagcagcctgagcgccagcgtggg
cgaccgcgtgaccatcacctgcaaggccagccgcgacgtggccatcg
ccgtggcctggtaccagcagaagccaggcaaggtgccaaagctgctg
atctactgggccagcacccgccacaccggcgtgccaagccgcttcag
cggcagcggcagccgcaccgacttcaccctgaccatcagcagcctgc
agccagaggacgtggccgactacttctgccaccagtacagcagctac
ccattcaccttcggcagcggcaccaagctggagatcaag (SEQ ID NO: 159)
DIQMTQSPSSLSASVGDRVTITCKASRDVAIAVAWYQQKPGKVPKLL
IYWASTRHTGVPSRFSGSGSRTDFTLTISSLQPEDVADYFCHQYSSY
PFTFGSGTKLEIK (SEQ ID NO: 160)

6B8CVK-67  Gacatccagatgacccagagcccaagcagcctgagcgccagcgtggg
cgaccgcgtgaccatcacctgcaaggccagccgcgacgtggccatcg
ccgtggcctggtaccagcagaagccaggcaaggtgccaaagctgctg
ctgtactgggccagcacccgccacaccggcgtgccaagccgcttcag
cggcagcggcagccgcaccgacttcaccctgaccatcagcagcctgc
agccagaggacgtggccacctactactgccaccagtacagcagctac
ccattcaccttcggcagcggcaccaagctggagatcaag (SEQ ID NO: 161)
DIQMTQSPSSLSASVGDRVTITCKASRDVAIAVAWYQQKPGKVPKLL
LYWASTRHTGVPSRFSGSGSRTDFTLTISSLQPEDVATYYCHQYSSY
PFTFGSGTKLEIK (SEQ ID NO: 162)

6B8CVK-78  Gacatccagatgacccagagcccaagcagcctgagcgccagcgtggg
cgaccgcgtgaccatcacctgcaaggccagccgcgacgtggccatcg
ccgtggcctggtaccagcagaagccaggcaaggtgccaaagctgctg
ctgttctgggccagcacccgccacaccggcgtgccagaccgcttcag
cggcagcggcagccgcaccgacttcaccctgaccatcagcagcctgc
agccagaggacctggccgactactactgccaccagtacagcagctac
ccattcaccttcggcagcggcaccaagctggagatcaag (SEQ ID NO: 163)

TABLE 5-continued

Humanized 6B8-VK Sequences

DIQMTQSPSSLSASVGDRVTITCKASRDVAIAVAWYQQKPGKVPKLL
LFWASTRHTGVPDRFSGSGSRTDFTLTISSLQPEDLADYYCHQYSSY
PFTFGSGTKLEIK (SEQ ID NO: 164)

TABLE 6

Humanized 6B8-VH Sequence

| | |
|---|---|
| 6B8CVH-02 | Caggtgcagctggtgcagagcggcgccgaggtgaagaagccaggcag<br>cagcgtgaaggtgagctgcaaggccagcggctacaccttcaccgacc<br>agaccatccactggatgcgccaggcccaggccagggcctggagtgg<br>atcggctacatctacccacgcgacgacagcccaaagtacaacgagaa<br>cttcaagggcaaggtcaccatcaccgccgacaagagcaccagcaccg<br>cctacatggagctgagcagcctgcgcagcgaggacaccgccgtgtac<br>tactgcgccatcccagaccgcagcggctacgcctggttcatctactg<br>gggccagggcaccctggtgaccgtgagcagc (SEQ ID NO: 165)<br>QVQLVQSGAEVKKPGSSVKVSCKASGYTFTDQTIHWMRQAPGQGLEW<br>IGYIYPRDDSPKYNENFKGKVTITADKSTSTAYMELSSLRSEDTAVY<br>YCAIPDRSGYAWFIYWGQGTLVTVSS (SEQ ID NO: 166) |
| 6B8CVH-05 | Caggtgcagctggtgcagagcggcgccgaggtgaagaagccaggcag<br>cagcgtgaaggtgagctgcaaggccagcggcttcaccttcaccgacc<br>agaccatccactgggtgcgccaggcccaggccagggcctggagtgg<br>atgggctacatctacccacgcgacgacagcccaaagtacaacgagaa<br>cttcaagggcaaggtcaccctgaccgccgacaagagcaccagcaccg<br>cctacatggagctgagcagcctgcgcagcgaggacaccgccgtgtac<br>tactgcgccatcccagaccgcagcggctacgcctggttcatctactg<br>gggccagggcaccctggtgaccgtgagcagc (SEQ ID NO: 167)<br>QVQLVQSGAEVKKPGSSVKVSCKASGFTFTDQTIHWVRQAPGQGLEW<br>MGYIYPRDDSPKYNENFKGKVTLTADKSTSTAYMELSSLRSEDTAVY<br>YCAIPDRSGYAWFIYWGQGTLVTVSS (SEQ ID NO: 168) |
| 6B8CVH-36 | Caggtgcagctggtgcagagcggcgccgaggtgaagaagccaggcag<br>cagcgtgaagaccagctgcaaggccagcggcggcaccttcaccgacc<br>agaccatccactgggtgcgccagcccaggccagggcctggagtgg<br>atgggctacatctacccacgcgacgacagcccaaagtacaacgagaa<br>cttcaagggccgcgtcaccatcaccgccgacaagagcaccagcaccg<br>cctacatggagctgagcagcctgcgcagcgaggacaccgccgtgtac<br>tactgcgccatcccagaccgcagcggctacgcctggttcatctactg<br>gggccagggcaccctggtgaccgtgagcagc (SEQ ID NO: 169)<br>QVQLVQSGAEVKKPGSSVKTSCKASGGTFTDQTIHWVRQRPGQGLEW<br>MGYIYPRDDSPKYNENFKGRVTITADKSTSTAYMELSSLRSEDTAVY<br>YCAIPDRSGYAWFIYWGQGTLVTVSS (SEQ ID NO: 170) |
| 6B8CVH-65 | Caggtgcagctggtgcagagcggcgccgaggtgaagaagccaggcag<br>cagcgtgaaggtgagctgcaaggccagcggcggcaccttcaccgacc<br>agaccatccactgggtgcgccaggcccaggccagggcctggagtgg<br>atgggctacatctacccacgcgacgacagcccaaagtacaacgagaa<br>tttcaagggccgcgtcaccctgaccgccgacaagagcaccagcaccg<br>cctacatggagctgagcagcctgcgcagcgaggacaccgccgtgtac<br>ttctgcgcccgcccagaccgcagcggctacgcctggttcatctactg<br>gggccagggcaccctggtgaccgtgagcagc (SEQ ID NO: 171)<br>QVQLVQSGAEVKKPGSSVKVSCKASGGTFTDQTIHWVRQAPGQGLEW<br>MGYIYPRDDSPKYNENFKGRVTLTADKSTSTAYMELSSLRSEDTAVY<br>FCARPDRSGYAWFIYWGQGTLVTVSS (SEQ ID NO: 172) |

TABLE 7

Heavy and Light Chain DNA and Amino Acid Sequences for
Antibodies A, B, C, and D

| | | |
|---|---|---|
| Antibody A | IgK<br>light<br>Chain #66 | Gacatccagatgacccagagcccaagcagcctgagcg<br>ccagcgtgggcgaccgcgtgaccatcacctgcaaggc<br>cagccgcgacgtggccatcgccgtggcctggtaccag<br>cagaagccaggcaaggtgccaaagctgctgatctact<br>gggccagcacccgccacaccggcgtgccaagccgctt<br>cagcggcagcggcagccgcaccgacttcaccctgacc<br>atcagcagcctgcagccagaggacgtggccgactact<br>actgccaccagtacagcagctaccattcaccttcgg<br>cagcggcaccaagctggagatcaagcgtactgtggct<br>gcaccatctgtcttcatcttcccgccatctgatgagc<br>agttgaaatctggaactgcctctgttgtgtgcctgct<br>gaataacttctatcccagagaggccaaagtacagtgg |

TABLE 7-continued

Heavy and Light Chain DNA and Amino Acid Sequences for Antibodies A, B, C, and D

|  |  |  |
|---|---|---|
|  |  | aaggtggataacgccctccaatcgggtaactcccagg<br>agagtgtcacagagcaggacagcaaggacagcaccta<br>cagcctcagcagcaccctgacgctgagcaaagcagac<br>tacgagaaacacaaagtctacgcctgcgaagtcaccc<br>atcagggcctgagctcgcccgtcacaaagagcttcaa<br>caggggagagtgt (SEQ ID NO: 173)<br>DIQMTQSPSSLSASVGDRVTITCKASRDVAIAVAWYQ<br>QKPGKVPKLLIYWASTRHTGVPSRFSGSGSRTDFTLT<br>ISSLQPEDVADYFCHQYSSYPFTFGSGTKLEIKRTVA<br>APSVFIFPPSDEQLKSGTASVVCLLNNFYPREAKVQW<br>KVDNALQSGNSQESVTEQDSKDSTYSLSSTLTLSKAD<br>YEKHKVYACEVTHQGLSSPVTKSFNRGEC (SEQ ID<br>NO: 174) |
|  | IgG1 KO<br>Heavy<br>Chain #2 | Caggtgcagctggtgcagagcggcgccgaggtgaaga<br>agccaggcagcagcgtgaaggtgagctgcaaggccag<br>cggctacaccttcaccgaccagaccatccactggatg<br>cgccaggccccaggccagggcctggagtggatcggct<br>acatctacccacgcgacgacagcccaaagtacaacga<br>gaacttcaagggcaaggtcaccatcaccgccgacaag<br>agcaccagcaccgcctacatggagctgagcagcctgc<br>gcagcgaggacaccgccgtgtactactgcgccatccc<br>agaccgcagcggctacgcctggttcatctactggggc<br>cagggcaccctggtgaccgtgagcagcgcctccacca<br>agggcccatcggtcttccccctggcaccctcctccaa<br>gagcacctctgggggcacagcggccctgggctgcctg<br>gtcaaggactacttccccgaaccggtgacggtgtcgt<br>ggaactcaggcgccctgaccagcggcgtgcacacctt<br>cccggctgtcctacagtcctcaggactctactccctc<br>agcagcgtggtgaccgtgccctccagcagcttgggca<br>cccagacctacatctgcaacgtgaatcacaagcccag<br>caacaccaaggtcgacaagagagttgagcccaaatct<br>tgtgacaaaactcacacatgcccaccgtgcccagcac<br>cagaagctgctggggaccgtcagtcttcctcttccc<br>cccaaaacccaaggacaccctcatgatctcccggacc<br>cctgaggtcacatgcgtcgtggtggacgtgagccacg<br>aagaccctgaggtcaagttcaactggtacgtggacgg<br>cgtggaggtgcataatgccaagacaaagccgcgggag<br>gagcagtacaacagcacgtaccgtgtggtcagcgtcc<br>tcaccgtcctgcaccaggactggctgaatggcaagga<br>gtacaagtgcaaggtctccaacaaagcccttcccagcc<br>cccatcgagaaaaccatctccaaagccaaagggcagc<br>cccgagaaccacaggtgtacaccctgcccccatcccg<br>ggaggagatgaccaagaaccaggtcagcctgacctgc<br>ctggtcaaaggcttctatcccagcgacatcgccgtgg<br>agtgggagagcaatgggcagccggagaacaactacaa<br>gaccacgcctcccgtgctggactccgacggctccttc<br>ttcctctacagcaagctcaccgtggacaagagcaggt<br>ggcagcaggggaacgtcttctcatgctccgtgatgca<br>tgaggctctgcacaaccactacacgcagaagagcctc<br>tccctgtctccgggt (SEQ ID NO: 175)<br>QVQLVQSGAEVKKPGSSVKVSCKASGYTFTDQTIHWM<br>RQAPGQGLEWIGYIYPRDDSPKYNENFKGKVTITADK<br>STSTAYMELSSLRSEDTAVYYCAIPDRSGYAWFIYWG<br>QGTLVTVSSASTKGPSVFPLAPSSKSTSGGTAALGCL<br>VKDYFPEPVTVSWNSGALTSGVHTFPAVLQSSGLYSL<br>SSVVTVPSSSLGTQTYICNVNHKPSNTKVDKRVEPKS<br>CDKTHTCPPCPAPEAAGGPSVFLFPPKPKDTLMISRT<br>PEVTCVVVDVSHEDPEVKFNWYVDGVEVHNAKTKPRE<br>EQYNSTYRVVSVLTVLHQDWLNGKEYKCKVSNKALPA<br>PIEKTISKAKGQPREPQVYTLPPSREEMTKNQVSLTC<br>LVKGFYPSDIAVEWESNGQPENNYKTTPPVLDSDGSF<br>FLYSKLTVDKSRWQQGNVFSCSVMHEALHNHYTQKSL<br>SLSPG (SEQ ID NO: 176) |
| Antibody B | IgK<br>light<br>Chain #66 | (SEQ ID NO: 173) |
|  | IgG1KO<br>Heavy<br>Chain<br>#5 | (SEQ ID NO: 174)<br>caggtgcagctggtgcagagcggcgccgaggtgaaga<br>agccaggcagcagcgtgaaggtgagctgcaaggccag<br>cggcttcaccttcaccgaccagaccatccactgggtg<br>cgccaggccccaggccagggcctggagtggatgggct<br>acatctacccacgcgacgacagcccaaagtacaacga<br>gaacttcaagggcaaggtcaccctgaccgccgacaag<br>agcaccagcaccgcctacatggagctgagcagcctgc<br>gcagcgaggacaccgccgtgtactactgcgccatccc<br>agaccgcagcggctacgcctggttcatctactggggc |

TABLE 7-continued

Heavy and Light Chain DNA and Amino Acid Sequences for Antibodies A, B, C, and D

| | | |
|---|---|---|
| | | cagggcaccctggtgaccgtgagcagcgcctccacca<br>agggcccatcggtcttccccctggcaccctcctccaa<br>gagcacctctgggggcacagcggccctgggctgcctg<br>gtcaaggactacttccccgaaccggtgacggtgtcgt<br>ggaactcaggcgccctgaccagcggcgtgcacacctt<br>cccggctgtcctacagtcctcaggactctactccctc<br>agcagcgtggtgaccgtgcctccagcagcttgggca<br>cccagacctacatctgcaacgtgaatcacaagcccag<br>caacaccaaggtcgacaagagagttgagcccaaatct<br>tgtgacaaaactcacacatgcccaccgtgcccagcac<br>cagaagctgctggggaccgtcagtcttcctcttccc<br>cccaaaacccaaggacaccctcatgatctcccggacc<br>cctgaggtcacatgcgtcgtggtggacgtgagccacg<br>aagaccctgaggtcaagttcaactggtacgtggacgg<br>cgtggaggtgcataatgccaagacaaagccgcgggag<br>gagcagtacaacagcacgtaccgtgtggtcagcgtcc<br>tcaccgtcctgcaccaggactggctgaatggcaagga<br>gtacaagtgcaaggtctccaacaaagcctcccagcc<br>cccatcgagaaaaccatctccaaagccaaagggcagc<br>cccgagaaccacaggtgtacaccctgcccccatcccg<br>ggaggagatgaccaagaaccaggtcagcctgacctgc<br>ctggtcaaaggcttctatcccagcgacatcgccgtgg<br>agtgggagagcaatgggcagccggagaacaactacaa<br>gaccacgcctcccgtgctggactccgacggctccttc<br>ttcctctacagcaagctcaccgtggacaagagcaggt<br>ggcagcaggggaacgtcttctcatgctccgtgatgca<br>tgaggctctgcacaaccactacacgcagaagagcctc<br>tccctgtctccgggt (SEQ ID NO: 177)<br>QVQLVQSGAEVKKPGSSVKVSCKASGFTFTDQTIHWV<br>RQAPGQGLEWMGYIYPRDDSPKYNENFKGKVTLTADK<br>STSTAYMELSSLRSEDTAVYYCAIPDRSGYAWFIYWG<br>QGTLVTVSSASTKGPSVFPLAPSSKSTSGGTAALGCL<br>VKDYFPEPVTVSWNSGALTSGVHTFPAVLQSSGLYSL<br>SSVVTVPSSSLGTQTYICNVNHKPSNTKVDKRVEPKS<br>CDKTHTCPPCPAPEAAGGPSVFLFPPKPKDTLMISRT<br>PEVTCVVVDVSHEDPEVKFNWYVDGVEVHNAKTKPRE<br>EQYNSTYRVVSVLTVLHQDWLNGKEYKCKVSNKALPA<br>PIEKTISKAKGQPREPQVYTLPPSREEMTKNQVSLTC<br>LVKGFYPSDIAVEWESNGQPENNYKTTPPVLDSDGSF<br>FLYSKLTVDKSRWQQGNVFSCSVMHEALHNHYTQKSL<br>SLSPG (SEQ ID NO: 178) |
| Antibody C | IgK light Chain #65 | Gacatccagatgacccagagcccaagcagcctgagcg<br>ccagcgtgggcgaccgcgtgaccatcacctgcaaggc<br>cagccgcgacgtggccatcgccgtggcctggtaccag<br>cagaagccaggcaaggtgccaaagctgctgctgttct<br>gggccagcacccgccacaccggcgtgccagaccgctt<br>cagcggcagcggcagcggcaccgacttcaccctgacc<br>atcagcagcctgcagccagaggacctggccgactact<br>actgccaccagtacagcagctacccattcaccttcgg<br>ccagggcaccaagctggagatcaagcgtactgtggct<br>gcaccatctgtcttcatcttcccgccatctgatgagc<br>agttgaaatctggaactgcctctgttgtgtgcctgct<br>gaataacttctatcccagagaggccaaagtacagtgg<br>aaggtggataacgccctccaatcgggtaactcccagg<br>agagtgtcacagagcaggacagcaaggacagcaccta<br>cagcctcagcagcaccctgacgctgagcaaagcagac<br>tacgagaaacacaaagtctacgcctgcgaagtcaccc<br>atcagggcctgagctcgcccgtcacaaagagcttcaa<br>caggggagagtgt (SEQ ID NO: 179)<br>DIQMTQSPSSLSASVGDRVTITCKASRDVAIAVAWYQ<br>QKPGKVPKLLLFWASTRHTGVPDRFSGSGSGTDFTLT<br>ISSLQPEDLADYYCHQYSSYPFTFGQGTKLEIKRTVA<br>APSVFIFPPSDEQLKSGTASVVCLLNNFYPREAKVQW<br>KVDNALQSGNSQESVTEQDSKDSTYSLSSTLTLSKAD<br>YEKHKVYACEVTHQGLSSPVTKSFNRGEC (SEQ ID NO: 180) |
| | IgG1KO Heavy Chain #2 | (SEQ ID NO: 175)<br><br>(SEQ ID NO: 176) |

TABLE 7-continued

Heavy and Light Chain DNA and Amino Acid Sequences for Antibodies A, B, C, and D

| Antibody D | IgK light Chain #65 | (SEQ ID NO: 179) |
| | | (SEQ ID NO: 180) |
| | IgG1KO Heavy Chain #5 | (SEQ ID NO: 177) |
| | | (SEQ ID NO: 178) |

Light chains and heavy chain variable regions of Antibodies A, B, C, and D are underlined in Table 7 above.

In one aspect, a humanized anti-IL-23p19 antibody of the present invention has at least one of the properties below. In a further aspect, a humanized anti-IL-23p19 antibody of the present invention has any combination of at least two, or at least 3, 4, 5, 6, 7, 8, 9, 10, or 11 of the properties below. In a further aspect, a humanized anti-IL-23p19 antibody of the present invention has all the properties below.

$K_D$ for human IL-23≤1 pM (no shift in binding on-rate in 50% human serum)
Blocks IL-23 binding to human IL-23R/Fc in vitro
No binding to human IL-12
Inhibits human IL-23 induced IL-17 production in mouse splenocytes with $IC_{50}$'s≤20 pM
Inhibits human IL-23 induced STAT3 phosphorylation in human DB cells with $IC_{50}$'s≤40 pM
No predicted activity in ADCC/CDC
$K_D$≤1 pM for cynomolgus monkey IL-23
No cross reactivity to mouse or rat IL-23
Inhibits human IL-23 induced IL-17 and IL-22 production in mouse ear (≥80% inhibition of both cytokines at 1 mg/kg)
Stability 83° C. (melting temperature 83° C. as determined by differential scanning calorimetry)
Solubility ≥100 mg/ml (as measured by UV spectroscopy and monitored by turbidity)
Subcutaneous administration of 1.0 mg/kg in three cynomolgus monkeys shows sustained ≥10 nM exposure for approximately 28 days with a bioavailability of approximately 70%.

By no predicted activity in ADCC/DC, it is meant herein that a humanized anti-IL-23p19 antibody of the present invention has reduced affinity to Fc receptor and therefore is predicted not to have activity in ADCC/CDC.

In one aspect, a humanized anti-IL-23p19 antibody of the present invention has at least one of the properties below. In a further aspect, a humanized anti-IL-23p19 antibody of the present invention has any combination of at least two, or at least 3, 4, 5, 6, 7, 8, 9, or 10 of the properties below. In a further aspect, a humanized anti-IL-23p19 antibody of the present invention has all the properties below.

$K_D$ for human IL-23≤1 pM (no shift in binding on-rate in 50% human serum)
Blocks IL-23 binding to human IL-23R/Fc in vitro
No binding to human IL-12
Inhibits human IL-23 induced IL-17 production in mouse splenocytes with $IC_{50}$'s≤20 pM
Inhibits human IL-23 induced STAT3 phosphorylation in human DB cells with $IC_{50}$'s≤40 pM
No predicted activity in ADCC/CDC
$K_D$≤1 pM for cynomolgus monkey IL-23
No cross reactivity to mouse or rat IL-23
Inhibits human IL-23 induced IL-17 and IL-22 production in mouse ear (≥80% inhibition of both cytokines at 1 mg/kg)
Stability 83° C. (melting temperature 83° C. as determined by differential scanning calorimetry)
Solubility ≥100 mg/ml (as measured by UV spectroscopy and monitored by turbidity).

In a further aspect, a humanized antibody of the present invention has at least one of the following binding properties (properties A). In a further aspect, a humanized anti-IL-23p19 antibody of the present invention has any combination of at least two, or at least 3, of the properties below. In a further aspect, a humanized anti-IL-23p19 antibody of the present invention has all the properties below.

$K_D$ for human IL-23≤1 pM (no shift in binding on-rate in 50% human serum)
No binding to human IL-12
$K_D$≤1 pM for cynomolgus monkey IL-23
No cross reactivity to mouse or rat IL-23.

In particular, a humanized antibody of the present invention has a $K_D$ for human IL-23≤1 pM (no shift in binding on-rate in 50% human serum) and no binding to human IL-12.

In a further aspect, a humanized antibody of the present invention has at least one of the following functional properties (properties B). In a further aspect, a humanized anti-IL-23p19 antibody of the present invention has any combination of at least two, or at least 3, of the properties below. In a further aspect, a humanized anti-IL-23p19 antibody of the present invention has all the properties below.

Blocks IL-23 binding to human IL-23R/Fc in vitro
Inhibits human IL-23 induced IL-17 production in mouse splenocytes with $IC_{50}$'s≤20 pM
Inhibits human IL-23 induced STAT3 phosphorylation in human DB cells with $IC_{50}$'s≤40 pM
Inhibits human IL-23 induced IL-17 and IL-22 production in mouse ear (≥80% inhibition of both cytokines at 1 mg/kg).

In a further aspect, a humanized antibody of the present invention has at least one of the following properties (properties C). In a further aspect, a humanized anti-IL-23p19 antibody of the present invention has any combination of at least two, or at least 3, of the properties below. In a further aspect, a humanized anti-IL-23p19 antibody of the present invention has all the properties below.

No predicted activity in ADCC/CDC
Stability 83° C. (melting temperature 83° C. as determined by differential scanning calorimetry)
Solubility ≥100 mg/ml (as measured by UV spectroscopy and monitored by turbidity)

Subcutaneous administration of 1.0 mg/kg in three cynomolgus monkeys shows sustained ≥10 nM exposure for approximately 28 days with a bioavailability of approximately 70%.

In a further aspect, a humanized antibody of the present invention has at least one of the following properties (properties C). In a further aspect, a humanized anti-IL-23p19 antibody of the present invention has any combination of at least two of the properties below. In a further aspect, a humanized anti-IL-23p19 antibody of the present invention has all the properties below.

No predicted activity in ADCC/CDC

Stability 83° C. (melting temperature 83° C. as determined by differential scanning calorimetry)

Solubility ≥100 mg/ml (as measured by UV spectroscopy and monitored by turbidity).

In a further aspect, a humanized antibody of the present invention has at least one property A, at least one property B and at least one property C. In a further aspect, a humanized anti-IL-23p19 antibody of the present invention has any combination of at least two, or at least 3, of the properties A, B, and C.

In some aspects, the humanized antibody displays blocking activity, whereby it decreases the binding of IL-23 to IL-23 receptor by at least 45%, by at least 50%, by at least 55%, by at least 60%, by at least 65%, by at least 70%, by at least 75%, by at least 80%, by at least 85%, by at least 90%, or by at least 95%. The ability of an antibody to block binding of IL-23 to the IL-23 receptor can be measured using competitive binding assays known in the art. Alternatively, the blocking activity of an antibody can be measured by assessing the biological effects of IL-23, such as the production of IL-17 and IL-22 to determine if signaling mediated by the IL-23 receptor is inhibited.

In a further aspect, the present invention provides a humanized anti-IL-23p19 antibody having favorable biophysical properties. In one aspect, a humanized anti-IL-23p19 antibody of the present invention is present in at least 90% monomer form, or in at least 92% monomer form, or in at least 95% monomer form in a buffer. In a further aspect, a humanized anti-IL-23p19 antibody of the present invention remains in at least 90% monomer form, or in at least 92% monomer form, or in at least 95% monomer form in a buffer for one month or for four months.

In one aspect, a humanized antibody of the present invention is Antibody A, Antibody B, Antibody C or Antibody D. Accordingly, in one embodiment, a humanized antibody of the present invention comprises the light chain sequence of SEQ ID NO:174 and the heavy chain sequence of SEQ ID NO:176 (Antibody A). In another embodiment, a humanized antibody of the present invention comprises the light chain sequence of SEQ ID NO:174 and the heavy chain sequence of SEQ ID NO:178 (Antibody B). In another embodiment, a humanized antibody of the present invention comprises the light chain sequence of SEQ ID NO:180 and the heavy chain sequence of SEQ ID NO:176 (Antibody C). In another embodiment, a humanized antibody of the present invention comprises the light chain sequence of SEQ ID NO:180 and the heavy chain sequence of SEQ ID NO:178 (Antibody D).

In a further embodiment, a humanized antibody of the present invention consists of the light chain sequence of SEQ ID NO:174 and the heavy chain sequence of SEQ ID NO:176 (Antibody A). In a further embodiment, a humanized antibody of the present invention consists of the light chain sequence of SEQ ID NO:174 and the heavy chain sequence of SEQ ID NO:178 (Antibody B). In a further embodiment, a humanized antibody of the present invention consists of the light chain sequence of SEQ ID NO:180 and the heavy chain sequence of SEQ ID NO:176 (Antibody C). In a further embodiment, a humanized antibody of the present invention consists of the light chain sequence of SEQ ID NO:180 and the heavy chain sequence of SEQ ID NO:178 (Antibody D).

In some embodiments, the humanized anti-IL-23p19 antibodies, including antigen-binding fragments thereof, such as heavy and light chain variable regions, comprise an amino acid sequence of the residues derived from Antibody A (light chain sequence=SEQ ID NO:174; heavy chain sequence=SEQ ID NO:176), Antibody B (light chain sequence=SEQ ID NO:174; heavy chain sequence=SEQ ID NO:178), Antibody C (light chain sequence=SEQ ID NO:180; heavy chain sequence=SEQ ID NO:176) or Antibody D (light chain sequence=SEQ ID NO:180; heavy chain sequence=SEQ ID NO:178).

In a further embodiment, the present invention provides an anti-IL-23p19 antibody or an antigen-binding fragment thereof that binds to human IL-23p19 at an epitope consisting of amino acid residues 108 to 126 and amino acid residues 137 to 151 of SEQ ID NO: 181.

In a further embodiment, the present invention provides an anti-IL-23p19 antibody or antigen-binding fragment thereof that competitively binds to human IL-23p19 with an antibody of the present invention, for example Antibody A, Antibody B, Antibody C or Antibody D described herein. The ability of an antibody or antigen-binding fragment to competitively bind to IL-23p19 can be measured using competitive binding assays known in the art.

The humanized anti-IL-23p19 antibodies optionally include specific amino acid substitutions in the consensus or germline framework regions. The specific substitution of amino acid residues in these framework positions can improve various aspects of antibody performance including binding affinity and/or stability, over that demonstrated in humanized antibodies formed by "direct swap" of CDRs or HVLs into the human germline framework regions.

In some embodiments, the present invention describes other monoclonal antibodies with a light chain variable region having the amino acid sequence set forth in of SEQ ID NO: 84, 86, 88, 90, 91, 93, 95, 97, 99, 101, 103, 105, 107, 109, 111, 113, 115, 117 or 119. In some embodiments, the present invention describes other monoclonal antibodies with a heavy chain variable region having the amino acid sequence set forth in of SEQ ID NO: 121, 123, 125, 127, 128, 130, 132, 134, 136, 138, 140, 142, 144, 146, 148, 150, 152, 154 or 156 (see Tables 1 and 2 above). The CDR sequence of these mouse antibodies are shown in Tables 3 and 4. Placing such CDRs into FRs of the human consensus heavy and light chain variable domains will yield useful humanized antibodies of the present invention.

In particular, the present invention provides monoclonal antibodies with the combinations of light chain variable and heavy chain variable regions of SEQ ID NO:84/121, 86/123, 88/125, 90/127, 91/128, 93/130, 95/132, 97/134, 99/136, 101/138, 103/140, 105/142, 107/144, 109/146, 111/148, 113/150, 115/152, 117/154 or 119/156. Such variable regions can be combined with human constant regions.

In some embodiments, the present invention describes other humanized antibodies with light chain variable region sequences having the amino acid sequence set forth in of SEQ ID NO:158, 160, 162 or 164. In some embodiments, the present invention describes other humanized antibodies with heavy chain variable region sequences having the amino acid sequence set forth in of SEQ ID NO:166, 168, 170 or 172 (see Tables 5 and 6 above). The CDR sequences of these antibodies are shown in Tables 3 and 4. In particular, the present invention provides monoclonal antibodies with the combinations of light chain variable and heavy chain variable regions of SEQ ID NO: 160/166, 160/168, 158/166 or 158/168. Such variable regions can be combined with human constant regions.

In a further embodiment, the present invention relates to an anti-IL-23p19 antibody or antigen-binding fragment thereof comprising a humanized light chain variable domain comprising the CDRs of SEQ ID NO:160 and framework regions having an amino acid sequence at least 90% identical, at least 93% identical or at least 95% identical to the amino acid sequence of the framework regions of the variable domain light chain amino acid sequence of SEQ ID NO:160 and a humanized heavy chain variable domain comprising the CDRs of SEQ ID NO:166 and framework regions having an amino acid sequence at least 90% identical, at least 93% identical or at least 95% identical to the amino acid sequence of the framework regions of the variable domain heavy chain amino acid sequence of SEQ ID NO:166. In one embodiment, the anti-IL-23p19 antibody is a humanized monoclonal antibody.

In a further embodiment, the present invention relates to an anti-IL-23p19 antibody or antigen-binding fragment thereof comprising a humanized light chain variable domain comprising the CDRs of SEQ ID NO:160 and framework regions having an amino acid sequence at least 90% identical, at least 93% identical or at least 95% identical to the amino acid sequence of the framework regions of the variable domain light chain amino acid sequence of SEQ ID NO:160 and a humanized heavy chain variable domain comprising the CDRs of SEQ ID NO:168 and framework regions having an amino acid sequence at least 90% identical, at least 93% identical or at least 95% identical to the amino acid sequence of the framework regions of the variable domain heavy chain amino acid sequence of SEQ ID NO:168. In one embodiment, the anti-IL-23p19 antibody is a humanized monoclonal antibody.

In a further embodiment, the present invention relates to an anti-IL-23p19 antibody or antigen-binding fragment thereof comprising a humanized light chain variable domain comprising the CDRs of SEQ ID NO:158 and framework regions having an amino acid sequence at least 90% identical, at least 93% identical or at least 95% identical to the amino acid sequence of the framework regions of the variable domain light chain amino acid sequence of SEQ ID NO:158 and a humanized heavy chain variable domain comprising the CDRs of SEQ ID NO:166 and framework regions having an amino acid sequence at least 90% identical, at least 93% identical or at least 95% identical to the amino acid sequence of the framework regions of the variable domain heavy chain amino acid sequence of SEQ ID NO:166. In one embodiment, the anti-IL-23p19 antibody is a humanized monoclonal antibody.

In a further embodiment, the present invention relates to an anti-IL-23p19 antibody or antigen-binding fragment thereof comprising a humanized light chain variable domain comprising the CDRs of SEQ ID NO:158 and framework regions having an amino acid sequence at least 90% identical, at least 93% identical or at least 95% identical to the amino acid sequence of the framework regions of the variable domain light chain amino acid sequence of SEQ ID NO:158 and a humanized heavy chain variable domain comprising the CDRs of SEQ ID NO:168 and framework regions having an amino acid sequence at least 90% identical, at least 93% identical or at least 95% identical to the amino acid sequence of the framework regions of the variable domain heavy chain amino acid sequence of SEQ ID NO:168. In one embodiment, the anti-IL-23p19 antibody is a humanized monoclonal antibody.

In some specific embodiments, the humanized anti-IL-23p19 antibodies disclosed herein comprise at least a heavy or a light chain variable domain comprising the CDRs or HVLs of the murine monoclonal antibodies or humanized antibodies as shown in Tables 1 through 6 above and the FRs of the human germline heavy and light chain variable domains.

The CDRs of these sequences are shown in Tables 3 and 4. Accordingly, in one aspect, the present invention provides an anti-IL-23p19 antibody or antigen-binding fragment thereof comprising a light chain CDR1 (L-CDR1) sequence of SEQ ID NO:1, 4, 6, 7, 8, 11, 15, 18, 19, 22, 27 or 30; a light chain CDR2 (L-CDR2) sequence of SEQ ID NO:2, 5, 9, 12, 16, 20, 23, 25, 28 or 31; a light chain CDR3 (L-CDR3) sequence of SEQ ID NO:3, 10, 13, 14, 17, 21, 24, 26, 29, or 32; a heavy chain CDR1 (H-CDR1) sequence of SEQ ID NO:33, 36, 38, 40, 43, 45, 48, 51, 54, 57, 60, 63, 66, 67, 68, 69, 77 or 80; a heavy chain CDR2 (H-CDR2) sequence of SEQ ID NO:34, 39, 41, 46, 49, 52, 55, 58, 61, 64, 70, 72, 73, 75, 78 or 81; and a heavy chain CDR3 (H-CDR3) sequence of SEQ ID NO:35, 37, 42, 44, 47, 50, 53, 56, 59, 62, 65, 71, 74, 76, 79 or 82. In one aspect, the anti-IL-23p19 antibody or antigen-binding fragment thereof comprises a light chain variable region comprising a L-CDR1 listed above, a L-CDR2 listed above and a L-CDR3 listed above, and a heavy chain variable region comprising a H-CDR1 listed above, a H-CDR2 listed above and a H-CDR3 listed above.

In a further aspect, the present invention provides an anti-IL-23p19 antibody or antigen-binding fragment thereof comprising:

a) a L-CDR1, a L-CDR2, a L-CDR3, a H-CDR1, a H-CDR2 and a H-CDR3 sequence of SEQ ID NO:1, 2, 3, 33, 34, and 35, respectively; or
b) a L-CDR1, a L-CDR2, a L-CDR3, a H-CDR1, a H-CDR2 and a H-CDR3 sequence of SEQ ID NO:4, 5, 3, 36, 34 and 37, respectively; or
c) a L-CDR1, a L-CDR2, a L-CDR3, a H-CDR1, a H-CDR2 and a H-CDR3 sequence of SEQ ID NO:1, 2, 3, 38, 39 and 35, respectively; or
d) a L-CDR1, a L-CDR2, a L-CDR3, a H-CDR1, a H-CDR2 and a H-CDR3 sequence of SEQ ID NO:6, 2, 3, 40, 41 and 42, respectively; or
e) a L-CDR1, a L-CDR2, a L-CDR3, a H-CDR1, a H-CDR2 and a H-CDR3 sequence of SEQ ID NO:7, 2, 3, 43, 41 and 44, respectively; or
f) a L-CDR1, a L-CDR2, a L-CDR3, a H-CDR1, a H-CDR2 and a H-CDR3 sequence of SEQ ID NO:8, 9, 10, 45, 46 and 47, respectively; or
g) a L-CDR1, a L-CDR2, a L-CDR3, a H-CDR1, a H-CDR2 and a H-CDR3 sequence of SEQ ID NO:8, 9, 10, 48, 49 and 50, respectively; or
h) a L-CDR1, a L-CDR2, a L-CDR3, a H-CDR1, a H-CDR2 and a H-CDR3 sequence of SEQ ID NO:11, 12, 13, 51, 52 and 53, respectively; or
i) a L-CDR1, a L-CDR2, a L-CDR3, a H-CDR1, a H-CDR2 and a H-CDR3 sequence of SEQ ID NO:7, 2, 14, 54, 55 and 56, respectively; or
j) a L-CDR1, a L-CDR2, a L-CDR3, a H-CDR1, a H-CDR2 and a H-CDR3 sequence of SEQ ID NO:15, 16, 17, 57, 58 and 59, respectively; or
k) a L-CDR1, a L-CDR2, a L-CDR3, a H-CDR1, a H-CDR2 and a H-CDR3 sequence of SEQ ID NO:18, 16, 17, 60, 61 and 62, respectively; or l) a L-CDR1, a L-CDR2, a L-CDR3, a H-CDR1, a H-CDR2 and a H-CDR3 sequence of SEQ ID NO:19, 20, 21, 63, 66, 67 or 68, 64 and 65, respectively; or m) a L-CDR1, a L-CDR2, a L-CDR3, a H-CDR1, a H-CDR2 and a H-CDR3 sequence of SEQ ID NO:22, 23, 24, 69, 70 and 71, respectively; or n) a L-CDR1, a L-CDR2, a L-CDR3, a H-CDR1, a H-CDR2 and a H-CDR3 sequence of SEQ ID NO:22, 25, 26, 55, 72 and 71, respectively; or o) a L-CDR1, a L-CDR2, a L-CDR3, a H-CDR1, a H-CDR2 and a H-CDR3 sequence of SEQ ID NO:8, 9, 10, 45, 73 and 74, respectively; or p) a L-CDR1, a L-CDR2, a L-CDR3, a H-CDR1, a H-CDR2 and a H-CDR3 sequence of SEQ ID NO:27, 28, 29, 45, 75 and 76, respectively; or q) a L-CDR1, a L-CDR2, a L-CDR3, a H-CDR1, a H-CDR2 and a H-CDR3 sequence of SEQ ID NO:8, 9, 10, 77, 78 and 79, respectively; or r) a L-CDR1, a L-CDR2, a L-CDR3, a H-CDR1, a H-CDR2 and a H-CDR3 sequence of SEQ ID NO:30, 31, 32, 80, 81 and 82, respectively.

In one aspect, the anti-IL-23p19 antibody or antigen-binding fragment thereof comprises a light chain variable region comprising a L-CDR1, L-CDR2 and L-CDR3 combination listed above, and a heavy chain variable region comprising a H-CDR1, H-CDR2 and H-CDR3 combination listed above.

In specific embodiments, it is contemplated that chimeric antibodies with switched CDR regions (i.e., for example switching one or two CDRs of one of the mouse antibodies or humanized antibody derived therefrom with the analogous CDR from another mouse antibody or humanized antibody derived therefrom) between these exemplary immunoglobulins may yield useful antibodies.

In certain embodiments, the humanized anti-IL-23p19 antibody is an antibody fragment. Various antibody fragments have been generally discussed above and there are techniques that have been developed for the production of antibody fragments. Fragments can be derived via proteolytic digestion of intact antibodies (see, e.g., Morimoto et al., 1992, Journal of Biochemical and Biophysical Methods 24:107-117; and Brennan et al., 1985, Science 229:81). Alternatively, the fragments can be produced directly in recombinant host cells. For example, Fab'-SH fragments can be directly recovered from E. coli and chemically coupled to form F(ab')$_2$ fragments (see, e.g., Carter et al., 1992, Bio/Technology 10:163-167). By another approach, F(ab')$_2$ fragments can be isolated directly from recombinant host cell culture. Other techniques for the production of antibody fragments will be apparent to the skilled practitioner. Accordingly, in one aspect, the present invention provides antibody fragments comprising the CDRs described herein, in particular one of the combinations of L-CDR1, L-CDR2, L-CDR3, H-CDR1, H-CDR2 and H-CDR3 described herein. In a further aspect, the present invention provides antibody fragments comprising the variable regions described herein, for example one of the combinations of light chain variable regions and heavy chain variable regions described herein.

Certain embodiments include an F(ab')$_2$ fragment of a humanized anti-IL-23p19 antibody comprise a light chain sequence of any of SEQ ID NO: 174 or 180 in combination with a heavy chain sequence of SEQ ID NO: 176 or 178. Such embodiments can include an intact antibody comprising such an F(ab')$_2$.

In some embodiments, the antibody or antibody fragment includes a constant region that mediates effector function. The constant region can provide antibody-dependent cellular cytotoxicity (ADCC), antibody-dependent cellular phagocytosis (ADCP) and/or complement-dependent cytotoxicity (CDC) responses against an IL-23 expressing target cell. The effector domain(s) can be, for example, an Fc region of an Ig molecule.

The effector domain of an antibody can be from any suitable vertebrate animal species and isotypes. The isotypes from different animal species differ in the abilities to mediate effector functions. For example, the ability of human immunoglobulin to mediate CDC and ADCC/ADCP is generally in the order of IgM≈IgG$_1$≈IgG$_3$>IgG$_2$>IgG$_4$ and IgG$_1$≈IgG$_3$>IgG$_2$/IgM/IgG$_4$, respectively. Murine immunoglobulins mediate CDC and ADCC/ADCP generally in the order of murine IgM≈IgG$_3$>>IgG$_{2b}$>IgG$_{2a}$>>IgG$_1$ and IgG$_{2b}$>IgG$_{2a}$>IgG$_1$>>IgG$_3$, respectively. In another example, murine IgG$_{2a}$ mediates ADCC while both murine IgG$_{2a}$ and IgM mediate CDC.

Antibody Modifications

The humanized anti-IL-23p19 antibodies and agents can include modifications of the humanized anti-IL-23p19 antibody or antigen-binding fragment thereof. For example, it may be desirable to modify the antibody with respect to effector function, so as to enhance the effectiveness of the antibody in treating cancer. One such modification is the introduction of cysteine residue(s) into the Fc region, thereby allowing interchain disulfide bond formation in this region. The homodimeric antibody thus generated can have improved internalization capability and/or increased complement-mediated cell killing and/or antibody-dependent cellular cytotoxicity (ADCC). See, for example, Caron et al., 1992, J. Exp Med. 176:1191-1195; and Shopes, 1992, J. Immunol. 148:2918-2922. Homodimeric antibodies having enhanced anti-tumor activity can also be prepared using heterobifunctional cross-linkers as described in Wolff et al., 1993, Cancer Research 53: 2560-2565. Alternatively, an antibody can be engineered to contain dual Fc regions, enhancing complement lysis and ADCC capabilities of the antibody. See Stevenson et al., 1989, Anti-Cancer Drug Design 3: 219-230.

Antibodies with improved ability to support ADCC have been generated by modifying the glycosylation pattern of their Fc region. This is possible since antibody glycosylation at the asparagine residue, N297, in the $C_{H2}$ domain is involved in the interaction between IgG and Fcγ receptors prerequisite to ADCC. Host cell lines have been engineered to express antibodies with altered glycosylation, such as increased bisecting N-acetylglucosamine or reduced fucose. Fucose reduction provides greater enhancement to ADCC activity than does increasing the presence of bisecting N-acetylglucosamine. Moreover, enhancement of ADCC by low fucose antibodies is independent of the FcγRIIIa V/F polymorphism.

Modifying the amino acid sequence of the Fc region of antibodies is an alternative to glycosylation engineering to enhance ADCC. The binding site on human IgG$_1$ for Fcγ receptors has been determined by extensive mutational analysis. This led to the generation of humanized IgG$_1$ antibodies with Fc mutations that increase the binding affinity for FcγRIIIa and enhance ADCC in vitro. Additionally, Fc variants have been obtained with many different permutations of binding properties, e.g., improved binding to specific FcγR receptors with unchanged or diminished binding to other FcγR receptors.

Another aspect includes immunoconjugates comprising the humanized antibody or fragments thereof conjugated to a cytotoxic agent such as a chemotherapeutic agent, a toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used to form useful immunoconjugates include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolacca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, the tricothecenes, and the like. A variety of radionuclides are available for the production of radioconjugated humanized anti-IL-23p19 antibodies. Examples include $^{212}$Bi, $^{131}$I, $^{131}$In, $^{90}$Y, and $^{186}$Re.

Conjugates of the humanized anti-IL-23p19 antibody and cytotoxic or chemotherapeutic agent can be made by known methods, using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., 1987, Science 238:1098. Carbon-14-labeled 1-isothiocyanatobenzyl-3-methyldiethylene triaminepentaacetic acid (MX-DTPA) is an exemplary chelating agent for conjugation of radionucleotide to the antibody. Conjugates also can be formed with a cleavable linker.

The humanized anti-IL-23p19 antibodies disclosed herein can also be formulated as immunoliposomes. Liposomes containing the antibody are prepared by methods known in the art, such as described in Epstein et al., 1985, Proc. Natl. Acad. Sci. USA 82:3688; Hwang et al., 1980, Proc. Natl. Acad. Sci. USA 77:4030; and U.S. Pat. Nos. 4,485,045 and 4,544,545. Liposomes having enhanced circulation time are disclosed, for example, in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of an antibody disclosed herein can be conjugated to the liposomes as described in Martin et al., 1982, J. Biol. Chem. 257:286-288 via a disulfide interchange reaction. A chemotherapeutic agent (such as doxorubicin) is optionally contained within the liposome. See, e.g., Gabizon et al., 1989, J. National Cancer Inst. 81(19):1484.

The antibodies described and disclosed herein can also be used in ADEPT (Antibody-Directed Enzyme Prodrug Therapy) procedures by conjugating the antibody to a prodrug-activating enzyme that converts a prodrug (e.g., a peptidyl chemotherapeutic agent), to an active anti-cancer drug. See, for example, WO 81/01145, WO 88/07378, and U.S. Pat. No. 4,975,278. The enzyme component of the immunoconjugate useful for ADEPT is an enzyme capable of acting on a prodrug in such a way so as to covert it into its more active, cytotoxic form. Specific enzymes that are useful in ADEPT include, but are not limited to, alkaline phosphatase for converting phosphate-containing prodrugs into free drugs; arylsulfatase for converting sulfate-containing prodrugs into free drugs; cytosine deaminase for converting non-toxic 5-fluorocytosine into the anti-cancer drug, 5-fluorouracil; proteases, such as serratia protease, thermolysin, subtilisin, carboxypeptidases, and cathepsins (such as cathepsins B and L), for converting peptide-containing prodrugs into free drugs; D-alanylcarboxypeptidases, for converting prodrugs containing D-amino acid substituents; carbohydrate-cleaving enzymes such as β-galactosidase and neuraminidase for converting glycosylated prodrugs into free drugs; β-lactamase for converting drugs derivatized with β-lactams into free drugs; and penicillin amidases, such as penicillin V amidase or penicillin G amidase, for converting drugs derivatized at their amine nitrogens with phenoxyacetyl or phenylacetyl groups, respectively, into free drugs. Alternatively, antibodies having enzymatic activity ("abzymes") can be used to convert the prodrugs into free active drugs (see, for example, Massey, 1987, Nature 328: 457-458). Antibody-abzyme conjugates can be prepared by known methods for delivery of the abzyme to a tumor cell population, for example, by covalently binding the enzyme to the humanized anti-IL-23p19 antibody/heterobifunctional crosslinking reagents discussed above. Alternatively, fusion proteins comprising at least the antigen binding region of an antibody disclosed herein linked to at least a functionally active portion of an enzyme as described above can be constructed using recombinant DNA techniques (see, e.g., Neuberger et al., 1984, Nature 312:604-608).

In certain embodiments, it may be desirable to use a humanized anti-IL-23p19 antibody fragment, rather than an intact antibody, to increase tissue penetration, for example. It may be desirable to modify the antibody fragment in order to increase its serum half life. This can be achieved, for example, by incorporation of a salvage receptor binding epitope into the antibody fragment. In one method, the appropriate region of the antibody fragment can be altered (e.g., mutated), or the epitope can be incorporated into a peptide tag that is then fused to the antibody fragment at either end or in the middle, for example, by DNA or peptide synthesis. See, e.g., WO 96/32478.

In other embodiments, covalent modifications of the humanized anti-IL-23p19 antibody are also included. Covalent modifications include modification of cysteinyl residues, histidyl residues, lysinyl and amino-terminal residues, arginyl residues, tyrosyl residues, carboxyl side groups (aspartyl or glutamyl), glutaminyl and asparaginyl residues, or seryl, or threonyl residues. Another type of covalent modification involves chemically or enzymatically coupling glycosides to the antibody. Such modifications may be made by chemical synthesis or by enzymatic or chemical cleavage of the antibody, if applicable. Other types of covalent modifications of the antibody can be introduced into the molecule by reacting targeted amino acid residues of the antibody with an organic derivatizing agent that is capable of reacting with selected side chains or the amino- or carboxy-terminal residues.

Removal of any carbohydrate moieties present on the antibody can be accomplished chemically or enzymatically. Chemical deglycosylation is described by Hakimuddin et al., 1987, Arch. Biochem. Biophys. 259:52 and by Edge et al., 1981, Anal. Biochem., 118:131. Enzymatic cleavage of carbohydrate moieties on antibodies can be achieved by the use of a variety of endo- and exo-glycosidases as described by Thotakura et al., 1987, Meth. Enzymol 138:350.

Another type of useful covalent modification comprises linking the antibody to one of a variety of nonproteinaceous polymers, e.g., polyethylene glycol, polypropylene glycol, or polyoxyalkylenes, in the manner set forth in one or more of U.S. Pat. No. 4,640,835, U.S. Pat. No. 4,496,689, U.S. Pat. No. 4,301,144, U.S. Pat. No. 4,670,417, U.S. Pat. No. 4,791,192 and U.S. Pat. No. 4,179,337.

Humanization and Amino Acid Sequence Variants

Amino acid sequence variants of the anti-IL-23p19 antibody can be prepared by introducing appropriate nucleotide changes into the anti-IL-23p19 antibody DNA, or by peptide synthesis. Such variants include, for example, deletions from, and/or insertions into and/or substitutions of, residues within the amino acid sequences of the anti-IL-23p19 antibodies of the examples herein. Any combination of deletions, insertions, and substitutions is made to arrive at the final construct, provided that the final construct possesses the desired characteristics. The amino acid changes also may alter post-translational processes of the humanized or variant anti-IL-23p19 antibody, such as changing the number or position of glycosylation sites.

A useful method for identification of certain residues or regions of the anti-IL-23p19 antibody that are preferred locations for mutagenesis is called "alanine scanning mutagenesis," as described by Cunningham and Wells (Science, 244:1081-1085 (1989)). Here, a residue or group of target residues are identified (e.g., charged residues such as arg, asp, his, lys, and glu) and replaced by a neutral or negatively charged amino acid (typically alanine) to affect the interaction of the amino acids with IL-23p19 antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, alanine scanning or random mutagenesis is conducted at the target codon or region and the expressed anti-IL-23p19 antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an anti-IL-23p19 antibody fused to an epitope tag. Other insertional variants of the anti-IL-23p19 antibody molecule include a fusion to the N- or C-terminus of the anti-IL-23p19 antibody of an enzyme or a polypeptide which increases the serum half-life of the antibody.

Another type of variant is an amino acid substitution variant. These variants have at least one amino acid residue in the anti-IL-23p19 antibody molecule removed and a different residue inserted in its place. The sites of greatest interest for substitutional mutagenesis include the hypervariable regions, but FR alterations are also contemplated. Conservative substitutions are shown in Table 5 under the heading of "preferred substitutions". If such substitutions result in a change in biological activity, then more substantial changes, denominated "exemplary substitutions", or as further described below in reference to amino acid classes, may be introduced and the products screened.

TABLE 8

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | arg; asn; gln; lys; | arg |
| Ile (I) | leu; val; met; ala; phe; norleucine | leu |
| Leu (L) | ile; norleucine; val; met; ala; phe | ile |
| Lys (K) | arg; gln; asn | arg |
| Met (M) | leu; phe; ile | leu |
| Phe (F) | tyr; leu; val; ile; ala; | tyr |
| Pro (P) | ala | ala |
| Ser (S) | thr | thr |
| Thr (T) | ser | ser |
| Trp (W) | tyr; phe | tyr |
| Tyr (Y) | phe; trp; thr; ser | phe |
| Val (V) | leu; ile; met; phe ala; norleucine; | leu |

In protein chemistry, it is generally accepted that the biological properties of the antibody can be accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class.

Any cysteine residue not involved in maintaining the proper conformation of the humanized or variant anti-IL-23p19 antibody also may be substituted, generally with serine, to improve the oxidative stability of the molecule, prevent aberrant crosslinking, or provide for established points of conjugation to a cytotoxic or cytostatic compound. Conversely, cysteine bond(s) may be added to the antibody to improve its stability (particularly where the antibody is an antibody fragment such as an Fv fragment).

A type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants is affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity). In order to identify candidate hypervariable region sites for modification, alanine scanning mutagenesis can be performed to identify hypervariable region residues contributing significantly to antigen binding. Alternatively, or in addition, it may be beneficial to analyze a crystal structure of the antigen-antibody complex to identify contact points between the antibody and human IL-23p19. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By "altering" is meant deleting one or more carbohydrate moieties found in the antibody, and/or adding one or more glycosylation sites that are not present in the antibody.

In some embodiments, it may be desirable to modify the antibodies of the invention to add glycosylations sites. Glycosylation of antibodies is typically either N-linked or 0-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Thus, in order to glycosylate a given protein, e.g., an antibody, the amino acid sequence of the protein is engineered to contain one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the anti-IL-23p19 antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-IL-23p19 antibody.

Polynucleotides, Vectors, Host Cells, and Recombinant Methods

Other embodiments encompass isolated polynucleotides that comprise a sequence encoding a humanized anti-IL-23p19 antibody, vectors, and host cells comprising the polynucleotides, and recombinant techniques for production of the humanized antibody. The isolated polynucleotides can encode any desired form of the anti-IL-23p19 antibody including, for example, full length monoclonal antibodies, Fab, Fab', F(ab')₂, and Fv fragments, diabodies, linear antibodies, single-chain antibody molecules, and multispecific antibodies formed from antibody fragments.

Some embodiments include isolated polynucleotides comprising sequences that encode the light chain variable region of an antibody or antibody fragment having the amino acid sequence of any of SEQ ID NO: SEQ ID NO:84, 86, 88, 90, 91, 93, 95, 97, 99, 101, 103, 105, 107, 109, 111, 113, 115, 117 or 119. Exemplary polynucleotide sequences encoding such amino acid sequences are SEQ ID NO:83, 85, 87, 89, 92, 94, 96, 98, 100, 102, 104, 106, 108, 110, 112, 114, 116 and 118. Some embodiments include isolated polynucleotides comprising sequences that encode the heavy chain variable region of an antibody or antibody fragment having the amino acid sequence of SEQ ID NO:121, 123, 125, 127, 128, 130, 132, 134, 136, 138, 140, 142, 144, 146, 148, 150, 152, 154 or 156. Exemplary polynucleotide sequences encoding such amino acid sequences are SEQ ID NO: 120, 122, 124, 126, 129, 131, 133, 135, 137, 139, 141, 143, 145, 147, 149, 151, 153 or 155.

Some embodiments include isolated polynucleotides comprising sequences that encode the light chain variable region of an antibody or antibody fragment having the amino acid sequence of any of SEQ ID NO:158, 160, 162 or 164. Exemplary polynucleotide sequences encoding such amino acid sequences are SEQ ID NO:157, 159, 161 or 163. Some embodiments include isolated polynucleotides comprising sequences that encode the heavy chain variable region of an antibody or antibody fragment having the amino acid sequence of SEQ ID NO: 166, 168, 170 or 172. Exemplary polynucleotide sequences encoding such amino acid sequences are SEQ ID NO: 165, 167, 169 or 171.

Some embodiments include isolated polynucleotides comprising sequences that encode the light chain of an antibody having the amino acid sequence of any of SEQ ID NO:174 or 180. Exemplary polynucleotide sequences encoding such amino acid sequences are SEQ ID NO:173 or 179. Some embodiments include isolated polynucleotides comprising sequences that encode the heavy chain of an antibody having the amino acid sequence of SEQ ID NO:176 or 178. Exemplary polynucleotide sequences encoding such amino acid sequences are SEQ ID NO:175 or 177.

In one aspect, the isolated polynucleotide sequence(s) encodes an antibody or antibody fragment having a light chain and a heavy chain variable region comprising the amino acid sequences of SEQ ID NO:174 and SEQ ID NO:176, respectively; SEQ ID NO:174 and SEQ ID NO:178, respectively; SEQ ID NO:180 and SEQ ID NO:176, respectively; SEQ ID NO:180 and SEQ ID NO:178, respectively. Exemplary polynucleotide sequences encoding such amino acid sequences are SEQ ID NO: 173 and 175, respectively, SEQ ID NO: 173 and 177, respectively, SEQ ID NO: 179 and 175, respectively, SEQ ID NO: 179 and 177, respectively.

The polynucleotide(s) that comprise a sequence encoding a humanized anti-IL-23p19 antibody or a fragment or chain thereof can be fused to one or more regulatory or control sequence, as known in the art, and can be contained in suitable expression vectors or host cell as known in the art. Each of the polynucleotide molecules encoding the heavy or light chain variable domains can be independently fused to a polynucleotide sequence encoding a constant domain, such as a human constant domain, enabling the production of intact antibodies. Alternatively, polynucleotides, or portions thereof, can be fused together, providing a template for production of a single chain antibody.

For recombinant production, a polynucleotide encoding the antibody is inserted into a replicable vector for cloning (amplification of the DNA) or for expression. Many suitable vectors for expressing the recombinant antibody are available. The vector components generally include, but are not limited to, one or more of the following: a signal sequence, an origin of replication, one or more marker genes, an enhancer element, a promoter, and a transcription termination sequence.

The humanized anti-IL-23p19 antibodies can also be produced as fusion polypeptides, in which the antibody is fused with a heterologous polypeptide, such as a signal sequence or other polypeptide having a specific cleavage site at the amino terminus of the mature protein or polypeptide. The heterologous signal sequence selected is typically one that is recognized and processed (i.e., cleaved by a signal peptidase) by the host cell. For prokaryotic host cells that do not recognize and process the humanized anti-IL-23p19 antibody signal sequence, the signal sequence can be substituted by a prokaryotic signal sequence. The signal sequence can be, for example, alkaline phosphatase, penicillinase, lipoprotein, heat-stable enterotoxin II leaders, and the like. For yeast secretion, the native signal sequence can be substituted, for example, with a leader sequence obtained from yeast invertase alpha-factor (including *Saccharomyces* and *Kluyveromyces* α-factor leaders), acid phosphatase, *C. albicans* glucoamylase, or the signal described in WO90/13646. In mammalian cells, mammalian signal sequences as well as viral secretory leaders, for example, the herpes simplex gD signal, can be used. The DNA for such precursor region is ligated in reading frame to DNA encoding the humanized anti-IL-23p19 antibody.

Expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2-v. plasmid origin is suitable for yeast, and various viral origins (SV40, polyoma, adenovirus, VSV, and BPV) are useful for cloning vectors in mammalian cells.

Generally, the origin of replication component is not needed for mammalian expression vectors (the SV40 origin may typically be used only because it contains the early promoter).

Expression and cloning vectors may contain a gene that encodes a selectable marker to facilitate identification of expression. Typical selectable marker genes encode proteins that confer resistance to antibiotics or other toxins, e.g., ampicillin, neomycin, methotrexate, or tetracycline, or alternatively, are complement auxotrophic deficiencies, or in other alternatives supply specific nutrients that are not present in complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid, and hygromycin. Common selectable markers for mammalian cells are those that enable the identification of cells competent to take up a nucleic acid encoding a humanized anti-IL-23p19 antibody, such as DHFR (dihydrofolate reductase), thymidine kinase, metallothionein-I and -II (such as primate metallothionein genes), adenosine deaminase, ornithine decarboxylase, and the like. Cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., DG44).

Alternatively, host cells (particularly wild-type hosts that contain endogenous DHFR) transformed or co-transformed with DNA sequences encoding anti-IL-23p19 antibody, wild-type DHFR protein, and another selectable marker such as aminoglycoside 3'-phosphotransferase (APH), can be selected by cell growth in medium containing a selection agent for the selectable marker such as an aminoglycosidic antibiotic, e.g., kanamycin, neomycin, or G418. See, e.g., U.S. Pat. No. 4,965,199.

Where the recombinant production is performed in a yeast cell as a host cell, the TRP1 gene present in the yeast plasmid YRp7 (Stinchcomb et al., 1979, Nature 282: 39) can be used as a selectable marker. The TRP1 gene provides a selection marker for a mutant strain of yeast lacking the ability to grow in tryptophan, for example, ATCC No. 44076 or PEP4-1 (Jones, 1977, Genetics 85:12). The presence of the trp1 lesion in the yeast host cell genome then provides an effective environment for detecting transformation by growth in the absence of tryptophan. Similarly, Leu2p-deficient yeast strains such as ATCC 20,622 and 38,626 are complemented by known plasmids bearing the LEU2 gene.

In addition, vectors derived from the 1.6 μm circular plasmid pKD1 can be used for transformation of *Kluyveromyces* yeasts. Alternatively, an expression system for large-scale production of recombinant calf chymosin was reported for *K. lactis* (Van den Berg, 1990, Bio/Technology 8:135). Stable multi-copy expression vectors for secretion of mature recombinant human serum albumin by industrial strains of *Kluyveromyces* have also been disclosed (Fleer et al., 1991, Bio/Technology 9:968-975).

Expression and cloning vectors usually contain a promoter that is recognized by the host organism and is operably linked to the nucleic acid molecule encoding an anti-IL-23p19 antibody or polypeptide chain thereof. Promoters suitable for use with prokaryotic hosts include phoA promoter, β-lactamase and lactose promoter systems, alkaline phosphatase, tryptophan (trp) promoter system, and hybrid promoters such as the tac promoter. Other known bacterial promoters are also suitable. Promoters for use in bacterial systems also will contain a Shine-Dalgarno (S.D.) sequence operably linked to the DNA encoding the humanized anti-IL-23p19 antibody.

Many eukaryotic promoter sequences are known. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Inducible promoters have the additional advantage of transcription controlled by growth conditions. These include yeast promoter regions for alcohol dehydrogenase 2, isocytochrome C, acid phosphatase, derivative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Humanized anti-IL-23p19 antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, or from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., 1982, Nature 297:598-601, disclosing expression of human p-interferon cDNA in mouse cells under the control of a thymidine kinase promoter from herpes simplex virus. Alternatively, the Rous sarcoma virus long terminal repeat can be used as the promoter.

Another useful element that can be used in a recombinant expression vector is an enhancer sequence, which is used to increase the transcription of a DNA encoding a humanized anti-IL-23p19 antibody by higher eukaryotes. Many enhancer sequences are now known from mammalian genes (e.g., globin, elastase, albumin, α-fetoprotein, and insulin). Typically, however, an enhancer from a eukaryotic cell virus is used. Examples include the SV40 enhancer on the late side of the replication origin (bp 100-270), the cytomegalovirus early promoter enhancer, the polyoma enhancer on the late side of the replication origin, and adenovirus enhancers. See also Yaniv, 1982, Nature 297:17-18 for a description of enhancing elements for activation of eukaryotic promoters. The enhancer may be spliced into the vector at a position 5' or 3' to the humanized anti-IL-23p19 antibody-encoding sequence, but is preferably located at a site 5' from the promoter.

Expression vectors used in eukaryotic host cells (yeast, fungi, insect, plant, animal, human, or nucleated cells from other multicellular organisms) can also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding anti-IL-23p19 antibody. One useful transcription termination component is the bovine growth hormone polyadenylation region. See WO94/11026 and the expression vector disclosed therein. In some embodiments, humanized anti-IL-23p19 antibodies can be expressed using the CHEF system. (See, e.g., U.S. Pat. No. 5,888,809; the disclosure of which is incorporated by reference herein.)

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41 P disclosed in DD 266,710 published Apr. 12, 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for humanized anti-IL-23p19 antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402, 226); *Pichia pastors* (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*.

Suitable host cells for the expression of glycosylated humanized anti-IL-23p19 antibody are derived from multicellular organisms. Examples of invertebrate cells include plant and insect cells, including, e.g., numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* (silk worm). A variety of viral strains for transfection are publicly available, e.g., the L-1 variant of *Autographa californica* NPV and the Bm-5 strain of *Bombyx mori* NPV, and such viruses may be used, particularly for transfection of *Spodoptera frugiperda* cells.

Plant cell cultures of cotton, corn, potato, soybean, petunia, tomato, and tobacco can also be utilized as hosts.

In another aspect, expression of humanized anti-IL-23p19 is carried out in vertebrate cells. The propagation of vertebrate cells in culture (tissue culture) has become routine procedure and techniques are widely available. Examples of useful mammalian host cell lines are monkey kidney CV1 line transformed by SV40 (COS-7, ATCC CRL 1651), human embryonic kidney line (293 or 293 cells subcloned for growth in suspension culture, (Graham et al., 1977, J. Gen Virol. 36: 59), baby hamster kidney cells (BHK, ATCC CCL 10), Chinese hamster ovary cells/-DHFR1 (CHO, Urlaub et al., 1980, Proc. Natl. Acad. Sci. USA 77: 4216; e.g., DG44), mouse sertoli cells (TM4, Mather, 1980, Biol. Reprod. 23:243-251), monkey kidney cells (CV1 ATCC CCL 70), African green monkey kidney cells (VERO-76, ATCC CRL-1587), human cervical carcinoma cells (HELA, ATCC CCL 2), canine kidney cells (MDCK, ATCC CCL 34), buffalo rat liver cells (BRL 3A, ATCC CRL 1442), human lung cells (W138, ATCC CCL 75), human liver cells (Hep G2, HB 8065), mouse mammary tumor (MMT 060562, ATCC CCL51), TR1 cells (Mather et al., 1982, Annals N.Y. Acad. Sci. 383: 44-68), MRC 5 cells, FS4 cells, and human hepatoma line (Hep G2).

Host cells are transformed with the above-described expression or cloning vectors for humanized anti-IL-23p19 antibody production and cultured in conventional nutrient media modified as appropriate for inducing promoters, selecting transformants, or amplifying the genes encoding the desired sequences.

The host cells used to produce a humanized anti-IL-23p19 antibody described herein may be cultured in a variety of media. Commercially available media such as Ham's F10 (Sigma-Aldrich Co., St. Louis, Mo.), Minimal Essential Medium ((MEM), (Sigma-Aldrich Co.), RPMI-1640 (Sigma-Aldrich Co.), and Dulbecco's Modified Eagle's Medium ((DMEM), Sigma-Aldrich Co.) are suitable for culturing the host cells. In addition, any of the media described in one or more of Ham et al., 1979, Meth. Enz. 58: 44, Barnes et al., 1980, Anal. Biochem. 102: 255, U.S. Pat. No. 4,767,704, U.S. Pat. No. 4,657,866, U.S. Pat. No. 4,927,762, U.S. Pat. No. 4,560,655, U.S. Pat. No. 5,122,469, WO 90/103430, and WO 87/00195 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as gentamicin), trace elements (defined as inorganic compounds usually present at final concentrations in the micromolar range), and glucose or an equivalent energy source. Other supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, the cells may be disrupted to release protein as a first step. Particulate debris, either host cells or lysed fragments, can be removed, for example, by centrifugation or ultrafiltration. Carter et al., 1992, Bio/Technology 10:163-167 describes a procedure for isolating antibodies that are secreted to the periplasmic space of *E. coli*. Briefly, cell paste is thawed in the presence of sodium acetate (pH 3.5), EDTA, and phenylmethylsulfonylfluoride (PMSF) over about 30 minutes. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants. A variety of methods can be used to isolate the antibody from the host cell.

The antibody composition prepared from the cells can be purified using, for example, hydroxylapatite chromatography, gel electrophoresis, dialysis, and affinity chromatography, with affinity chromatography being a typical purification technique. The suitability of protein A as an affinity ligand depends on the species and isotype of any immunoglobulin Fc domain that is present in the antibody. Protein A can be used to purify antibodies that are based on human gamma1, gamma2, or gamma4 heavy chains (see, e.g., Lindmark et al., 1983 J. Immunol. Meth. 62:1-13). Protein G is recommended for all mouse isotypes and for human gamma3 (see, e.g., Guss et al., 1986 EMBO J. 5:1567-1575). A matrix to which an affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_{H3}$ domain, the Bakerbond ABX™ resin (J. T. Baker, Phillipsburg, N.J.) is useful for purification. Other techniques for protein purification such as fractionation on an ion-exchange column, ethanol precipitation, reverse phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, typically performed at low salt concentrations (e.g., from about 0-0.25M salt).

Also included are nucleic acids that hybridize under low, moderate, and high stringency conditions, as defined herein, to all or a portion (e.g., the portion encoding the variable region) of the nucleotide sequence represented by isolated polynucleotide sequence(s) that encode an antibody or antibody fragment of the present invention. The hybridizing portion of the hybridizing nucleic acid is typically at least 15 (e.g., 20, 25, 30 or 50) nucleotides in length. The hybridizing portion of the hybridizing nucleic acid is at least 80%, e.g., at least 90%, at least 95%, or at least 98%, identical to the sequence of a portion or all of a nucleic acid encoding an anti-IL-23p19 polypeptide (e.g., a heavy chain or light chain variable region), or its complement. Hybridizing nucleic acids of the type described herein can be used, for example, as a cloning probe, a primer, e.g., a PCR primer, or a diagnostic probe.

Some embodiments include isolated polynucleotides including sequences that encode an antibody or antibody fragment having the amino acid sequence of any one of SEQ ID NO: 84, 86, 88, 90, 91, 93, 95, 97, 99, 101, 103, 105, 107, 109, 111, 113, 115, 117 or 119, and that is at least 80%, at least 90%, at least 95%, at least 98%, or at least 99% identical to the polynucleotide sequences of SEQ ID NO:83, 85, 87, 89, 92, 94, 96, 98, 100, 102, 104, 106, 108, 110, 112, 114, 116 or 118.

Some embodiments include isolated polynucleotides including sequences that encode an antibody or antibody fragment having the amino acid sequence of any one of SEQ ID NO: 158, 160, 162 or 164, and that is at least 80%, at least 90%, at least 95%, at least 98%, or at least 99% identical to the polynucleotide sequences of SEQ ID NO:157, 159, 161 or 163.

Some embodiments include isolated polynucleotides including sequences that encode an antibody or antibody fragment having the amino acid sequence of any one of SEQ ID NO: 121, 123, 125, 127, 128, 130, 132, 134, 136, 138, 140, 142, 144, 146, 148, 150, 152, 154 or 156, and that is at least 80%, at least 90%, at least 95%, at least 98%, or at least 99% identical to the polynucleotide sequences of SEQ ID NO: 120, 122, 124, 126, 129, 131, 133, 135, 137, 139, 141, 143, 145, 147, 149, 151, 153 or 155.

Some embodiments include isolated polynucleotides including sequences that encode an antibody or antibody fragment having the amino acid sequence of any one of SEQ ID NO: 166, 168, 170 or 172, and that is at least 80%, at least 90%, at least 95%, at least 98%, or at least 99% identical to the polynucleotide sequences of SEQ ID NO: 165, 167, 169 or 171.

Some embodiments include isolated polynucleotides including sequences that encode an antibody or antibody fragment having the light chain variable region amino acid sequence that is at least 80%, at least 90%, at least 95%, at least 98%, or at least 99% identical to the amino acid sequence of any one of SEQ ID NO: 84, 86, 88, 90, 91, 93, 95, 97, 99, 101, 103, 105, 107, 109, 111, 113, 115, 117 or 119. Some embodiments include isolated polynucleotides including sequences that encode an antibody or antibody fragment having the light chain variable region amino acid sequence that is at least 80%, at least 90%, at least 95%, at least 98%, or at least 99% identical to the amino acid sequence of any one of SEQ ID NO:158, 160, 162 or 164. Some embodiments include isolated polynucleotides including sequences that encode an antibody or antibody fragment having the heavy chain variable region amino acid sequence that is at least 80%, at least 90%, at least 95%, at least 98%, or at least 99% identical to the amino acid sequence of any one of SEQ ID NO:121, 123, 125, 127, 128, 130, 132, 134, 136, 138, 140, 142, 144, 146, 148, 150, 152, 154 or 156. Some embodiments include isolated polynucleotides including sequences that encode an antibody or antibody fragment having the heavy chain variable region amino acid sequence that is at least 80%, at least 90%, at least 95%, at least 98%, or at least 99% identical to the amino acid sequence of any of one SEQ ID NO:166, 168, 170 or 172. As used herein, the terms "identical" or "percent identity," in the context of two or more nucleic acids or polypeptide sequences, refer to two or more sequences or subsequences that are the same or have a specified percentage of nucleotides or amino acid residues that are the same, when compared and aligned for maximum correspondence. To determine the percent identity, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In some embodiments, the two sequences that are compared are the same length after gaps are introduced within the sequences, as appropriate (e.g., excluding additional sequence extending beyond the sequences being compared). For example, when variable region sequences are compared, the leader and/or constant domain sequences are not considered. For sequence comparisons between two sequences, a "corresponding" CDR refers to a CDR in the same location in both sequences (e.g., CDR-H1 of each sequence).

The determination of percent identity or percent similarity between two sequences can be accomplished using a mathematical algorithm. A preferred, non-limiting example of a mathematical algorithm utilized for the comparison of two sequences is the algorithm of Karlin and Altschul, 1990, Proc. Natl. Acad. Sci. USA 87:2264-2268, modified as in Karlin and Altschul, 1993, Proc. Natl. Acad. Sci. USA 90:5873-5877. Such an algorithm is incorporated into the NBLAST and XBLAST programs of Altschul et al., 1990, J. Mol. Biol. 215:403-410. BLAST nucleotide searches can be performed with the NBLAST program, score=100, wordlength=12, to obtain nucleotide sequences homologous to a nucleic acid encoding a protein of interest. BLAST protein searches can be performed with the XBLAST program, score=50, wordlength=3, to obtain amino acid sequences homologous to protein of interest. To obtain gapped alignments for comparison purposes, Gapped BLAST can be utilized as described in Altschul et al., 1997, Nucleic Acids Res. 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti, 1994, Comput. Appl. Biosci. 10:3-5; and FASTA described in Pearson and Lipman, 1988, Proc. Natl. Acad. Sci. USA 85:2444-8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA. Alternatively, protein sequence alignment may be carried out using the CLUSTAL W algorithm, as described by Higgins et al., 1996, Methods Enzymol. 266:383-402.

Non-Therapeutic Uses

The antibodies described herein are useful as affinity purification agents. In this process, the antibodies are immobilized on a solid phase such a Protein A resin, using methods well known in the art. The immobilized antibody is contacted with a sample containing the IL-23p19 protein (or fragment thereof) to be purified, and thereafter the support is washed with a suitable solvent that will remove substantially all the material in the sample except the IL-2319 protein, which is bound to the immobilized antibody. Finally, the support is washed with another suitable solvent that will release the IL-23p19 protein from the antibody.

Anti-IL-23p19 antibodies, for example humanized anti-IL-23p19 antibodies, are also useful in diagnostic assays to detect and/or quantify IL-23 protein, for example, detecting IL-23 expression in specific cells, tissues, or serum. The anti-IL-23p19 antibodies can be used diagnostically to, for example, monitor the development or progression of a disease as part of a clinical testing procedure to, e.g., determine the efficacy of a given treatment and/or prevention regimen. Detection can be facilitated by coupling the anti-IL-23p19 antibody. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. See, for example, U.S. Pat. No. 4,741, 900 for metal ions which can be conjugated to antibodies for use as diagnostics according to the present invention.

The anti-IL-23p19 antibodies can be used in methods for diagnosing an IL-23-associated disorder (e.g., a disorder characterized by abnormal expression of IL-23) or to determine if a subject has an increased risk of developing an IL-23-associated disorder. Such methods include contacting a biological sample from a subject with an IL-23p19 antibody and detecting binding of the antibody to IL-23p19. By "biological sample" is intended any biological sample obtained from an individual, cell line, tissue culture, or other source of cells potentially expressing IL-23. Methods for obtaining tissue biopsies and body fluids from mammals are well known in the art.

In some embodiments, the method can further comprise comparing the level of IL-23 in a patient sample to a control sample (e.g., a subject that does not have an IL-23-associated disorder) to determine if the patient has an IL-23-associated disorder or is at risk of developing an IL-23-associated disorder.

It will be advantageous in some embodiments, for example, for diagnostic purposes to label the antibody with a detectable moiety. Numerous detectable labels are available, including radioisotopes, fluorescent labels, enzyme substrate labels and the like. The label may be indirectly conjugated with the antibody using various known techniques.

For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody can be conjugated with a small hapten (such as digoxin) and one of the different types of labels mentioned above is conjugated with an anti-hapten antibody (e.g., anti-digoxin antibody). Thus, indirect conjugation of the label with the antibody can be achieved.

Exemplary radioisotopes labels include $^{35}$S, $^{14}$C, $^{125}$I, $^{3}$H, and $^{131}$I. The antibody can be labeled with the radioisotope, using the techniques described in, for example, Current Protocols in Immunology, Volumes 1 and 2, 1991, Coligen et al., Ed. Wiley-Interscience, New York, N.Y., Pubs. Radioactivity can be measured, for example, by scintillation counting.

Exemplary fluorescent labels include labels derived from rare earth chelates (europium chelates) or fluorescein and its derivatives, rhodamine and its derivatives, dansyl, Lissamine, phycoerythrin, and Texas Red are available. The fluorescent labels can be conjugated to the antibody via known techniques, such as those disclosed in Current Protocols in Immunology, for example. Fluorescence can be quantified using a fluorimeter.

There are various well-characterized enzyme-substrate labels known in the art (see, e.g., U.S. Pat. No. 4,275,149 for a review). The enzyme generally catalyzes a chemical alteration of the chromogenic substrate that can be measured using various techniques. For example, alteration may be a color change in a substrate that can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light that can be measured, using a chemiluminometer, for example, or donates energy to a fluorescent acceptor.

Examples of enzymatic labels include luciferases such as firefly luciferase and bacterial luciferase (U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (such as glucose oxidase, galactose oxidase, and glucose-6-phosphate dehydrogenase), heterocydic oxidases (such as uricase and xanthine oxidase), lactoperoxidase, microperoxidase, and the like. Techniques for conjugating enzymes to antibodies are described, for example, in O'Sullivan et al., 1981, Methods for the Preparation of Enzyme-Antibody Conjugates for use in Enzyme Immunoassay, in Methods in Enzym. (J. Langone & H. Van Vunakis, eds.), Academic press, N.Y., 73: 147-166.

Examples of enzyme-substrate combinations include, for example: Horseradish peroxidase (HRPO) with hydrogen peroxidase as a substrate, wherein the hydrogen peroxidase oxidizes a dye precursor such as orthophenylene diamine (OPD) or 3,3',5,5'-tetramethyl benzidine hydrochloride (TMB); alkaline phosphatase (AP) with para-Nitrophenyl phosphate as chromogenic substrate; and β-D-galactosidase (β-D-Gal) with a chromogenic substrate such as p-nitrophenyl-β-D-galactosidase or fluorogenic substrate 4-methylumbelliferyl-β-D-galactosidase.

Numerous other enzyme-substrate combinations are available to those skilled in the art. For a general review of these, see U.S. Pat. No. 4,275,149 and U.S. Pat. No. 4,318,980.

In another embodiment, the humanized anti-IL-23p19 antibody is used unlabeled and detected with a labeled antibody that binds the humanized anti-IL-23p19 antibody.

The antibodies described herein may be employed in any known assay method, such as competitive binding assays, direct and indirect sandwich assays, and immunoprecipitation assays. See, e.g., Zola, Monoclonal Antibodies: A Manual of Techniques, pp. 147-158 (CRC Press, Inc. 1987).

The anti-IL-23p19 antibody or antigen binding fragment thereof can be used to inhibit the binding of IL-23 to the IL-23 receptor. Such methods comprise administering an anti-IL-23p19 antibody or antigen binding fragment thereof to a cell (e.g., a mammalian cell) or cellular environment, whereby signaling mediated by the IL-23 receptor is inhibited. These methods can be performed in vitro or in vivo. By "cellular environment" is intended the tissue, medium, or extracellular matrix surrounding a cell. The anti-IL-23p19 antibody or antigen binding fragment thereof is administered to the cellular environment of a cell in such a manner that the antibody or fragment is capable of binding to IL-23 molecules outside of and surrounding the cell, therefore, preventing the binding of IL-23 to its receptor.

Diagnostic Kits

An anti-IL-23p19 antibody can be used in a diagnostic kit, i.e., a packaged combination of reagents in predetermined amounts with instructions for performing the diagnostic assay. Where the antibody is labeled with an enzyme, the kit may include substrates and cofactors required by the enzyme such as a substrate precursor that provides the detectable chromophore or fluorophore. In addition, other additives may be included such as stabilizers, buffers (for example a block buffer or lysis buffer), and the like. The relative amounts of the various reagents may be varied widely to provide for concentrations in solution of the reagents that substantially optimize the sensitivity of the assay. The reagents may be provided as dry powders, usually lyophilized, including excipients that on dissolution will provide a reagent solution having the appropriate concentration.

Therapeutic Uses

In another embodiment, a humanized anti-IL-23p19 antibody disclosed herein is useful in the treatment of various disorders associated with the expression of IL-23p19 as described herein. Methods for treating an IL-23 associated disorder comprise administering a therapeutically effective amount of a humanized anti-IL-23p19 antibody to a subject in need thereof.

The humanized anti-IL-23p19 antibody or agent is administered by any suitable means, including parenteral, subcutaneous, intraperitoneal, intrapulmonary, and intranasal, and, if desired for local immunosuppressive treatment, intralesional administration (including perfusing or otherwise contacting the graft with the antibody before transplantation). The humanized anti-IL-23p19 antibody or agent can be administered, for example, as an infusion or as a bolus. Parenteral infusions include intramuscular, intravenous, intraarterial, intraperitoneal, or subcutaneous administration. In addition, the humanized anti-IL-23p19 antibody is suitably administered by pulse infusion, particularly with declining doses of the antibody. In one aspect, the dosing is given by injections, most preferably intravenous or subcutaneous injections, depending in part on whether the administration is brief or chronic.

For the prevention or treatment of disease, the appropriate dosage of antibody will depend on a variety of factors such as the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

Depending on the type and severity of the disease, about 1 µg/kg to 20 mg/kg (e.g., 0.1-15 mg/kg) of antibody is an initial candidate dosage for administration to the patient, whether, for example, by one or more separate administrations, or by continuous infusion. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen is that disclosed in WO 94/04188.

The term "suppression" is used herein in the same context as "amelioration" and "alleviation" to mean a lessening of one or more characteristics of the disease.

The antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody to be administered will be governed by such considerations, and is the minimum amount necessary to prevent, ameliorate, or treat the disorder associated with IL-23 expression.

The antibody need not be, but is optionally, formulated with one or more agents currently used to prevent or treat the disorder in question. The effective amount of such other agents depends on the amount of humanized anti-IL-23p19 antibody present in the formulation, the type of disorder or treatment, and other factors discussed above. These are generally used in the same dosages and with administration routes as used hereinbefore or about from 1 to 99% of the heretofore employed dosages.

IL-23-Associated Disorders

The anti-IL-23p19 antibodies or agents are useful for treating or preventing an immunological disorder characterized by abnormal expression of IL-23, e.g., by inappropriate activation of immune cells (e.g., lymphocytes or dendritic cells). Such abnormal expression of IL-23 can be due to, for example, increased IL-23 protein levels. The anti-IL-23p19 antibodies or antigen binding fragments thereof also find use in the treatment or prevention of respiratory disorders, metabolic disorders, for example diabetes mellitus, and certain cancers. Treatment or prevention of the immunological disorder, respiratory disorder, metabolic disorder or cancer, according to the methods described herein, is achieved by administering to a subject in need of such treatment or prevention an effective amount of the anti-IL-23p19 antibody or agent, whereby the antibody decreases the activity of IL-23 associated with the disease state.

Immunological diseases that are characterized by inappropriate activation of immune cells and that can be treated or prevented by the methods described herein can be classified, for example, by the type(s) of hypersensitivity reaction(s) that underlie the disorder. These reactions are typically classified into four types: anaphylactic reactions, cytotoxic (cytolytic) reactions, immune complex reactions, or cell-mediated immunity (CMI) reactions (also referred to as delayed-type hypersensitivity (DTH) reactions). (See, e.g., Fundamental Immunology (William E. Paul ed., Raven Press, N.Y., 3rd ed. 1993).) Immunological diseases include inflammatory diseases and autoimmune diseases.

Specific examples of such immunological diseases include the following: rheumatoid arthritis, autoimmune demyelinative diseases (e.g., multiple sclerosis, allergic encephalomyelitis), endocrine opthalmopathy, uveoretinitis, systemic lupus erythematosus, myasthenia gravis, Grave's disease, glomerulonephritis, autoimmune hepatological disorder, inflammatory bowel disease (e.g., Crohn's disease or ulcerative colitis), anaphylaxis, allergic reaction, Sjogren's syndrome, type I diabetes mellitus, primary biliary cirrhosis, Wegener's granulomatosis, fibromyalgia, polymyositis, dermatomyositis, inflammatory myositis, multiple endocrine failure, Schmidt's syndrome, autoimmune uveitis, Addison's disease, adrenalitis, thyroiditis, Hashimoto's thyroiditis, autoimmune thyroid disease, pernicious anemia, gastric atrophy, chronic hepatitis, lupoid hepatitis, atherosclerosis, subacute cutaneous lupus erythematosus, hypoparathyroidism, Dressler's syndrome, autoimmune thrombocytopenia, idiopathic thrombocytopenic purpura, hemolytic anemia, pemphigus vulgaris, pemphigus, dermatitis herpetiformis, alopecia arcata, pemphigoid, scleroderma, progressive systemic sclerosis, CREST syndrome (calcinosis, Raynaud's phenomenon, esophageal dysmotility, sclerodactyl), and telangiectasia), male and female autoimmune infertility, ankylosing spondolytis, ulcerative colitis, mixed connective tissue disease, polyarteritis nedosa, systemic necrotizing vasculitis, atopic dermatitis, atopic rhinitis, Goodpasture's syndrome, Chagas' disease, sarcoidosis, rheumatic fever, asthma, recurrent abortion, anti-phospholipid syndrome, farmer's lung, erythema multiforme, post cardiotomy syndrome, Cushing's syndrome, autoimmune chronic active hepatitis, bird-fancier's lung, toxic epidermal necrolysis, Alport's syndrome, alveolitis, allergic alveolitis, fibrosing alveolitis, interstitial lung disease, erythema nodosum, pyoderma gangrenosum, transfusion reaction, Takayasu's arteritis, polymyalgia rheumatica, temporal arteritis, schistosomiasis, giant cell arteritis, ascariasis, aspergillosis, Sampter's syndrome, eczema, lymphomatoid granulomatosis, Behcet's disease, Caplan's syndrome, Kawasaki's disease, dengue, encephalomyelitis, endocarditis, endomyocardial fibrosis, endophthalmitis, erythema elevatum et diutinum, psoriasis, psoriatic arthritis, erythroblastosis fetalis, eosinophilic faciitis, Shulman's syndrome, Felty's syndrome, filariasis, cyclitis, chronic cyclitis, heterochronic cyclitis, Fuch's cyclitis, IgA nephropathy, Henoch-Schonlein purpura, graft versus host disease, transplantation rejection, cardiomyopathy, Eaton-Lambert syndrome, relapsing polychondritis, cryoglobulinemia, Waldenstrom's macroglobulemia, Evan's syndrome, acute respiratory distress syndrome, pulmonary inflammation, osteoporosis, delayed type hypersensitivity and autoimmune gonadal failure.

In some embodiments, the immunological disorder is a T cell-mediated immunological disorder and accordingly, the anti-IL-23p19 antibodies and agents as described herein are also useful for treating or preventing T cell-mediated immunological disorders.

In one aspect, the anti-IL-23p19 antibodies or agents are useful for treating or preventing a respiratory disorder in which IL-23 is abnormally expressed. Treatment or prevention of the respiratory disorder, according to the methods described herein, is achieved by administering to a subject in need of such treatment or prevention an effective amount of the anti-IL-23p19 antibody or agent, whereby the antibody decreases the activity of IL-23 associated with the disease state. These include, but are not limited to: respiratory complaints, obstructive pulmonary diseases of various origins, pulmonary emphysema of various origins, restrictive pulmonary diseases, interstitial pulmonary diseases, interstitial lung disease, cystic fibrosis, bronchitis of various origins, bronchiectasis, ARDS (adult respiratory distress syndrome) and all forms of pulmonary oedema; obstructive pulmonary diseases selected from among COPD (chronic obstructive pulmonary disease), asthma, bronchial asthma, paediatric asthma, severe asthma, acute asthma attacks and chronic bronchitis; pulmonary emphysema which has its origins in COPD (chronic obstructive pulmonary disease) or a1-proteinase inhibitor deficiency; restrictive pulmonary diseases selected from among allergic alveolitis, restrictive pulmonary diseases triggered by work-related noxious substances, such as asbestosis or silicosis, and restriction caused by lung tumours, such as lymphangiosis carcinomatosa, bronchoalveolar carcinoma and lymphomas; pneumonia caused by infections, such as for example infection by viruses, bacteria, fungi, protozoa, helminths or other pathogens, pneumonitis caused by various factors, such as for example aspiration and left heart insufficiency, radiation-induced pneumonitis or fibrosis, collagenoses, such as for example lupus erythematosus, systemic scleroderma or sarcoidosis, granulomatoses, such as for example Boeck's disease, idiopathic interstitial pneumonia or idiopathic pulmonary fibrosis (IPF); mucoviscidosis, bronchitis caused by bacterial or viral infection, allergic bronchitis and toxic bronchitis; bronchiectasis; pulmonary oedema, for example, toxic pulmonary oedema after aspiration or inhalation of toxic substances and foreign substances; rhinitis, arthritis and related arthropathies, psoriasis, myeloid leukemia, multiple sclerosis, Alzheimer's disease, glomerulonephritis, and chronic atopic dermatitis.

In another aspect, the anti-IL-23p19 antibodies and agents as described herein are also useful for treating cancers, in which IL-23 is abnormally expressed.

IL-23-expressing cancers that can be treated by the methods described herein include, for example, leukemia, such as acute leukemia, acute lymphocytic leukemia, acute myelocytic leukemia (e.g., myeloblastic, promyelocytic, myelomonocytic, monocytic, or erythroleukemia), chronic leukemia, chronic myelocytic (granulocytic) leukemia, or chronic lymphocytic leukemia; Polycythemia vera; Lymphoma (e.g., Hodgkin's disease or Non-Hodgkin's disease); multiple myeloma, Waldenstrom's macroglobulinemia; heavy chain disease; solid tumors such sarcomas and carcinomas (e.g., fibrosarcoma, myxosarcoma, liposarcoma, chondrosarcoma, osteogenic sarcoma, osteosarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular tumor, lung carcinoma, small cell lung carcinoma, non small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, retinoblastoma, nasopharyngeal carcinoma, or esophageal carcinoma).

Pharmaceutical Compositions and Administration Thereof

A composition comprising an IL-23p19 binding agent (e.g., an anti-IL-23p19 antibody) can be administered to a subject having or at risk of having an immunological disorder, respiratory disorder or a cancer. The invention further provides for the use of a IL-23p19 binding agent (e.g., an anti-IL-23p19 antibody) in the manufacture of a medicament for prevention or treatment of a cancer, respiratory disorder or immunological disorder. The term "subject" as used herein means any mammalian patient to which an IL-23p19 binding agent can be administered, including, e.g., humans and non-human mammals, such as primates, rodents, and dogs. Subjects specifically intended for treatment using the methods described herein include humans. The antibodies or agents can be administered either alone or in combination with other compositions in the prevention or treatment of the immunological disorder, respiratory disorder or cancer. Such compositions which can be administered in combination with the antibodies or agents include methotrexate (MTX) and immunomodulators, e.g. antibodies or small molecules.

Examples of antibodies for use in such pharmaceutical compositions are those that comprise a humanized antibody or antibody fragment having the light chain variable region amino acid sequence of any of SEQ ID NO: 84, 86, 88, 90, 91, 93, 95, 97, 99, 101, 103, 105, 107, 109, 111, 113, 115, 117 or 119. Examples of antibodies for use in such pharmaceutical compositions are also those that comprise a humanized antibody or antibody fragment having the heavy chain variable region amino acid sequence of any of SEQ ID NO: 121, 123, 125, 127, 128, 130, 132, 134, 136, 138, 140, 142, 144, 146, 148, 150, 152, 154 or 156.

Further examples of antibodies for use in such pharmaceutical compositions are also those that comprise a humanized antibody or antibody fragment having the light chain variable region amino acid sequence of any of SEQ ID NO:158, 160, 162 or 164. Preferred antibodies for use in such pharmaceutical compositions are also those that comprise a humanized antibody or antibody fragment having the heavy chain variable region amino acid sequence of any of SEQ ID NO:166, 168, 170 or 172.

Further examples of antibodies for use in such pharmaceutical compositions are also those that comprise a humanized antibody or antibody fragment having the light chain variable region and heavy chain variable region of any of SEQ ID NO: 160 and 166, SEQ ID NO: 160 and 168, SEQ ID NO: 158 and 166 or SEQ ID NO: 158 and 168.

Further examples of antibodies for use in such pharmaceutical compositions are also those that comprise a humanized antibody having the light chain region amino acid sequence of any of SEQ ID NO:174 or 180. Preferred antibodies for use in such pharmaceutical compositions are also those that comprise humanized antibody having the heavy chain variable region amino acid sequence of any of SEQ ID NO:176 or 178.

Further examples of antibodies for use in such pharmaceutical compositions are also those that comprise Antibody A, Antibody B, Antibody C or Antibody D.

Various delivery systems are known and can be used to administer the IL-23p19 binding agent. Methods of introduction include but are not limited to intradermal, intramuscular, intraperitoneal, intravenous, subcutaneous, intranasal, epidural, and oral routes. The IL-23p19 binding agent can be administered, for example by infusion, bolus or injection, and can be administered together with other biologically active agents such as chemotherapeutic agents. Administration can be systemic or local. In preferred embodiments, the administration is by subcutaneous injection. Formulations for such injections may be prepared in for example prefilled syringes that may be administered once every other week.

In specific embodiments, the IL-23p19 binding agent composition is administered by injection, by means of a catheter, by means of a suppository, or by means of an implant, the implant being of a porous, non-porous, or gelatinous material, including a membrane, such as a sialastic membrane, or a fiber. Typically, when administering the composition, materials to which the anti-IL-23p19 antibody or agent does not absorb are used.

In other embodiments, the anti-IL-23p19 antibody or agent is delivered in a controlled release system. In one embodiment, a pump may be used (see, e.g., Langer, 1990, Science 249:1527-1533; Sefton, 1989, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used. (See, e.g., Medical Applications of Controlled Release (Langer and Wise eds., CRC Press, Boca Raton, Fla., 1974); Controlled Drug Bioavailability, Drug Product Design and Performance (Smolen and Ball eds., Wiley, New York, 1984); Ranger and Peppas, 1983, Macromol. Sci. Rev. Macromol. Chem. 23:61. See also Levy et al., 1985, Science 228:190; During et al., 1989, Ann. Neurol. 25:351; Howard et al., 1989, J. Neurosurg. 71:105.) Other controlled release systems are discussed, for example, in Langer, supra.

An IL-23p19 binding agent (e.g., an anti-IL-23p19 antibody) can be administered as pharmaceutical compositions comprising a therapeutically effective amount of the binding agent and one or more pharmaceutically compatible ingredients.

In typical embodiments, the pharmaceutical composition is formulated in accordance with routine procedures as a pharmaceutical composition adapted for intravenous or subcutaneous administration to human beings. Typically, compositions for administration by injection are solutions in sterile isotonic aqueous buffer. Where necessary, the pharmaceutical can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the pharmaceutical is to be administered by infusion, it can be dispensed with an infusion bottle containing sterile pharmaceutical grade water or saline. Where the pharmaceutical is administered by injection, an ampoule of sterile water for injection or saline can be provided so that the ingredients can be mixed prior to administration.

Further, the pharmaceutical composition can be provided as a pharmaceutical kit comprising (a) a container containing a IL-23p19 binding agent (e.g., an anti-IL-23p19 antibody) in lyophilized form and (b) a second container containing a pharmaceutically acceptable diluent (e.g., sterile water) for injection. The pharmaceutically acceptable diluent can be used for reconstitution or dilution of the lyophilized anti-IL-23p19 antibody or agent. Optionally associated with such container(s) can be a notice in the form prescribed by a governmental agency regulating the manufacture, use or sale of pharmaceuticals or biological products, which notice reflects approval by the agency of manufacture, use or sale for human administration.

The amount of the IL-23p19 binding agent (e.g., anti-IL-23p19 antibody) that is effective in the treatment or prevention of an immunological disorder or cancer can be determined by standard clinical techniques. In addition, in vitro assays may optionally be employed to help identify optimal dosage ranges. The precise dose to be employed in the formulation will also depend on the route of administration, and the stage of immunological disorder or cancer, and should be decided according to the judgment of the practitioner and each patient's circumstances. Effective doses may be extrapolated from dose-response curves derived from in vitro or animal model test systems.

Generally, the dosage of an anti-IL-23p19 antibody or IL-23p19 binding agent administered to a patient with an immunological disorder or IL-23p19-expressing cancer is typically about 0.1 mg/kg to about 100 mg/kg of the subject's body weight. The dosage administered to a subject is about 0.1 mg/kg to about 50 mg/kg, about 1 mg/kg to about 30 mg/kg, about 1 mg/kg to about 20 mg/kg, about 1 mg/kg to about 15 mg/kg, or about 1 mg/kg to about 10 mg/kg of the subject's body weight.

Exemplary doses include, but are not limited to, from 1 ng/kg to 100 mg/kg. In some embodiments, a dose is about 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg or about 16 mg/kg. The dose can be administered, for example, daily, once per week (weekly), twice per week, thrice per week, four times per week, five times per week, six times per week, biweekly or monthly, every two months, or every three months. In specific embodiments, the dose is about 0.5 mg/kg/week, about 1 mg/kg/week, about 2 mg/kg/week, about 3 mg/kg/week, about 4 mg/kg/week, about 5 mg/kg/week, about 6 mg/kg/week, about 7 mg/kg/week, about 8 mg/kg/week, about 9 mg/kg/week, about 10 mg/kg/week, about 11 mg/kg/week, about 12 mg/kg/week, about 13 mg/kg/week, about 14 mg/kg/week, about 15 mg/kg/week or about 16 mg/kg/week. In some embodiments, the dose ranges from about 1 mg/kg/week to about 15 mg/kg/week.

In some embodiments, the pharmaceutical compositions comprising the IL-23p19 binding agent can further comprise a therapeutic agent, either conjugated or unconjugated to the binding agent. The anti-IL-23p19 antibody or IL-23p19 binding agent can be co-administered in combination with one or more therapeutic agents for the treatment or prevention of immunological disorders or cancers.

Such combination therapy administration can have an additive or synergistic effect on disease parameters (e.g., severity of a symptom, the number of symptoms, or frequency of relapse).

With respect to therapeutic regimens for combinatorial administration, in a specific embodiment, an anti-IL-23p19 antibody or IL-23p19 binding agent is administered concurrently with a therapeutic agent. In another specific embodiment, the therapeutic agent is administered prior or subsequent to administration of the anti-IL-23p19 antibody or IL-23p19 binding agent, by at least an hour and up to several months, for example at least an hour, five hours, 12 hours, a day, a week, a month, or three months, prior or subsequent to administration of the anti-IL-23p19 antibody or IL-23p19 binding agent.

Articles of Manufacture

In another aspect, an article of manufacture containing materials useful for the treatment of the disorders described above is included. The article of manufacture comprises a container and a label. Suitable containers include, for example, bottles, vials, syringes, and test tubes. The containers may be formed from a variety of materials such as glass or plastic. The container holds a composition that is effective for treating the condition and may have a sterile access port. For example, the container may be an intravenous solution bag or a vial having a stopper pierceable by a hypodermic injection needle. The active agent in the composition is the humanized anti-IL-23p19 antibody. The label on or associated with the container indicates that the composition is used for treating the condition of choice. The article of manufacture may further comprise a second container comprising a pharmaceutically-acceptable buffer, such as phosphate-buffered saline, Ringer's solution, and dextrose solution. It may further include other materials desirable from a commercial and user standpoint, including other buffers, diluents, filters, needles, syringes, and package inserts with instructions for use.

The invention is further described in the following examples, which are not intended to limit the scope of the invention.

EXAMPLES

Example 1: Production of Humanized Anti-IL-23p19 Antibodies

Mouse lead antibody 6B8 was converted to a chimeric antibody consisting of the mouse variable domain of 6B8 and a human constant IgG1 KO domain. Mouse antibody 6B8 is shown in Tables 1 and 2 herein above. The IgG1 KO (knock out) has two replacement mutations (Leu234Ala and Leu235Ala) that eliminate ADCC and CDC activity by reducing effector functions such as FcγR and complement binding. The variable domains of the mouse and chimeric antibodies are identical. Chimeric antibodies are generated to confirm the function of the antibody and to ensure the correct sequence has been obtained. The variable region of the antibody is then humanized through a design and screening process. A library was made where human and mouse residues were varied in such a way that in any given position there could be either a human or mouse residue. Such a library was made for those amino acids that were different between human germline and mouse antibody. Only the clones that retain the function of the parent mouse antibody were selected. Representative humanized variable regions for antibody 6B8 are shown in Tables 5 and 6.

In this manner, Antibody A, Antibody B, Antibody C and Antibody D were humanized antibodies derived from mouse antibody 6B8 (cloned into a human IgG1-KO (KO=knockout)/kappa backbone. Antibodies A, B, C and D are shown in Table 7.

Example 2: Binding of Antibodies to Recombinant IL-23 Protein

A) Kinetics and affinity of mouse anti-IL-23p19 antibodies binding to recombinant human IL-23 are shown below (Table 9). Kinetics and binding affinities were measured using the Fortebio Octet (Fortebio, Menlo Park, Calif.) using material generated from hybridoma following single column purification. Since the Octet is not a fluidics based technology, this method does not provide precise determination of off-rate. In some cases, only a estimate of affinity can be obtained.

TABLE 9

| Antibody | ka (1/Ms) | kd (1/s) | KD (pM) |
|---|---|---|---|
| 18C4 | 3.84E+05 | 2.14E−06 | 5.57 |
| 18E 5 | 3.29E+05 | 2.61E−06 | 7.93 |
| 18D3 | 3.19E+05 | 2.16E−06 | 6.78 |
| 20 E8 | 4.21E+05 | 2.69E−04 | 638 |
| 22 E2 | 3.46E+05 | 3.53E−04 | 1024 |
| 24A5 | 2.02E+05 | 4.57E−06 | 22.6 |
| 15C11 | 4.11E+05 | 1.07E−05 | 26 |
| 43F5 | 1.72E+05 | 5.96E−06 | 34.6 |
| 27G8 | 1.57E+05 | 4.26E−06 | 27.2 |
| 31H9 | 2.99E+05 | 3.45E−06 | 11.5 |
| 2D1 |  | <1e−6 | <1 |
| 9D12 |  | <1e−6 | <1 |
| 6B8 |  | <1e−6 | <1 |
| 73H10 | 5.29E+04 | 5.24E−06 | 99.2 |
| 74H3 | 3.06E+04 | 2.09E−06 | 68.3 |
| 35H8 |  |  |  |
| 26F7 | 4.76E+05 | 1.34E−05 | 28.1 |
| 34G3 | 9.18E+05 | 3.10E−05 | 32.8 |
| 34D9 | 3.44E+03 | 1.87E−06 | 544 |

B) Affinities were measured for humanized antibodies derived from mouse antibody 6B8. Kinetic binding data, measured using the ProteON XPR36 (Biorad, Hercules, Calif.) and globally fit to a 1:1 binding model, demonstrated the interactions with recombinant IL-23 either with or without a 21 amino acid linker covalently joining the p19 and p40 subunits to be of high affinity, in the range of 1 pM~100 pM (Table 10). Antibody 6H12 (disclosed in WO 2007/027714), antibody QF20 (disclosed in WO 2007/024846) and antibody C1273 (disclosed in WO 2007/005955) were also tested.

TABLE 10

| | Human IL-23 with linker | | | Human IL-23 no linker | | |
|---|---|---|---|---|---|---|
| Antibody | ka (1/Ms) | kd (1/s) | KD (pM) | ka (1/Ms) | kd (1/s) | KD (pM) |
| Mouse 6B8 | | | | 5.57E+05 | 1.38E−05 | 24.5 |
| Antibody A | 6.27E+05 | <1e−6 | <1 | 5.51E+05 | <1e−6 | <1 |
| Antibody B | 3.56E+05 | <1e−6 | <1 | 5.17E+05 | <1e−6 | <1 |
| Antibody C | 3.74E+05 | 1.19E−05 | 31.8 | 4.54E+05 | 1.65E−05 | 36.3 |
| Antibody D | 3.82E+05 | 4.07E−05 | 107 | 3.66E+05 | 4.93E−05 | 135 |
| C-1273 | | | | 3.60E+05 | 5.75E−06 | 15.8 |
| 6H12 | | | | 4.99E+05 | 1.07E−04 | 214 |
| QF20 | | | | 2.03E+05 | 5.89E−06 | 2.91 |

C) Affinity and kinetic data for the anti-IL-23p19 antibodies binding to cynomologous IL-23 were measured on the ProteON XPR36, and globally fit to a 1:1 binding model (Table 11). Antibody 6H12 (disclosed in WO 2007/027714), antibody QF20 (disclosed in WO 2007/024846) and antibody C1273 (disclosed in WO 2007/005955) were also tested.

TABLE 11

| Antibody | $K_D$ (pM) | $k_a$ (1/Ms) | $k_d$ (1/s) |
|---|---|---|---|
| Antibody A | <1 | 2.95E+06 | <1e−6 |
| Antibody B | <1 | 2.99E+06 | <1e−6 |
| Antibody C | 2.9 | 3.23E+06 | 9.36E−06 |
| Antibody D | 15.9 | 2.07E+06 | 3.29E−05 |
| C-1273 | >5,000 | n/a | n/a |
| 6H12 | 157 | 9.91E+05 | 1.56E−04 |
| QF20 | 1.2 | 3.90E+06 | 4.78E−06 |

D) Molecular Selectivity over human IL-12

The anti-IL-23p19 antibodies were also injected over a human IL-12 surface at a concentration of 100 nM. The binding signal for these antibodies measured using the Fortebio Octet is zero, which indicates that these antibodies selectively bind to human IL-23. The binding of the anti-IL-23p19 antibodies to IL-23 was also analyzed in the presence of 50% human serum and no significant effect of serum on binding on-rate was observed demonstrating high specificity.

Example 3: Competition Binding Assay of Human IL-23 Binding to Human IL-23R/Fc

Human IL-23R-Fc was captured on the biosensor surface and 10 nM of human IL-23 was injected. The sensorgram indicates the specific binding between IL-23 and the IL-23 receptor (FIG. 2, top trace). Antibodies were then co-injected with 10 nM human IL-23 to assess whether antibody binding to the IL-23 could inhibit the interaction between IL-23 and the IL-23 receptor. In this example, if the antibody binds to human IL-23 and is able to inhibit the interaction then reduced or no binding will be observed (FIG. 2, bottom trace). In the example shown an equivalent molar concentration of Antibody A was co-injected with 10 nM recombinant human IL-23.

Example 4: Functional Cell Assays, Inhibition of IL-17 Production from IL-23 Stimulated Mouse Splenocytes One functional cell assay for anti-IL-23p19 antibodies measures their ability to inhibit IL-23 stimulated IL-17 production from mononuclear cells isolated from mouse spleens. Human recombinant IL-23 protein is capable of stimulating IL-17 release from mouse splenocytes. In addition, a natural source of human IL-23 found in the supernatant of activated human monocytic THP-1 cells can be used to stimulate IL-17 production from mouse mononuclear cells.

Human recombinant IL-23 or natural human IL-23 from activated THP-1 cells was preincubated with titrated anti-IL-23p19 antibodies. The IL-23/antibody combinations were then added to freshly isolated murine splenocytes. Recombinant IL-23 alone was used as a positive control. After two days in culture, cell supernatants were collected and assayed for IL-17 by ELISA (R&D Systems, Minneapolis, Minn.). Representative $IC_{50}$ values for anti-IL-23p19 antibodies are shown below. The tested antibodies are mouse antibodies derived from hybridomas (rows 1-19, see tables 1 and 2), chimeric antibodies (rows 20-23), and Antibodies A to D. Antibody 6H12 (disclosed in WO 2007/027714), antibody QF20 (disclosed in WO 2007/024846) and antibody C1273 (disclosed in WO 2007/005955) were also tested.

TABLE 12

| Antibody | $IC_{50}$ Values (pM), recombinant human IL-23 | $IC_{50}$ Values (pM), natural human IL-23 |
|---|---|---|
| 18C4 | 471 | 100, 413 |
| 18E5 | not determined | 9, 9, 13 |
| 18D3 | 234 | not determined |
| 20E8 | not determined | 438, 561 |
| 22E2 | 61, 130 | 117, 35 |
| 24A5 | 22, 37 | 85, 31 |
| 15C11 | 126 | 232 |
| 43F5 | 250, 8000 | 8000 |
| 27G8 | 235 | 5000 |
| 31H9 | 960 | 2000 |
| 2D1 | not determined | 2336, 1911, 1597 |
| 9D12 | 59 | 281, 138 |
| 6B8 | 13 | 8, 2 |
| 73H10 | 1411 | not determined |
| 74H3 | 1352 | not determined |
| 36H8 | not determined | not determined |
| 26F7 | 27 | 2, 8 |
| 34G3 | 336 | 27, 25 |
| 34D9 | 510 | 456 |
| Chimeric 18E5 | 31 | 8, 36, 10, 9 |
| Chimeric 22E2 | 100 | 9, 178 |
| Chimeric 24A5 | 404 | 95, 102 |
| Chimeric 6B8 | 26, 37, 57 | 5, 2, 6, 3 |
| Antibody A | 5, 5, 5, 15 | 1, 1 |
| Antibody B | 13, 30, 54, 42 | 9, 8 |
| Antibody C | 53, 71, 162, 89 | 16, 32 |
| Antibody D | 236, 225, 614, 458 | 133, 125 |
| 6H12 | 1600, 806, 1300 | 957, 4400, 1013, 439 |
| QF20 | not determined | 7, 12 |
| C1273 | not determined | 93, 44 |

Example 5: Functional Specificity Testing Against IL-12 in a Human Activated T Cell Assay Anti-IL-23p19 antibodies were tested for functional inhibition of IL-12 in a human activated T cell assay. Human recombinant IL-12 (1 ng/ml) was preincubated with 5 μg/ml anti-IL-23p19 antibodies. The IL-12/antibody combinations were then added to human PHA-derived T cell blasts. Recombinant IL-12 alone was used as a positive control. An anti-IL-12p70 antibody (Bender MedSystems, Vienna, Austria) was used as a control inhibitory antibody. After two days in culture, cell supernatants were collected and assayed for IFN-γ by ELISA (R&D Systems). Samples were tested in triplicate and the average pg/ml of IFN-γ was determined. Results (with standard deviations) are shown in the table below.

TABLE 13

| Antibody | Cytokine Stimulation | Average pg/ml IFN-γ +/− Standard Deviation |
|---|---|---|
| no antibody | None | 87 +/− 7 |
| no antibody | 1 ng/ml IL-12 | 532 +/− 51 |
| chimeric 18E5 | 1 ng/ml IL-12 | 511 +/− 3 |
| chimeric 6B8 | 1 ng/ml IL-12 | 523 +/− 60 |
| Antibody A | 1 ng/ml IL-12 | 497 +/− 30 |
| Antibody B | 1 ng/ml IL-12 | 537 +/− 2 |
| Antibody C | 1 ng/ml IL-12 | 495 +/− 25 |
| Antibody D | 1 ng/ml IL-12 | 539 +/− 38 |
| anti-IL-12p70 antibody | 1 ng/ml IL-12 | 119 +/− 12 |

Example 6: Inhibition of IL-23 Induced STAT3 Phosphorylation in the Human Cell Line DB The human cell line DB (ATCC, Manassas, Va.) responds to IL-23 stimulation through an endogenous IL-23R complex (IL-23R and IL-12Rβ1) and phosphorylates STAT3 in an IL-23 dose dependent manner. An assay was developed for testing anti-IL-23p19 antibody inhibition of IL-23 induced STAT3 phosphorylation. DB cells were plated at 1×10e6 cells/well in a 96 well plate. Antibodies to be tested were serially diluted and preincubated with recombinant human IL-23 (10 ng/ml) for 1 hour at room temperature. The antibody/IL-23 mixture was then added to the cells for 30 minutes at 37° C. Cells were harvested by centrifugation at 4° C. for 10 minutes and then lysed in ice cold buffer (Cell Signaling Technology, Beverly, Mass.). A portion of the lysate was run in a phospho-STAT3 ELISA (Invitrogen). Antibody $IC_{50}$ values were calculated as percent inhibition of STAT3 phosphorylation compared to control wells without antibody. Representative $IC_{50}$ values are shown in the table below.

TABLE 14

| Antibody | $IC_{50}$ (pM) |
|---|---|
| Antibody A | 25, 15, 38, 23, 13, 18 |
| Antibody B | 73, 84 |
| Antibody C | 132, 80 |
| Antibody D | 158 |
| QF20 | 26, 26, 27 |
| C-1273 | 163, 438 |

Example 7: In Vivo Model of IL-23 Induced Cytokine Production in the Mouse Ear An in vivo model in the mouse was used. Recombinant human IL-23 is injected into the skin of the mouse ear for 4 consecutive days resulting in epidermal thickening and up-regulation of IL-17 and IL-22 protein. Anti-IL-23p19 antibodies were evaluated in this model. A single intraperitoneal injection of 1 mg/kg or 5 mg/kg antibody was administered 1 hour prior to the initial IL-23 injection into the skin. Recombinant human IL-23 (with linker) was injected once daily for 3 additional days and tissue was collected for cytokine assessment. Inhibition of cytokine production was demonstrated for the antibodies. The results of three experiments are shown in the table below (exp. 1: rows 1-7, exp. 2: rows 8-10, exp. 3: rows 11-14).

TABLE 15

| | Ear Tissue IL-17 pg/ml Mean +/− SEM | Ear Tissue IL-17 Percent Inhibition | Ear Tissue IL-22 pg/ml Mean +/− SEM | Ear Tissue IL-22 Percent Inhibition |
|---|---|---|---|---|
| 0.1% BSA + Citrate Buffer i.p. (Unstimulated Control) | 3 +/− 1 | NA | 1 +/− 0 | NA |
| 0.3 ug IL-23 + Citrate Buffer i.p. (Vehicle Control) | 25 +/− 3 | NA | 274 +/− 30 | NA |
| 0.3 ug IL-23 + 1 mg/kg Antibody 6B8 | 7 +/− 2 | 81 | 57 +/− 19 | 80 |
| 0.3 ug IL-23 + 1 mg/kg Antibody A | 2 +/− 1 | 101 | 17 +/− 3 | 94 |
| 0.3 ug IL-23 + 1 mg/kg Antibody B | 5 +/− 1 | 93 | 30 +/− 2 | 89 |
| 0.3 ug IL-23 + 1 mg/kg Antibody C | 11 +/− 1 | 66 | 108 +/− 12 | 61 |
| 0.3 ug IL-23 + 1 mg/kg Antibody D | 10 +/− 1 | 67 | 151 +/− 12 | 45 |
| 0.1% BSA + Vehicle (Unstimulated Control) | 14 +/− 1 | NA | 1 +/− 1 | NA |
| 0.3 ug IL-23 + Vehicle | 31 +/− 4 | NA | 129 +/− 29 | NA |
| 0.3 ug IL-23 + 5 mg/kg 24A5 | 14 +/− 1 | 102 | 10 +/− 5 | 93 |
| 0.1% BSA + mIgG (Unstimulated Control) | 17 +/− 1 | NA | 4 +/− 1 | NA |
| 0.3 ug IL-23 + mIgG (Vehicle Control) | 30 +/− 2 | NA | 208 +/− 40 | NA |
| 0.3 ug IL-23 + 5 mg/kg 24A5 | 16 +/− 0 | 109 | 28 +/− 5 | 88 |
| 0.3 ug IL-23 + 5 mg/kg 18E5 | 21 +/− 2 | 70 | 53 +/− 41 | 80 |

Example 8: Pharmacokinetic Studies in Cynomolgus Monkey

Humanized anti-IL-23p19 antibodies were administered by ten minute intravenous infusion at a dose of 1.0 mg/kg to three cynomolgus monkeys. Serum samples were collected over a 6 week time course and free antibody concentrations were measured using a specific ELISA. The serum concentration-time profiles for the antibodies and the corresponding pharmacokinetic parameters are summarized in the Table 16 below.

TABLE 16

| Antibody | CL (ml/d/kg) | Vol (ml/kg) | AUC (nM · h/ml) | $T_{1/2}$ (days) | MRT (days) |
|---|---|---|---|---|---|
| Antibody A | 5.2 | 88 | 32262 | 12.1 | 17.2 |
| Antibody B | 6.0 | 87 | 27030 | 10.1 | 14.8 |
| Antibody C | 4.7 | 91 | 34642 | 14.1 | 19.6 |
| Antibody D | 3.4 | 67 | 47633 | 12.6 | 19.8 |

Example 9: Expression in NS0 Cells and Biophysical Data

Transfection of NS0 cells and generation of stable pools: NS0 cells were grown in the presence of 1% FBS before transfection. 40×10e6 cells were collected and resuspended in 0.8 ml in media containing 2% FBS with 20 ug of linearized DNA (heavy chain and light chain expression vectors) and then cells were incubated on ice for approximately 15 min before electroporation of the cells at 750V/25 uF (Bio-Rad Gene Pulser Xcell). Cells were recovered with 2% FBS for approximately 48 hours at 37° C. and 5% CO2 then plated in 96 well plates at 2×10e5 cells/ml containing G418 and mycophenolic acid for 14-21 days until formation of colonies.

Supernatant from 96 well plates with colonies were screened by ELISA. ELISA plates were coated with 1 ug/ml of goat anti-kappa (Southern Biotech, Birmingham, Ala.) in PBS and diluted supernatant were incubated and then detected with goat anti-human IgG Fc-HRP (from Jackson Immuno Research Laboratories, West Grove, Pa.). The positive colonies were pooled for scale up. Titers for antibody production were determined by ForteBio using protein A tips according to manufacture protocol. The titers for Antibody A and Antibody D were between 250-350 mg/L, with more than 80% recovery from protein purification, and more than 94% monomer after IEX purification. Proteins were resuspended in a final buffer containing 20 mM Sodium Citrate and 115 mM NaCl, pH 6.0 and are stable at 4° C. for at least 4 months and with solubility up to 100 mg/ml in this buffer.

TABLE 17

|  | Protein A Column | | | IEX Column | |
| --- | --- | --- | --- | --- | --- |
|  | Titer (mg/L) | Yield (mg/L) | Recovery | Yield (mg/L) | Recovery |
| Antibody A | 345 | 275 | 80% | 221 | 80% |
| Antibody D | 248 | 225 | 90% | 175 | 78% |

TABLE 18

| | Quality | | Stability | | | | Solubility |
| --- | --- | --- | --- | --- | --- | --- | --- |
| | AUC fresh (% M) | SEC fresh (% M) | AUC 1 month (% M) | SEC 1 month (% M) | AUC 4 months (% M) | SEC 4 months (% M) | AUC at 100 mg/ml (% M) |
| Antibody A | 98 | 99 | 97 | 99 | 96 | 99 | 99 |
| Antibody D | 94 | 100 | 98 | 100 | 99 | 99 | 97 |

AUC: Analytical Ultracentrifugation as measured by the sedimentation velocity method at concentrations of 0.5-1 mg/ml; SEC: Size exclusion chromatography; % M: percent monomer.

Example 10: Epitope Mapping

Hydrogen/Deuterium Exchange Mass Spectrometry (HXMS) was employed to map the epitope of Antibody A binding to human IL-23p19. This method determined the susceptibility of the amide backbone hydrogens of IL-23p19 to exchange with $D_2O$. The experiment was conducted with IL-23 alone and IL-23 with added Antibody A. Regions of the IL-23p19 sequence showing significant protection from exchange due to binding of Antibody A were thus identified. Resolution of the method is determined by the peptides produced by digestion with pepsin or Protease XVIII. These IL-23p19 derived peptides were identified by additional control experiments with unexchanged samples employing standard accurate mass and HPLC MS/MS technologies.

Recombinant human IL-23 was used. For the protein+antibody sample, 50 ul of IL-23 (0.8 mg/ml) was incubated with 10 ul of Antibody A (12.7 mg/ml) for 15 minutes at room temperature. The final molar ratio Antibody A/IL-23 was 1.2:1.

For the exchange 5 ul of IL-23 protein was added to 50 ul deuterated buffer (50 mM PBS in $D_2O$) and incubated for 100 seconds at room temperature. 50 ul of 2M Urea/0.5M TCEP was added and incubated for 60 seconds at room temperature. 5 ul pepsin or Protease XVIII (4 mg/ml in 0.1% formic acid) was added and the sample was immediately cooled to 4° C.

After 5 minutes 50 ul of sample was injected onto a Shimadzu HPLC system (SCL10A controller and two LC10AD pumps) under the following conditions:
Mobile Phase A=99/1/0.1 (water/acetonitrile/formic acid).
Mobile Phase B=95/5/0.1 (acetonitrile/water/formic acid).
Flow rate=100 ul/min.
Column=Phenomenex Jupiter C5, 5u, 50×1.0 mm.
Mobile phase lines, column, injector loop are in ice baths.
Gradient=Time 0 (3% B), Time 2.2 (3% B), Time 10.1 (90% B), Time 12.0 (90% B), Time 12.1 (3% B).
Mass Spectrometry was carried out as follows:
Mass Spec=Thermo Orbitrap Velos (0900865).
Methods:
A. Fragmentation (to ID peptides): 12 minute acquisition time (3 minute start delay), full-scan FTMS at 30,000 resolution, seven ion trap data dependant scans (CID).
B. MS Runs: 12 minute acquisition time (3 minute start delay), full-scan FTMS at 60,000 resolution.

Pepsin and Protease XVIII peptides were identified using fragmentation data and the program Proteome Discoverer (Thermoscientific, Waltham, Mass.). Identified peptides were visually compared (protein alone vs. protein with antibody present) using Xcalibur software (Thermoscientific). No significant shifts in exchange were observed for IL-23 alone vs. IL-23 with Antibody A outside of the IL-23p19 region. For the p19 portion of the protein, data was analyzed using the program PepMap (Thermoscientific). This program calculates the average mass for exchanged peptides. PepMap results were checked and those peptides that did not yield verified results were calculated with the aid of Microsoft Excel.

The regions of the IL-23 sequence showing significant protection from exchange due to binding of Antibody A were identified as amino acid residues 108 to 126 of SEQ ID NO:181 and amino acid residues 137 to 151 of SEQ ID NO:181.

What is claimed is:

1. A method for treating a subject having a disorder associated with increased interleukin 23 (IL-23) expression comprising administering to the subject an anti-IL-23p19 antibody or antigen-binding fragment or a pharmaceutical composition comprising an anti-IL-23p19 antibody or antigen-binding fragment and a pharmaceutically acceptable carrier, which antibody or antigen-binding fragment binds to human IL-23, wherein the antibody or antigen-binding fragment thereof comprises: a) a light chain variable region comprising the amino acid sequence of SEQ ID NO:19 (CDR1-L); the amino acid sequence of SEQ ID NO:20 (CDR2-L); and the amino acid sequence of SEQ NO:21 (CDR3-L); and b) a heavy chain variable region comprising the amino acid sequence of SEQ ID NO: 63, 66, 67 or 68 (CDR1-H); the amino acid sequence of SEQ ID NO:64 (CDR2-H); and the amino acid sequence of SEQ ID NO:65 (CDR3-H).

2. The method of claim 1, wherein the anti-IL-23p19 antibody or antigen-binding fragment comprises a light chain variable region comprising an amino acid sequence of SEQ ID NO: 160 and a heavy chain variable region comprising an amino acid sequence of SEQ ID NO: 166.

3. The method of claim 1, wherein the anti-IL-23p19 antibody or antigen-binding fragment comprises a light chain comprising an amino acid sequence of SEQ ID NO: 174 and a heavy chain comprising an amino acid sequence of SEQ ID NO: 176.

4. A method for treating an inflammatory disease, an autoimmune disease, or cancer comprising administering to a subject in need thereof an effective amount of an anti-IL-23p19 antibody or antigen-binding fragment or a pharmaceutical composition comprising an anti-IL-23p19 antibody or antigen-binding fragment and a pharmaceutically acceptable carrier, wherein the antibody or antigen-binding fragment thereof comprises: a) a light chain variable region comprising the amino acid sequence of SEQ ID NO:19 (CDR1-L); the amino acid sequence of SEQ ID NO:20 (CDR2-L); and the amino acid sequence of SEQ ID NO:21 (CDR3-L); and b) a heavy chain variable region comprising the amino acid sequence of SEQ ID NO: 63, 66, 67 or 68 (CDR1-H); the amino acid sequence of SEQ ID NO:64 (CDR2-H); and the amino acid sequence of SEQ ID NO:65 (CDR3-H).

5. The method of claim 4, wherein the anti-IL-23p19 antibody or antigen-binding fragment comprises a light chain variable region comprising an amino acid sequence of SEQ ID NO: 160 and a heavy chain variable region comprising an amino acid sequence of SEQ ID NO: 166.

6. The method of claim 4, wherein the anti-IL-23p19 antibody or antigen-binding fragment comprises a light chain comprising an amino acid sequence of SEQ ID NO: 174 and a heavy chain comprising an amino acid sequence of SEQ ID NO: 176.

7. A method for inhibiting the binding of IL-23 to the IL-23 receptor on a mammalian cell, comprising administering to the cell an anti-IL-23p19 antibody or antigen-binding fragment, whereby signaling mediated by the IL-23 receptor is inhibited, wherein the antibody or antigen-binding fragment thereof comprises:
   a) a light chain variable region comprising the amino acid sequence of SEQ ID NO:19 (CDR1-L); the amino acid sequence of SEQ ID NO:20 (CDR2-L); and the amino acid sequence of SEQ ID NO:21 (CDR3-L); and
   b) a heavy chain variable region comprising the amino acid sequence of SEQ ID NO: 63, 66, 67 or 68 (CDR1-H); the amino acid sequence of SEQ ID NO:64 (CDR2-H); and the amino acid sequence of SEQ ID NO:65 (CDR3-H).

8. The method of claim 7, wherein the anti-IL-23p19 antibody or antigen-binding fragment comprises a light chain variable region comprising an amino acid sequence of SEQ ID NO: 160 and a heavy chain variable region comprising an amino acid sequence of SEQ ID NO: 166.

9. The method of claim 7, wherein the anti-IL-23p19 antibody or antigen-binding fragment comprises a light chain comprising an amino acid sequence of SEQ ID NO: 174 and a heavy chain comprising an amino acid sequence of SEQ ID NO: 176.

* * * * *